US010933025B2

(12) United States Patent
Irache Garreta et al.

(10) Patent No.: US 10,933,025 B2
(45) Date of Patent: Mar. 2, 2021

(54) NANOPARTICLES FOR ENCAPSULATING COMPOUNDS, THE PREPARATION AND USES THEREOF

(71) Applicant: INNOUP FARMA, S.L., Navarra (ES)

(72) Inventors: Juan Manuel Irache Garreta, Navarra (ES); Judit Huarte Ciganda, Navarra (ES); Laura Inchaurraga Casadamón, Navarra (ES); Luisa Fernanda Ruiz Gatón, Navarra (ES); Nekane Martín Arbellá, Navarra (ES)

(73) Assignee: INNOUP FARMA, S.L., Navarra (ES)

( * ) Notice: Subject to any disclaimer, the term of this patent is extended or adjusted under 35 U.S.C. 154(b) by 0 days.

(21) Appl. No.: 15/531,926

(22) PCT Filed: Nov. 30, 2015

(86) PCT No.: PCT/EP2015/078005
§ 371 (c)(1),
(2) Date: May 31, 2017

(87) PCT Pub. No.: WO2016/087340
PCT Pub. Date: Jun. 9, 2016

(65) Prior Publication Data
US 2017/0326074 A1 Nov. 16, 2017

(30) Foreign Application Priority Data

Dec. 1, 2014 (EP) ..................................... 14382486

(51) Int. Cl.
| | | |
|---|---|---|
| *A61K 9/51* | (2006.01) | |
| *C08F 216/12* | (2006.01) | |
| *A61K 47/69* | (2017.01) | |
| *A61K 47/32* | (2006.01) | |
| *A61K 47/60* | (2017.01) | |
| *A61K 9/00* | (2006.01) | |
| *C08G 81/00* | (2006.01) | |
| *A61K 31/337* | (2006.01) | |
| *A61K 31/4745* | (2006.01) | |
| *A61K 45/06* | (2006.01) | |
| *C08G 81/02* | (2006.01) | |
| *C08F 222/06* | (2006.01) | |

(52) U.S. Cl.
CPC .......... *A61K 9/5138* (2013.01); *A61K 9/0019* (2013.01); *A61K 9/5115* (2013.01); *A61K 9/5123* (2013.01); *A61K 9/5146* (2013.01); *A61K 9/5192* (2013.01); *A61K 31/337* (2013.01); *A61K 31/4745* (2013.01); *A61K 45/06* (2013.01); *A61K 47/32* (2013.01); *A61K 47/60* (2017.08); *A61K 47/6933* (2017.08); *C08G 81/00* (2013.01); *C08G 81/025* (2013.01); *C08F 216/12* (2013.01); *C08F 222/06* (2013.01)

(58) Field of Classification Search
None
See application file for complete search history.

(56) References Cited

U.S. PATENT DOCUMENTS

| | | | |
|---|---|---|---|
| 8,628,801 B2 * | 1/2014 | Garreta ................ | A61K 9/5138 424/489 |
| 9,351,940 B2 | 5/2016 | Salman et al. | |
| 9,522,197 B2 | 12/2016 | Agüeros Bazo et al. | |
| 2006/0188566 A1 | 8/2006 | Liversidge et al. | |
| 2010/0068286 A1 | 1/2010 | Kobata et al. | |
| 2010/0068285 A1 | 3/2010 | Zale et al. | |

FOREIGN PATENT DOCUMENTS

| | | |
|---|---|---|
| EA | 201170038 A1 | 8/2011 |
| EA | 015987 B1 | 1/2012 |
| EP | 1752141 A1 | 2/2007 |
| EP | 1752142 A2 | 2/2007 |
| EP | 2510930 A1 | 10/2012 |
| WO | 2005104648 A2 | 11/2005 |
| WO | 2008129106 A2 | 10/2008 |
| WO | 2009121997 A2 | 10/2009 |

OTHER PUBLICATIONS

Zabaleta, Virginia, et al. "Oral administration of paclitaxel with pegylated poly (anhydride) nanoparticles: permeability and pharmacokinetic study." European Journal of Pharmaceutics and Biopharmaceutics 81.3 (2012): 514-523.*
Pecchio, Marisin, Maria Jesús Renedo Omaechevarria, and M. Carmen Dios-Viéitez. "Influence of Poly (ethylene glycol) in Cyclosporine A Loaded PVM/MA Nanoparticles and Oral Absorption of the Drug." Current Trends in Biotechnology and Pharmacy 5.4 (2011): 1383-1396.*
Nagavarma, B. V. N., et al. "Different techniques for preparation of polymeric nanoparticles—a review." Asian J. Pharm. Clin. Res 5.3 (2012): 16-23.*
Allouche et al (chapter 2 in: R. Brayner et al (eds), Nanomaterials: A danger or a Promise?, 2013, pp. 27-74). (Year: 2013).*
Hayden, Thomas V., et al.; "The road map to oral bioavailability: an industrial perspective," Expert Opinion on Drug Metabolism & Toxicology, 2006, pp. 591-608, vol. 2.
Woodley, J., "Bioadhesion: New Possibilities for Drug Administration?" Clin Pharmacokinet, 2001, pp. 77-84, vol. 40.
Gref, R., et al., "Biodegradable long-circulating polymeric nanospheres," Science, 1994, pp. 1600-1603, vol. 263.

(Continued)

*Primary Examiner* — Celeste A Roney
(74) *Attorney, Agent, or Firm* — Tristan A. Fuierer; Olive Law Group, PLLC

(57) ABSTRACT

The present invention relates to nanoparticles for encapsulating biologically active compounds, comprising a matrix of new polymer conjugates. The invention also relates to a process for producing both the conjugates and nanoparticles, to compositions containing said conjugates or nanoparticles, and applications thereof. The invention is applicable in the pharmaceutical sector and in the nanotechnology sector.

16 Claims, 12 Drawing Sheets

(56) References Cited

OTHER PUBLICATIONS

Peracchia MT., et al.; "Complement consumption by poly(ethylene glycol) in different conformations chemically coupled to poly(isobutyl 2-cyanoacrylate)," Life Sci, 1997, pp. 749-761, vol. 61.
Torchilin, V.P., et al.; "Polymer-coated long-circulating microparticulate pharmaceuticals," J. Microencapsulation, 1998, pp. 1-19, vol. 15.
Stolnik, S. et al.; "Long circulating microparticulate drug carriers," Advanced Drug Delivery Reviews, 1995, pp. 195-214, vol. 16.
Beletsi, A. et al.; "Effect of preparative variables on the properties of poly(dl-lactide-co-glycolide)-methoxypoly (ethyleneglycol) copolymers related to their application in controlled drug delivery," Int J Pharm, 1999, pp. 187-197, vol. 182.
Neal, Jonathan C., et al.; "In Vitro Displacement by Rat Serum of Adsorbed Radiolabeled Poloxamer and Poloxamine Copolymers from model Biodegradable Nanospheres," J. Pharmaceutical Sci., 1998, pp. 1242-1248, vol. 87.
Davis, Stanley S.; "Formulation strategies for absorption windows," Drug Discovery Today, 2005, pp. 249-257, vol. 10.
Hermansky, S.J., et al.; "Effects of Polyethylene Glycol 400 (PEG 400) Following 13 Weeks of Gavage Treatment in Fischer—344 Rats," Food Chem Toxic, 1995, pp. 139-149, vol. 33.
International Search Report, dated Feb. 1, 2016.
International Preliminary Report on Patentability, dated Dec. 8, 2016.
Jaeghere, F., et al.; "Cellular Uptake of PEO Surface-Modified Nanoparticles: Evaluation of Nanoparticles Made of PLA: PEO Diblock and Triblock Copolymers," Journal of Drug Targeting, 2000, pp. 143-153, vol. 8, DOI: 10.3109/10611860008996860.
Hwang, H.Y., Kim, I.S., Kwon, I.C., Kim, Y.H., 2008. Tumor targetability and antitumor effect of docetaxel-loaded hydrophobically modified glycol chitosan nanoparticles. J. Control. Release. 18, 23-31.
T. Ikezoe, Y. Hisatake, T. Takeuchi, Y. Ohtsuki, Y. Yang, J.W. Said, H. Taguchi, H.P. Koeffler, HIV-1 protease inhibitor, ritonavir: a potent inhibitor of CYP3A4, enhanced the anticancer effects of docetaxel in androgen-independent prostate cancer cells in vitro and in vivo, Cancer Research, 64 (2004) 7426-7431.
Inchaurraga, L., Martín-Arbella, N., Zabaleta, V., Quincoces, G., Peñuelas, I., Irache, J.M., 2015. In vivo study of the mucuspermeating properties of PEG-coated nanoparticles following oral administration. Eur. J. Pharm. Biopharm. 97, 280-289.
Jiang, H., Tao, W., Zhang, M., Pan, S., Kanwar, J.R., Sun, X., 2010. Low-dose metronomic paclitaxel chemotherapy suppresses breast tumors and metastases in mice. Cancer Invest. 28, 74-84.
Johnson, B.M., Charman, W.N., Porter, C.J., 2002. An in vitro examination of the impact of polyethylene glycol 400, Pluronic P85, and vitamin E d-alpha-tocopheryl polyethylene glycol 1000 succinate on P-glycoprotein efflux and enterocyte-based metabolism in excised rat intestine. AAPS PharmSciTech. 4, 193-205.
Jones, S., 2006. Head-to-Head: docetaxel challenges paclitaxel. Eur. J. Cancer Suppl. 4, 4-8.
R.S. Kerbel, B.A. Kamen, The anti-angiogenic basis of metronomic chemotherapy, Nature Reviews Cancer, 4 (2004) 423-436.
Z. Khatun, M Nurunnabi, G.R. Reeck, K.J. Cho, Y.K. Lee, Oral delivery of taurocholic acid linked heparin-docetaxel conjugates for cancer therapy, Journal of Controlled Release, 170 (2013) 74-82.
Kuppens, I.E., Bosch, T.M., van Maanen, M.J., Rosing, H., Fitzpatrick, A., Beijnen, J.H., et al., 2005. Oral bioavailability of docetaxel in combination with OC144-093 (ONT-093). Cancer Chemother. Pharmacol. 55, 72-78.
E. Lee, H. Kim, I.H. Lee, S. Jon, In vivo antitumor effects of chitosan-conjugated docetaxel after oral administration, Journal of Controlled Release, 140 (2009) 79-85.
L. Li, F. Tang, H. Liu, T. Liu, N. Hao, D. Chen, X. Teng, J. He, In vivo delivery of silica nanorattle encapsulated docetaxel for liver cancer therapy with low toxicity and high efficacy, ACS Nano, 4 (2010) 6874-6882.

G. Liu, E. Franssen, M.I. Fitch, E. Warner, Patient preferences for oral versus intravenous palliative chemotherapy, Journal of Clinical Oncology, 15 (1997) 110-115.
W.J. Loos, S.D. Baker, J. Verweij, J.G. Boonstra, A. Sparreboom, Clinical pharmacokinetics of unbound docetaxel: role of polysorbate 80 and serum proteins, Clinical Pharmacology & Therapeutics, 74 (2003) 364-371.
Malingré, M.M., Beijnen, J.H., Schellens, J.H., 2001. Oral delivery of taxanes. Invest. New Drugs. 19, 155-162.
M.M. Malingré, D.J. Richel, J.H. Beijnen, H. Rosing, F.J. Koopman, W.W. Ten Bokkel Huinink, M.E. Schot, J.H. Schellens, Coadministration of cyclosporine strongly enhances the oral bioavailability of docetaxel, Journal of Clinical Oncology 19 (2001) 1160-1166.
L. Mangatal, M.T. Adeline, D. Guenard, F. Gueritte-Voegelein, P. Potier, Application of the vicinal oxyamination reaction with asymmetric induction to the hemisynthesis of taxol analogues, Tetrahedron, 45 (1989) 4177-4190.
S. Mazzaferro, K. Bouchemal, R. Skanji, C. Gueutin, H. Chacun, G. Ponchel, Intestinal permeation enhancement of docetaxel encapsulated into methyl-$\beta$-cyclodextrin/poly(isobutylcyanoacrylate) nanoparticles coated with thiolated chitosan, Journal of Control Release, 162 (2012) 568-574.
Mei, L., Zhang, Z., Zhao, L., Huang, L., Yang, X.L., Tang, J., et al., 2013. Pharmaceutical nanotechnology for oral delivery of anticancer drugs. Adv. Drug Deliv. Rev. 65, 880-890.
L. Mei, Y. Zhang, Y. Zheng, G. Tian, C. Song, D. Yang, H. Chen, H. Sun, Y. Tian, K. Liu, Z. Li, L. Huang, A Novel Docetaxel-Loaded Poly (ɛ-Caprolactone)/Pluronic F68 Nanoparticle Overcoming Multidrug Resistance for Breast Cancer Treatment, Nanoscale Research Letters, 4 (2009) 1530-1539.
J.J. Moes, S.L.W. Koolen, A.D.R. Huitema, J.H.M. Schellens, J.H. Beijnen, B. Nuijen, Pharmaceutical development and preliminary clinical testing of an oral solid dispersion formulation of docetaxel (ModraDoc001), International Journal of Pharmaceutics, 420 (2011) 244-250.
Moulder, J.F., Stickle, W.F., Sobol, P.E., Bomben, K.D., Chastain, J., 1992. Handbook of X-ray Photoelectron Spectroscopy, Perkin-Elmer Corporation Physical Electronics Division, Eden Prairie, MN.
F. Muggia, D. Kudlowitz, Novel Taxanes, Anticancer Drugs, 25 (2014) 593-598.
Nassar, T., Attili-Qadri, S., Harush-Frenkel, O., Farber, S., Lecht, S., Lazarovici, P., et al., 2011. High plasma levels and effective lymphatic uptake of docetaxel in an orally available nanotransporter formulation. Cancer Res. 71, 3018-3028.
Nieuweboer, A.J., de Morrée, E.S., de Graan, A.J., Sparreboom, A., de Wit, R., Mathijssen, R.H., 2015. Inter-patient variability in docetaxel pharmacokinetics: a review. Cancer Treat. Rev. 41, 605-613.
Ojer, P., de Cerain, A.L., Areses, P., Peñuelas, I., Irache, J.M., 2012. Toxicity studies of poly(anhydride) nanoparticles as carriers for oral drug delivery. Pharm. Res. 29, 2615-2627.
Ojer, P., Neutsch, L., Gabor, F., Irache, J.M., de Cerain, A.L., 2013. Cytotoxicity and cell interaction studies of bioadhesive poly(anhydride) nanoparticles for oral antigen/drug delivery. J. Biomed. Nanotechnol. 9, 1891-1903.
V.J. O'Neill, C.J. Twelves, Oral cancer treatment: developments in chemotherapy and beyond, British Journal of Cancer, 87 (2002) 933-937.
Q. Quan, D.W. Kim, N. Marasini, D.H. Kim, J.K. Kim, J.O. Kim, C.S. Yong, H.G. Choi, Physicochemical characterization and in vivo evaluation of solid self-nanoemulsifying drug delivery system for oral administration of docetaxel, Journal of Microencapsulation, 30 (2013) 307-314.
J.M. Rabanel, P. Hildgen, X. Banquy, Assessment of PEG on polymeric particles surface, a key step in drug carrier translation, Journal of Controlled Release, 185 (2014) 71-87.
I. Ringel, S.B. Horwitz, Studies with RP 56976 (Taxotere): a semisynthetic analogue of taxol, Journal of the National Cancer Institute, 83(1991) 288-291.

(56) References Cited

OTHER PUBLICATIONS

Ritger, P.L., Peppas, N.A., 1987. A simple equation for description of solute release I. Fickian and non-fickian release from non-swellable devices in the form of slabs, spheres, cylinders or discs. J. Control. Release. 5, 23-36.
Ruiz, C.C., Hierrezuelo, J., Molina-Bolívar, J., 2008. Effect of glycine on the surface activity and micellar properties of N-decanoyl-N-methylglucamide. Colloid Polym. Sci. 286, 1281-1289.
H.H. Salman, C. Gamazo, P.C. de Smidt, G. Russell-Jones, J.M. Irache, Evaluation of bioadhesive capacity and immunoadjuvant properties of vitamin B12—Gantrez nanoparticles, Pharmaceutical Research, 25 (2008) 2859-2868.
H. H. Salman, C. Gamazo, M. Agüeros, J. M. Irache, Bioadhesive capacity and immunoadjuvant properties of thiamine-coated nanoparticles, Vaccine, 25 (2007) 8123-8132.
Saremi, S., Dinarvand, R., Kebriaeezadeh, A., Ostad, S.N., Atyabi, F., 2011. Enhanced oral delivery of docetaxel using thiolated chitosan nanoparticles: preparation, in vitro and in vivo studies, Int. J. Nanomed. 6, 119-128.
Seo, Y.G., Kim, D.H., Ramasamy, T., Kim, J.H., Marasini, N., Oh, Y.K., et al., 2013. Development of docetaxel-loaded solid self-nanoemulsifying drug delivery system (SNEDDS) for enhanced chemotherapeutic effect. Int. J. Pharm. 452, 412-420.
M. Shou, M. Martinet, k.r. korzekwa, K.W. Krausz, F.J. Gonzalez, H.V. Gelboin, Role of human cytochrome P450 3A4 and 3A5 in the metabolism of taxotere and its derivatives: enzyme specificity, interindividual distribution and metabolic contribution in human liver, Pharmacogenetics, 8 (1998) 391-401.
Tang, X., Wang, G., Shi, R., Jiang, K., Meng, L., Ren, H., et al., 2016. Enhanced tolerance and antitumor efficacy by docetaxel-loaded albumin nanoparticles. Drug Deliv. 23, 2686-2696.
A.J. Ten Tije, J.Verweij, W.J. Loos, A. Sparreboom, Pharmacological effects of formulation vehicles: implications for cancer chemotherapy, Clinical Pharmacokinetics, 42 (2003) 665-685.
J.M.M. Terwogt, J.H.M. Schellens, W.W.T. Huinink, J.H. Beijnen, Clinical pharmacology of anticancer agents in relation to formulations and administration routes, Cancer Treatment Reviews, 25 (1999) 83-101.
Tobío, M., Sánchez, A., Vila, A., Soriano, I.I., Evora, C., Vila-Jato, J.L., Alonso, M.J., 2000. The role of PEG on the stability in digestive fluids and in vivo fate of PEG-PLA nanoparticles following oral administration. Colloids Surf. B Biointerfaces. 18, 315-323.
A.E. van Herwaarden, E. Wagenaar, C.M. van der Kruijssen, R.A. van Waterschoot, J.W. Smit, J.Y. Song, M.A. van der Valk, O. van Tellingen, J.W. van der Hoorn, H. Rosing, J.H. Beijnen, A.H. Schinkel, Knockout of cytochrome P450 3A yields new mouse models for understanding xenobiotic metabolism, Journal of Clinical Investigation, 117 (2007) 3583-3592.
Van Tellingen, O., Beijnen, J.H., Verweij, J., Scherrenburg, E.J., Nooijen, W.J., Sparreboom, A., 1999. Rapid esterase-sensitive breakdown of polysorbate 80 and its impact on the plasma pharmacokinetics of docetaxel and metabolites in mice. Clin. Cancer Res. 5, 2918-2924.
R.A. van Waterschoot, J.S. Lagas, E. Wagenaar, C.M. van der Kruijssen, A.E. van Herwaarden, J.Y. Song, R.W. Rooswinkel, O. van Tellingen, H. Rosing, J.H. Beijnen, A.H. Schinkel, Absence of both cytochrome P450 3A and P-glycoprotein dramatically increases docetaxel oral bioavailability and risk of intestinal toxicity, Cancer Research, 69 (2009) 8996-9002.
J. Verweij, M. Calvel, B. Chevalier, Paclitaxel (Taxol) and docetaxel (Taxotere): not simply two of a kind, Annals of Oncology, 5 (1994) 495-505.
P. Vrignaud, D. Sémiond, P.Lejeune, H. Bouchard, L. Calvet, C. Combeau, J.F. Riou, A. Commerçon, F. Lavelle, M.C. Bissery, Preclinical antitumor activity of cabazitaxel, a semisynthetic taxane active in taxane-resistant tumors, Clinical Cancer Research, 19 (2013) 2973-2983.
Y.Y. Wang, S.K. Lai, J.S. Suk, A. Pace, R. Coone, J. Hanes, Addressing the PEG mucoadhesivity paradox to engineer nanoparticles that "slip" through the human mucus barrier, Angewandte Chemie International Edition, 47 (2008) 9726-9729.
S.T. Wolford, R.A. Schroer, F.Z. Gohs, P.P. Gallo, M. Brodeck, H.B. Falk, R. Ruhren, Reference range data base for serum chemistry and hematology values in laboratory animals. Journal of Toxicology and Environmental Health, 18 (1986)161-188.
Wu, H., Xin, Y., Zhao, J., Sun, D., Li, W., Hu, Y., et al., 2011. Metronomic docetaxel chemotherapy inhibits angiogenesis and tumor growth in a gastric cancer model. Cancer Chemother. Pharmacy. 68, 879-887.
J. Wun, Q. Shen, L. Fang, Sulfobutylether-β-cyclodextrin/chitosan nanoparticles enhance the oral permeability and bioavailability of docetaxel, Drug Development and Industrial Pharmacy, 39 (2013) 1010-1019.
Yan, Y.D., Kim, D.H., Sung, J.H., Yong, C.S., Choi, H.G., 2010. Enhanced oral bioavailability of docetaxel in rats by four consecutive days of pre-treatment with curcumin. Int. J. Pharm. 399, 116-120.
N. Yanasarn, B.R. Sloat, Z. Cui, Nanoparticles engineered from lecithin-in-water emulsions as a potential delivery system for docetaxel, International Journal of Pharmaceutics, 379 (2009) 174-180.
Yang, S.H., Lee, J.H., Lee, D.Y., Lee, M.G., Lyuk, K.C., Kim, S.H., 2011. Effects of morin on the pharmacokinetics of docetaxel in rats with 7,12-dimethylbenz[a]anthracene (DMBA)-induced mammary tumors. Arch. Pharm. Res. 34, 1729-1734.
Y.M. Yin, F.D. Cui, C.F. Mu, M.K. Choi, J.S. Kim, S.J. Chung, C.K. Shim, D.D. Kim, Docetaxel microemulsion for enhanced oral bioavailability: preparation and in vitro and in vivo evaluation, Journal of Controlled Release, 140 (2009) 86-94.
Yoncheva, K., Lizarraga, E., Irache, J.M., 2005. Pegylated nanoparticles based on poly(methyl vinyl ether-co-maleic anhydride): preparation and evaluation of their bioadhesive properties. Eur. J. Pharm. Sci. 24, 411-419.
K. Yoncheva, M.N. Centelles, J.M. Irache, Development of bioadhesive amino-pegylated poly(anhydride) nanoparticles designed for oral DNA delivery, Journal of Microencapsulation, 25 (2008) 82-89.
K. Yoncheva, L. Guembe, M.A. Campanero, J.M. Irache, Evaluation of bioadhesive potential and intestinal transport of pegylated poly(anhydride) nanoparticles, International Journal of Pharmaceutics, 334 (2007) 156-165.
K. Yoncheva, S. Gómez, M.A. Campanero, C. Gamazo, J.M. Irache, Bioadhesive properties of pegylated nanoparticles, Expert Opinion on Drug Delivery, 2 (2005) 205-218.
D.H. Yu, F.Q. Ban, M. Zhao, Q. Lu, J.F. Lovell, F. Bai, C. Wang, Y-Y. Guan, X. Luan, Y.R. Liu, C. Fang, H.Z. Chen, The use of nanoparticulate delivery systems in metronomic chemotherapy, Biomaterials, 34 (2013) 3925-3937.
V. Zabaleta, P. Calleja, S. Espuelas, L. Corrales, R. Pío, M. Agüeros, J.M. Irache, Mucopenetrating nanoparticles: vehicles for the oral administration of paclitaxel, Annales Pharmaceutiques Françaises, 71 (2013) 109-118.
V. Zabaleta, M.A. Campanero, J.M. Irache, An HPLC with evaporative light scattering detection method for the quantification of PEGs and Gantrez in PEGylated nanoparticles, Journal of Pharmaceutical and Biomedical Analysis, 44 (2007) 1072-1078.
V. Zabaleta, G. Ponchel, H. Salman, M. Agueros, C. Vauthier, J.M. Irache, Oral administration of paclitaxel with pegylated poly(anhydride) nanoparticles: Permeability and pharmacokinetic study, European journal of pharmaceutics and biopharmaceutics : official journal of Arbeitsgemeinschaft fur Pharmazeutische Verfahrenstechnik e,V, 81 (2012) 514-523.
L. Zhang, N. Zhang, How nanotechnology can enhance docetaxel therapy, International Journal of Nanomedicine, 8 (2013) 2927-2941.
Zhao M., Su, M., Lin, X., Luo, Y., He, H., Cai, C., et al., 2010. Evaluation of docetaxel intravenous lipid emulsion: pharmacokinetics, tissue distribution, antitumor activity, safety and toxicity. Pharm. Res. 27, 1687-1702.
L. van Zuylen, J. Verweij, A. Sparreboom, Role of formulation vehicles in taxane pharmacology, Investigational New Drugs, 19 (2001) 125-141.
M. Agüeros, V. Zabaleta, S. Espuelas, M.A. Campanero, J.M. Irache, Increased oral bioavailability of paclitaxel by its encapsu-

(56) References Cited

OTHER PUBLICATIONS lation through complex formation with cyclodextrins in poly(anhydride) nanoparticles, Journal of Control Release, 145 (2010) 2-8.

Arbos, P., Wirth, M., Arangoa, M.A., Gabor, F., Irache, J.M., 2003. Gantrez® AN as a new polymer for the preparation of ligand-nanoparticle conjugates. J. Control. Release. 83, 321-330.

P. Arbós, M.A. Campanero, M.A. Arnangoa, M.J. Renedo, J.M. Irache, Influence of the surface characteristics of PVM/MA nanoparticles on their bioadhesive properties, Journal of Controlled Release, 89 (2003) 19-30.

P. Arbós, M. A. Arangoa, M. A. Campanero, J. M. Irache, Quantification of the bioadhesive properties of protein-coated PVM/MA nanoparticles, International Journal of Pharmaceutics, 242 (2002) 129-136.

A. Ardavanis, D. Tryfonopoulos, I. Yiotis, G. Gerasimidis, G. Rigatos, Non-allergic nature of docetaxel-induced acute hypersensitivity reactions, Anticancer drugs, 15 (2004) 581-585.

Attili-Qadri, S., Karra, N., Nemirovski, A., Schwob, O., Talmon, Y., Nassar, T., et al., 2013. Oral delivery system prolongs blood circulation of docetaxel nanocapsules via lymphatic absorption. Proc. Natl. Acad. Sci. USA. 110, 17498-17503.

K. Avgoustakis, Pegylated Poly(Lactide) and Poly(Lactide-Co-Glycolide) Nanoparticles: Preparation, Properties and Possible Applications in Drug Delivery, Current Drug Delivery, 1 (2004) 321-333.

Baer, D.R., Engelhard, M.H., 2010. XPS analysis of nanostructured materials and biological surfaces. J. Electron Spectrosc. Relat. Phenom. 178-179, 415-432.

A. Bader, T. Hansen, G. Kirchner, C. Allmeling, A. Haverich, J.T. Borlak, Primary porcine enterocyte and hepatocyte cultures to study drug oxidation reactions, British Journal of Pharmacology, 129 (2000) 331-342.

J. Baker, J. Ajani, F. Scotté, D. Winther, M. Martin, M.S. Aapro, G. von Minckwitz, Docetaxel-related side effects and their management, European Journal of Oncology Nursing, 13 (2009) 49-59.

G.L. Banna, E. Collovà, V. Gebbia, H. Lipari, P. Giuffrida, S. Cavallaro, R. Condorelli, C. Buscarino, P. Tralongo, F. Ferraù, Anticancer oral therapy: emerging related issues, Cancer Treatment Reviews, 36 (2010) 595-605.

Bardelmeijer, H.A., Ouwehand, M., Buckle, T., Huisman, M.T., Schellens, J.H., Beijnen, J.H., et al., 2002. Low systemic exposure of oral docetaxel in mice resulting from extensive first-pass metabolism is boosted by ritonavir. Cancer Res. 62, 6158-6164.

Barker, N., 2014. Adult intestinal stem cells: critical drivers of epithelial homeostasis and regeneration, Nat Rev Mol Cell Biol 15 (2014) 19-33.

M.C. Bissery, D. Guénard, F. Guéritte-Voegelein, F. Lavelle, Experimental antitumor activity of taxotere (RP 56976, NSC 628503), a taxol analogue, Cancer Research, 51 (1991) 4845-4852.

D.E. Bloom, E.T. Cafiero, E. Jané-Llopis, S. Abrahams-Gessel, L.R. Bloom, S. Fathima, A.B. Feigl, T. Gaziano, M. Mowafi, A. Pandya, K. Prettner, L. Rosenberg, B. Seligman, A.Z. Stein, C. Weinstein, The Global Economic Burden of Noncommunicable Diseases, (2011).

I. Bratu, M-C. Rosu, Promising psyllium-based composite containing TiO2 nanoparticles as aspirin-carrier matrix , Progress in Natural Science: Materials International, 24 (2014) 205-209.

Bruno, R., Hille, D., Riva, A., Vivier, N., ten Bokkel Huinnink, W.W., van Oosterom, A.T., et al., 1998. Population pharmacokinetics/pharmacodynamics of docetaxel in phase II studies in patients with cancer. J. Clin. Oncol. 16, 187-196.

Calleja, P., Espuelas, S., Corrales, L., Pio, R., Irache, J.M., 2014. Pharmacokinetics and antitumor efficacy of paclitaxel-cyclodextrin complexes loaded in mucus-penetrating nanoparticles for oral administration. Nanomedicine. 9, 2109-2121.

Q.X. Cai, K.J. Zhu, D. Chen, L.P. Gao, Synthesis, characterization and in vitro release of 5-aminosalicylic acid and 5-acetyl aminosalicylic acid of polyanhydride-P(CBFAS), European Journal of Pharmaceutics and Biopharmaceutics, 55 (2003) 203-8.

J. Calvo, J.L. Lavandera, M. Agüeros, J.M. Irache, Cyclodextrin/poly(anhydride) nanoparticles as drug carriers for the oral delivery of atovaquone, Biomedical Microdevices, 13 (2011) 1015-1025.

E. Calvo, U. Hoch, D. J. Maslyar, A. W. Tolcher, Dose-escalation phase I study of NKTR-105, a novel pegylated form of docetaxel, Journal of Clinical Oncology, ASCO Annual Meeting Abstracts, 28 (2010) s15 (Abstr TPS160).

Chiou, W.L., Wu, T.C., Jeong, H.Y., 2002. Enhanced oral bioavailability of docetaxel by coadministration of cyclosporine: quantitation and role of P-glycoprotein. J. Clin. Oncol. 20, 1951-1952.

Cho, H.J., Park, J.W., Yoon, I.S., Kim, D.D., 2014. Surface-modified solid lipid nanoparticles for oral delivery of docetaxel: enhanced intestinal absorption and lymphatic uptake. Int. J. Nanomed. 13, 495-504.

Cho, H.J., Yoon, H.Y., Koo, H., Ko, S.H., Shim, J.S., Lee, J.H., et al., 2011. Self-assembled nanoparticles based on hyaluronic acid-ceramide (HA-CE) and Pluronic® for tumor-targeted delivery of docetaxel. Biomaterials. 32, 7181-7190.

S.J. Clarke, L.P. Rivory, Clinical pharmacokinetics of docetaxel, Clinical Pharmacokinetics, 36 (1999) 99-114.

P. Costa, J. M. Sousa Lobo, Modeling and comparison of dissolution profiles, European Journal of Pharmaceutical Sciences, 13 (2001) 123-133.

R. Da Costa Martins, C. Gamazo, M. Sánchez-Martínez, M. Barberán, I. Peñuelas, J.M. Irache, Conjunctival vaccination against Brucella ovis in mice with mannosylated nanoparticles, Journal of Control Release, 162 (2012) 553-560.

De Weger, V.A., Beijnen, J.H., Schellens, J.H., 2014. Cellular and clinical pharmacology of the taxanes docetaxel and paclitaxel—a review. Anticancer Drugs. 25, 488-494.

Deeken, J.F., Slack, R., Weiss, G.J., Ramanathan, R.K., Pishvaian, M.J., Hwang, J., et al., 2013. A phase I study of liposomal-encapsulated docetaxel (LE-DT) in patients with advanced solid tumor malignancies. Cancer Chemother. Pharmacol. 71, 627-633.

Desai, N.P., Trieu, V., Hwang, L.Y., Wu, R., Soon-Shiong, P., Gradishar, W.J., 2008. Improved effectiveness of nanoparticle albumin-bound (nab) paclitaxel versus polysorbate-based docetaxel in multiple xenografts as a function of HER2 and SPARC status. Anticancer Drugs. 19, 899-909.

X. Dong, L. Li, J. Xu, X. Guo, Rheological behavior of PMVE-MA aqueous solution with metallic cations, Frontiers of Chemical Science and Engineering, 5 (2011) 126-130.

Dou, J., Zahng, H., Xiuju, L., Zhang, M., Zhai, G., 2014. Preparation and evaluation in vitro and in vivo of docetaxel loaded mixed micelles for oral administration. Colloids Surf. B Biointerfaces. 114, 20-27.

D.J. Dykes, M.C. Bissery, S.D. Harrison, W.R. Waud, Response of human tumor xenografts in athymic nude mice to docetaxel (RP 56976, Taxotere), Investigational New Drugs, 13 (1995) 1-11.

F.K. Engels, J. Verweij, Docetaxel administration schedule: from fever to tears? A review of randomised studies, European Journal of Cancer, 41 (2005) 1117-1126.

Enlow, E.M., Luft, J.C., Napier, M.E., De Simone, J.M., 2011. Potent engineered PLGA nanoparticles by virtue of exceptionally high chemotherapeutic loadings. Nano Letters. 11, 808-813.

D. Ernest, V.M. Olfert, M. Brenda, VM. Cross, A. Mcwilliam, Guide to the care and use of experimental animals, 2nd ed, Canadian Council on Animal Care (CCAC); (1993).

M.J. Ernsting, W.L. Tang, N.W. MacCallum, S.D. Li, Preclinical pharmacokinetic, biodistribution, and anti-cancer efficacy studies of a docetaxel-carboxymethylcellulose nanoparticle in mouse models, Biomaterials, 33 (2012) 1445-1454.

Esmaeili, F., Dinarvand, R., Ghahremani, M.H., Amini, M., Rouhani, H., Sepehri, N., et al., 2009. Docetaxel-albumin conjugates: preparation, in vitro evaluation and biodistribution studies. J. Pharm. Sci. 98, 2718-2730.

S. Essa, J.M. Rabanel, P. Hildgen, Effect of polyethylene glycol (PEG) chain organization on the physicochemical properties of poly(D, L-lactide) (PLA) based nanoparticles, European Journal of Pharmaceutics and Biopharmaceutics, 75 (2010) 96-106.

(56) References Cited

OTHER PUBLICATIONS

Feng, S.S., Mei, L., Anitha, P., Gan, C.W., Zhou, W., 2009. Poly(lactide)-vitamin E derivate/montmorillonite nanoparticle formulations for the oral delivery of docetaxel. Biomaterials. 30, 3297-3306.

C.W. Gan, S. Chien, S.S. Feng, Nanomedicine: enhancement of chemotherapeutical efficacy of docetaxel by using a biodegradable nanoparticle formulation, Current Pharmaceutical Design, 16 (2010), 2308-2320.

K. Gao, J. Sun, K. Liu, Z. He, Preparation and characterization of a submicron lipid emulsion of docetaxel: submicron lipid emulsion of docetaxel, Drug Development and Industrial Pharmacy, 34 (2008) 1227-1237.

H. Gelderblom, J. Verweij, K. Nooter, A. Sparreboom, Cremophor EL: the drawbacks and advantages of vehicle selection for drug formulation, European Journal of Cancer, 37 (2001) 1590-1598.

J. Gligorov, J.P. Lotz, Preclinical pharmacology of the taxanes: implications of the differences, Oncologist, 9 (2004) 3-8.

Z. Haiqun, D. Jinfeng, Z. Yingjie, A. Liu, G. Zhai, Advances in the formulations of non-injection administration of docetaxel, Journal of Drug Targeting, 22 (2014) 87-94.

Hendrikx, J.J., Lagas, J.S., Wagenaar, E., Rosing, H., Schellens, J.H., Beijnen, J.H., et al., 2014. Oral co-administration of elacridar and ritonavir enhances plasma levels of oral paclitaxel and docetaxel without affecting relative brain accumulation. Br. J. Cancer. 27, 2669-2676.

K.L Hennenfert, R. Govindan, Novel formulations of taxanes: a review. Old wine in a new bottle?, Annals of Oncology, 17 (2006) 735-749.

C. Hennequin, N. Giocanti, V. Favaudon, S-phase specificity of cell killing by docetaxel (Taxotere) in synchronised HeLa cells, British Journal of Cancer, 71 (1995) 1194-1198.

K. Hu, S. Cao, F. Hu, J. Feng, Enhanced oral bioavailability of docetaxel by lecithin nanoparticles: preparation, in vitro, and in vivo evaluation, International Journal of Nanomedicine, 7 (2012) 3537-3545.

Hugger, E.D., Audus, K.L., Borchardt, R.T., 2002. Effects of poly(ethylene glycol) on efflux transporter activity in Caco-2 cell monolayers. J. Pharm. Sci. 91, 1980-1990.

\* cited by examiner

NANOPARTICLES FOR ENCAPSULATING COMPOUNDS, THE PREPARATION AND USES THEREOF

CROSS-REFERENCE TO RELATED APPLICATIONS

This application is filed under the provisions of 35 U.S.C. § 371 and claims the priority of International Patent Application No. PCT/EP2015/078005 filed on 30 Nov. 2015 entitled "NANOPARTICLES FOR ENCAPSULATING COMPOUNDS, THE PREPARATION AND USES THEREOF" in the name of Juan Manuel IRACHE GARRETA, et al., which claims priority to European Patent Application No. 14382486.0, filed on 1 Dec. 2014, both of which are hereby incorporated by reference herein in their entirety.

FIELD OF THE INVENTION

The present invention is encompassed in the pharmaceutical sector and in the nanotechnology sector and relates to encapsulation of active ingredients using nanoparticles of new polymer conjugates derived from the copolymer of methyl vinyl ether and maleic anhydride. The invention also relates to a process for producing both the conjugates and nanoparticles, to compositions containing said conjugates or nanoparticles, and applications thereof.

BACKGROUND OF THE INVENTION

A number of active ingredients (drugs), including many antitumor agents, are administered parenterally, which causes various problems. The increase in the quality of life of the patients as well as the reduction of healthcare costs should be emphasized among the main advantages that would be involved in the administration of antitumor agents by the oral route. This route of administration should allow a continuous exposure of cancer cells to the antitumor drug at a suitable and sustained concentration level, which can then improve the therapeutic index and reduce side effects.

When a drug is given orally, its bioavailability is generally low due to a number of factors such as solubility, stability within the gut, permeability, and first-pass metabolism:

- compounds with low solubility and low permeability present challenges in formulating oral dosage forms.
- the gastrointestinal tract is proving to be a difficult administration site because of the rapid turnover of mucus, and relatively constant transit time.
- drugs must pass through the intestinal wall and then the portal circulation to the liver; both sites are common sites of first-pass metabolism.
- the absorption of drugs can also be limited by efflux mechanisms, especially if compounds are of lipophilic nature. For example, the secretory transporter P-glycoprotein located on the mucosal surface of epithelial cells is responsible for the low and variable bioavailability of various drugs (e.g., paclitaxel, docetaxel or camptothecin).

These factors, that can be grouped into two interrelated categories, absorption (solubility and permeability) and metabolism, are to be considered when optimising oral bioavailability of drugs (Hayden Thomas et al., *Expert Opin Drug Metab Toxicol* 2006; 2(4):591-608).

One possible strategy to overcome the above mentioned drawbacks may be the use of polymeric nanoparticles as carriers for oral drug delivery. The encapsulation of drugs in nanoparticulate systems protects them against the harsh conditions of the gut, conducts the loaded drug till the surface of the absorptive cells, and controls their release. Bioadhesion has further improved drug administration There are several advantages in having bioadhesive drug delivery systems: (i) as a result of the adhesion, the formulation stays longer at the delivery site; (ii) by using specific bioadhesive molecules it will possible to target a particular site or tissue, for example, in the gastrointestinal (GI) tract; and (iii) increased residence time, if combined with controlled release of a drug, may lead to lower administration frequency (Woodley, *Clin Pharmacokinet* 2001; 40(2):77-84). However, for adequate bioadhesive properties, nanoparticles have to show muco-permeating properties in order to cross the mucus layer and, then, establish the adhesive interactions at the surface of the epithelium.

Many polymers have been described as useful materials to prepare bioadhesive nanoparticles for oral drug delivery, such as chitosan, polyvinyl alcohol (PVA), homo- and copolymers of lactic and glycolic acids (PLGA), or different copolymers between methyl vinyl ether and maleic anhydride (commercialized as Gantrez® from International Specialty Products ISP, USA).

The association or coating of nanoparticles with suitable hydrophilic compounds may change their physicochemical characteristics, and thus, modify their distribution and interaction with the biological medium, promoting the arrival of the encapsulated drug to its ideal site for action or absorption. A possible strategy is the use of polyethylene glycol (PEG) decorated-nanoparticles, named pegylated nanoparticles.

With respect to their use in oral administration, the association of polyethylene glycols to conventional nanoparticles minimise the interactions of these carriers with components of the lumen. This fact is related with the capability of PEGs of producing a hydrophilic corona around the nanoparticles and offering a slippery surface that prevents the interaction of proteins (Gref et al., *Science* 1994; 263:1600-1603) and facilitates the passage through the protective mucus layer of the gut mucosa.

The main drawback with this strategy is the stability of the association of polyethylene glycols to the surface of the nanoparticles (Peracchia et al., *Life Sci* 1997; 6:749-761). It is known that the ability of polyethylene glycol to reject proteins depends on the configuration, charge, length and flexibility of the polymer chains (Torchillin, *J Microencapsul* 1998; 15:1-19). The process for modifying the surface of the nanoparticles is mainly carried out by physical adsorption (Stolnik et al., *Adv Drug Del Rev* 1995; 16:195-214) or by covalent binding in the form of diblocks or triblocks (De Jaeghere et al., *J Drug Target* 2000; 8:143-153). Given that covalent binding is preferable, most pegylated nanoparticles have been prepared using polyethylene glycol copolymers with lactic or glycolic acid. However, this copolymerization process requires the use of several catalysts and specific chemical conditions (Beletsi et al., *Int. J. Pharm* 1999; 182:187-197). Furthermore, the toxic organic solvent residues used in the organic synthesis (methylene chloride, toluene, etc.), may be problematic.

Modification of surface nanoparticles of poly (methyl vinyl ether-co-maleic anhydride) (PVM/MA) with polyethylene glycols has also been achieved. Patent WO2005/104648 describes two different processes for obtaining pegylated nanoparticles: (i) simultaneous incubation of the polymer PVM/MA and the polyethylene glycol in an organic solvent, prior to desolvating the polymer and (ii) incubation of the biodegradable polymer nanoparticles with an aqueous solution of polyethylene glycol. Both processes are valid for preparing PVM/MA nanoparticles with polyethylene glycol associated to their surface, however the main drawback of simple adsorption is the quick loss of the coating layer in vivo (Neal et al., *J Pharm Sci* 1998; 87:242-1248) due to the inestability of the interaction.

WO2005/104648 also discloses pegylated nanoparticles of PVM/MA having superior intestinal adhesion characteristics as compared with nanoparticles of PVM/MA lacking polyethylene glycol. These nanoparticles have demonstrated a high versatility for encapsulating biologically active molecules. For example, WO2009/121997 discloses that modification and coating of the nanoparticles of PVM/MA with a polyethylene glycol allows obtaining pegylated nanoparticles capable of encapsulating considerable amounts of chemical synthesis drugs. However the stability of the coating is low and the coating layer may be lost with time.

Although bioadhesive drug delivery systems may provide an enhanced gastrointestinal transit time through adhesion to the gastrointestinal mucosal surface, good adhesion and delayed transit do not always translate into improved bioavailability (Davis SS. *Drug Discovery Today* 2005; 10(4): 249-257). If the drug does not dissolve readily or cannot penetrate the epithelial membrane due to efflux mechanisms, time at the absorption site may be insufficient. WO2008/129106 discloses alternative nanoparticles for drug administration comprising PVM/MA and a cyclodextrin that can increase, when administered orally, the bioavailability of drugs that are substrate of P-glycoprotein.

Nevertheless, there is still necessity of improving bioavailability of some drugs after oral administration. Hence, a lot of effort is still required to develop new drug administration systems (e.g. synthesize new polymers and co-polymers) to match the hydrophilic/hydrophobic properties of several drugs together with good physicochemical properties (degradability, stability and mechanic force) and improved pharmaceutical characteristics (distribution, bioadhesion and release rate) of nanoparticles made of those new polymers. These would allow increased absorption efficiency of drugs, enabling alternative treatments to hospital perfusion, allowing a reduction of the healthcare cost of treatments with this type of drugs and improving the quality of life of the patient.

SUMMARY OF THE INVENTION

The object of the present invention is to develop new drug administration systems which are stable within the GI tract, can encapsulate considerable amounts of biologically active compounds (e.g., drugs or active ingredients, particularly hydrophobic drugs), and increase the bioavailability of orally administered drugs, i.e., to provide new polymer conjugates and nanoparticles made thereof which solve the previously mentioned drawbacks.

The work leading to this invention has received funding from the European Union's Seventh Framework Programme (FP7/2007-2013) under grant agreement n° NMP4-LA-2011-280761.

It has been observed that new ester polymer conjugates of PVM/MA with a polyethylene glycol or a polyethylene glycol derivative containing a hydroxyl-terminal reactive group may be synthesized by a simple reaction, and results suitable to easily produce nanoparticles with good characteristics for the administration of biologically active compounds. It has especially been found that nanoparticles formed by these new ester polymer conjugates of PVM/MA with a polyethylene glycol or derivative thereof containing a hydroxyl-terminal reactive group are capable of i) encapsulating considerable amounts of biologically active compounds (e.g. paclitaxel, docetaxel and campthotecin), and ii) crossing the mucus layer and interact in an intimate way with the surface of the enterocytes (improving the absorption of the drug).

Surprisingly, the nanoparticles provided by this invention allow an increased bioavailability of said biologically active compounds through the intestinal mucosa obtaining extended and sustained plasma levels thereof for very long time periods (e.g., at least 72 hours in the case of docetaxel), which enables alternative administration to hospital perfusion, allowing a reduction of the healthcare cost of treatments with this type of drug and an improvement in the quality of life of the patient.

Therefore, in a first aspect, the invention relates to a new ester polymer conjugate of PVM/MA with a hydroxyl-terminated molecule, wherein said hydroxyl-terminated molecule is selected from between a polyethylene glycol and a derivative thereof containing a hydroxyl-terminal reactive group.

In one particular variant of the invention, the hydroxyl-terminated molecule is a polyethylene glycol that is not branched and does not have substituted hydroxyl groups. In this variant of the invention, the polyethylene glycols used preferably have a molecular weight comprised in the range from 400 to 35,000 Da; in a more particular embodiment the polyethylene glycol is selected from the group consisting of polyethylene glycol 1,000 (PEG1), polyethylene glycol 2,000 (PEG2), polyethylene glycol 6,000 (PEG6) and polyethylene glycol 10,000 (PEG10).

In another particular variant of the invention the polyethylene glycol has one substituted hydroxyl group. In this variant of the invention, the hydroxyl-terminated molecule is therefore a polyethylene glycol derivative containing a hydroxyl-terminal reactive group, preferably is a polyoxyethylene alkyl ether. In a more particular embodiment, the polyoxyethylene alkyl ether is a polyethylene glycol methyl ether (mPEG), and may be selected from the group consisting of metoxi-polyethylene glycol 1,000 (mPEG1), metoxi-polyethylene glycol 2,000 (mPEG2), metoxi-polyethylene glycol 6,000 (mPEG6) and metoxi-polyethylene glycol 10,000 (mPEG10).

In another aspect, the invention relates to a process for producing an ester polymer conjugate of PVM/MA with a hydroxyl-terminated molecule, wherein said hydroxyl-terminated molecule is selected from between a polyethylene glycol and a derivative thereof containing a hydroxyl-terminal reactive group, which comprises the steps of:

a) reacting the PVM/MA with the hydroxyl-terminated molecule of the invention in an organic solvent, and b) removing the organic solvent.

Said process of the invention is simple and applicable at an industrial scale. In one preferred variant of the invention, said process comprises an additional step c) of purifying the ester polymer conjugate.

In a particular embodiment, the weight ratio between the PVM/MA and the hydroxyl-terminated molecule in the solution of step a) is 1:0.01-0.25, preferably 1:0.015-0.2, more preferably 1:0.05-0.125.

In another aspect, the invention relates to an ester polymer conjugate obtained by said process of the invention.

In another aspect, the invention relates to the use of an ester polymer conjugate of the invention or obtained by a process of the invention, in the preparation of polymeric nanoparticles for drug delivery; preferably oral drug delivery.

In another aspect, the invention relates to a composition comprising i) an ester polymer conjugate of the invention or an ester polymer conjugate obtained by a process of the invention, and ii) a carrier; and to said composition of the invention for use in drug delivery; preferably oral drug delivery.

In yet another aspect, the invention relates to a nanoparticle comprising i) a matrix of an ester polymer conjugate according to the invention, or an ester polymer conjugate obtained by the process of the invention, and ii) a biologically active compound. In a particular embodiment, the biologically active compound is an antitumor agent. In a more particular embodiment, the antitumor agent is selected from the group consisting of docetaxel, camptothecin and paclitaxel; preferably the antitumor agent is docetaxel.

In a further aspect, the invention relates to a process for producing a nanoparticle according to the invention comprising the steps of:
a) mixing an ester polymer conjugate of the invention with the biologically active compound in an organic medium, and
b) desolvating the ester polymer conjugate by means of adding alcohol and water in the presence of a divalent metal.

Preferably, step a) is performed by means of mixing (i) an organic solution containing the ester polymer conjugate of the invention with (ii) an organic solution or dispersion of the biologically active compound.

Preferably, step b) is performed by means of adding a hydroalcoholic mixture comprising a divalent metal to the mixture obtained in step a).

In a particular embodiment the divalent metal is selected from the group consisting of calcium, magnesium, zinc, iron in divalent form, and combinations thereof; preferably the divalent metal is calcium.

In further particular embodiment, the weight ratio between the ester polymer conjugate of the invention and the biologically active compound in the mixture of step a) is 1:0.01-0.20, preferably 1:0.02-0.15, more preferably 1:0.03-0.10.

In one variant of the invention, said process for producing a nanoparticle according to the invention comprises an additional step c) of removing the organic medium, and/or optionally purifying; for example it can be made by filtration techniques or centrifugation until a pellet is obtained. Likewise, if desired, said process for producing a nanoparticle according to the invention can further comprises an additional step d) of drying the formed nanoparticles, optionally in the presence of a protective agent. In a particular embodiment of the invention, this additional step d) is made by means of spray-drying or freeze-drying.

Related to this, in another aspect the invention relates to a nanoparticle obtained by said process of the invention.

In another aspect, the invention relates to a nanoparticle according to the invention or a nanoparticle obtained by a process of the invention for use in medicine.

In another aspect, the invention relates to the use of a nanoparticle according to the invention or the use of nanoparticle obtained by a process of the invention in the manufacture of a pharmaceutical composition.

In yet another aspect, the invention relates to a pharmaceutical composition comprising i) at least one nanoparticle according to the invention, or at least one nanoparticle obtained by a process of the invention, and ii) a pharmaceutically acceptable carrier or vehicle. In a particular embodiment, said carrier or vehicle comprises a pharmaceutical excipient, acceptable for the administration thereof by oral route.

In another aspect, the invention relates to said pharmaceutical composition of the invention for use in medicine.

In a particular embodiment, the pharmaceutical composition of the invention comprises an antitumor agent. Therefore, in another aspect the invention relates to said pharmaceutical composition of the invention comprising an antitumor agent for use in a method of prevention or treatment of cancer; or alternatively, the invention also relates to the use of a pharmaceutical composition of the invention comprising an antitumor agent in the preparation of a medicament for the prevention or treatment of cancer.

In a more particular embodiment the pharmaceutical composition is selected from the group consisting of:
a pharmaceutical composition comprising:
 a) an ester polymer conjugate of PVM/MA with polyethylene glycol 2,000 from 38% to 47%,
 b) docetaxel from 3% to 5%,
 c) calcium from 0.1% to 0.2%, and
 d) a saccharide from 15% to 40%,
wherein all the proportions are by weight with respect to the total weight of the composition;
a pharmaceutical composition comprising:
 a) an ester polymer conjugate of PVM/MA with metoxi-polyethylene glycol 2,000 from 38% to 47%,
 b) docetaxel from 3% to 5%,
 c) calcium from 0.1% to 0.2%, and
 d) a saccharide from 15% to 40%,
wherein all the proportions are by weight with respect to the total weight of the composition; and
a pharmaceutical composition comprising:
 a) an ester polymer conjugate of PVM/MA with metoxi-polyethylene glycol 2,000 from 30% to 40%,
 b) camptothecin from 0.08% to 1.5%,
 c) calcium from 0.10% to 0.20%, and
 d) a saccharide from 15% to 40%,
wherein all the proportions are by weight with respect to the total weight of the composition.

DETAILED DESCRIPTION OF THE INVENTION

Figure 1:
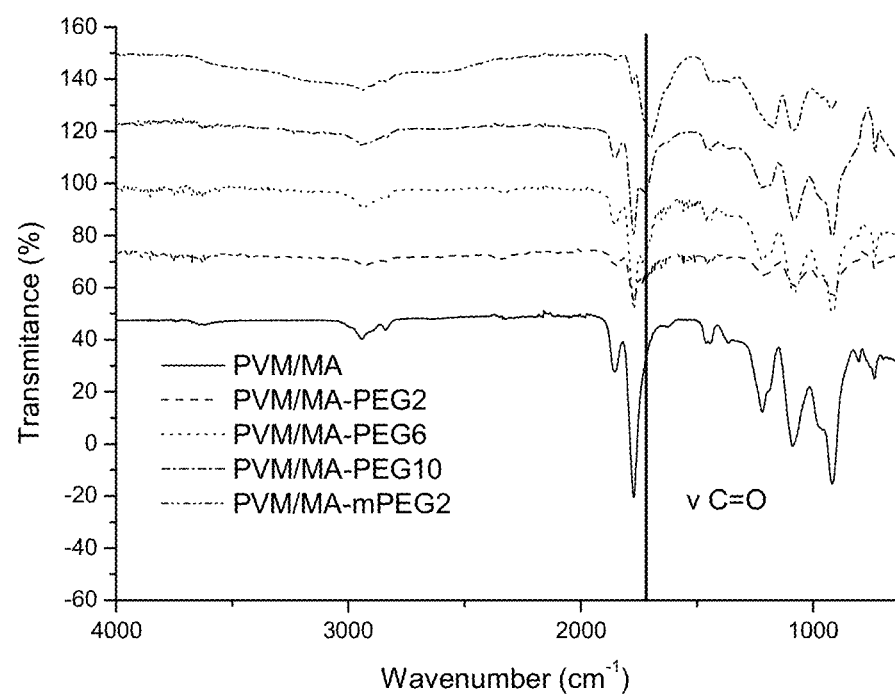
FIG. 1. Infrared spectra of the PVM/MA and ester polymer conjugates of the PVM/MA with polyethylene glycol 2,000 (PVM/MA-PEG2), polyethylene glycol 6,000 (PVM/MA-PEG6), polyethylene glycol 10,000 (PVM/MA-PEG10), and methoxy polyethylene glycol 2,000 (PVM/MA-mPEG2).
Figure 2A:
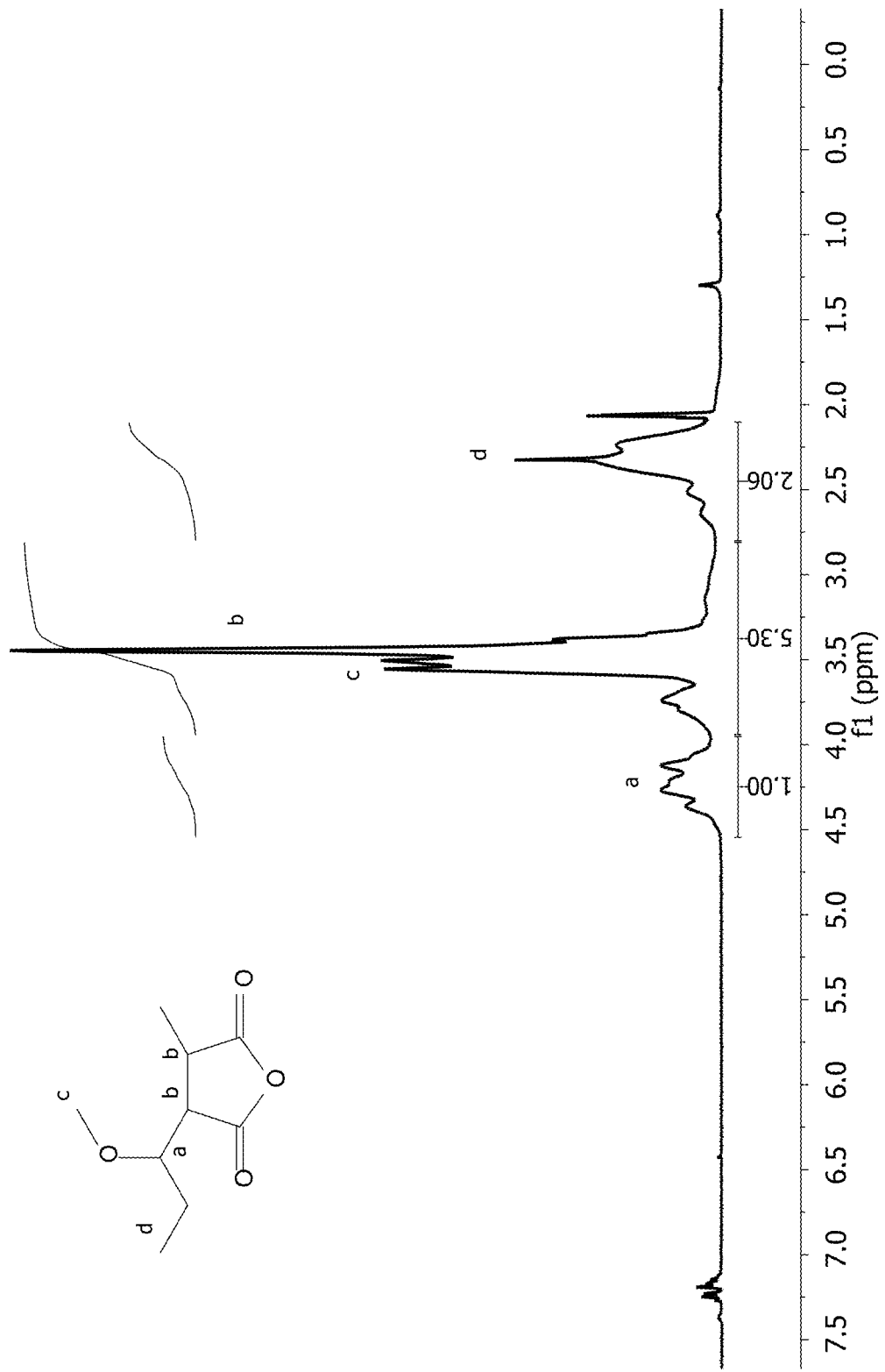
FIG. 2. $^1$H-NMR spectra of A) PVM/MA; and of ester polymer conjugates of PVM/MA with B) polyethylene glycol 2,000 (PVM/MA-PEG2), C) polyethylene glycol 6,000 (PVM/MA-PEG6), D) polyethylene glycol 10,000 (PVM/MA-PEG10), and E) methoxy polyethylene glycol 2,000 (PVM/MA-mPEG2).
Figure 2B:
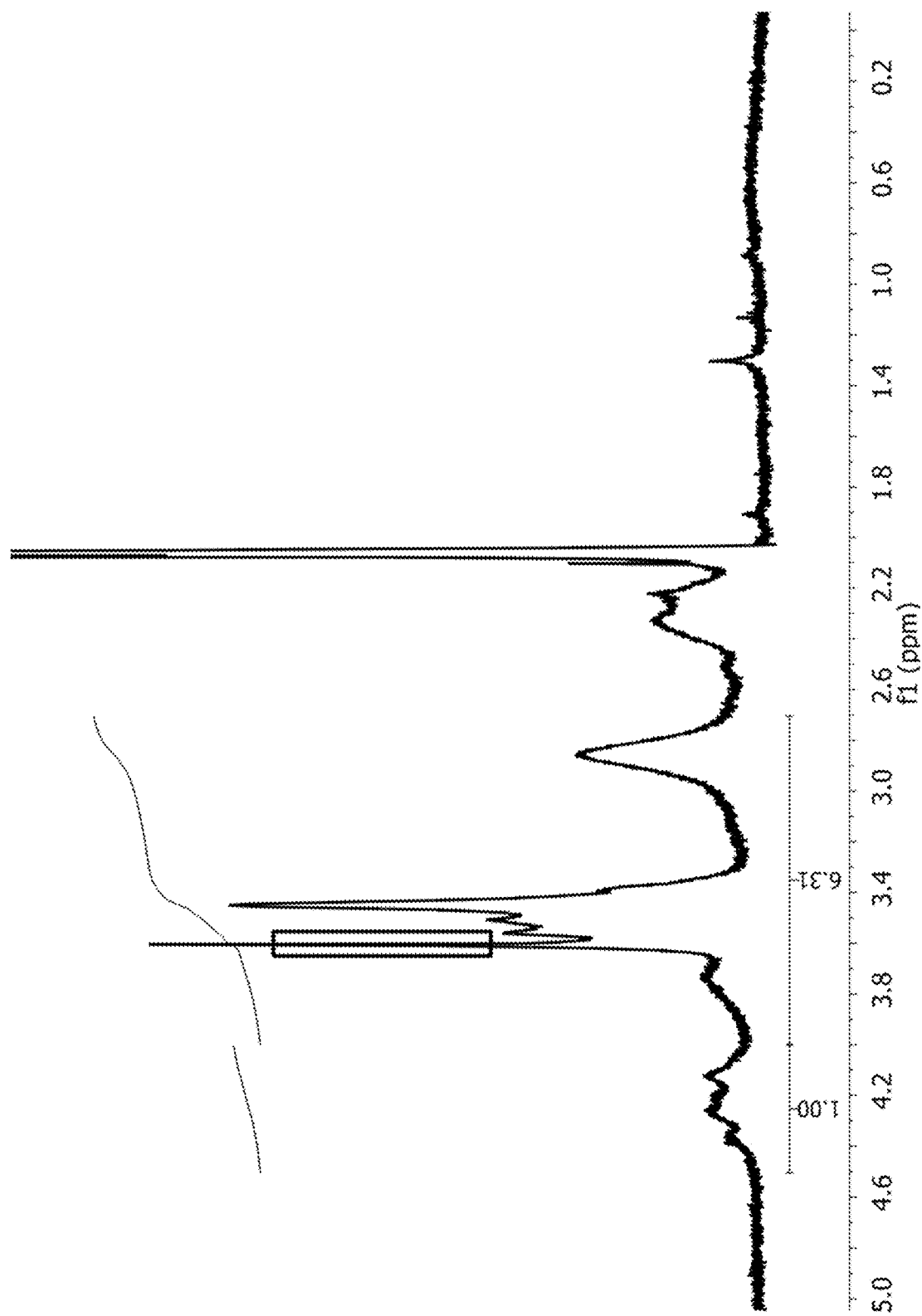
Figure 2C:
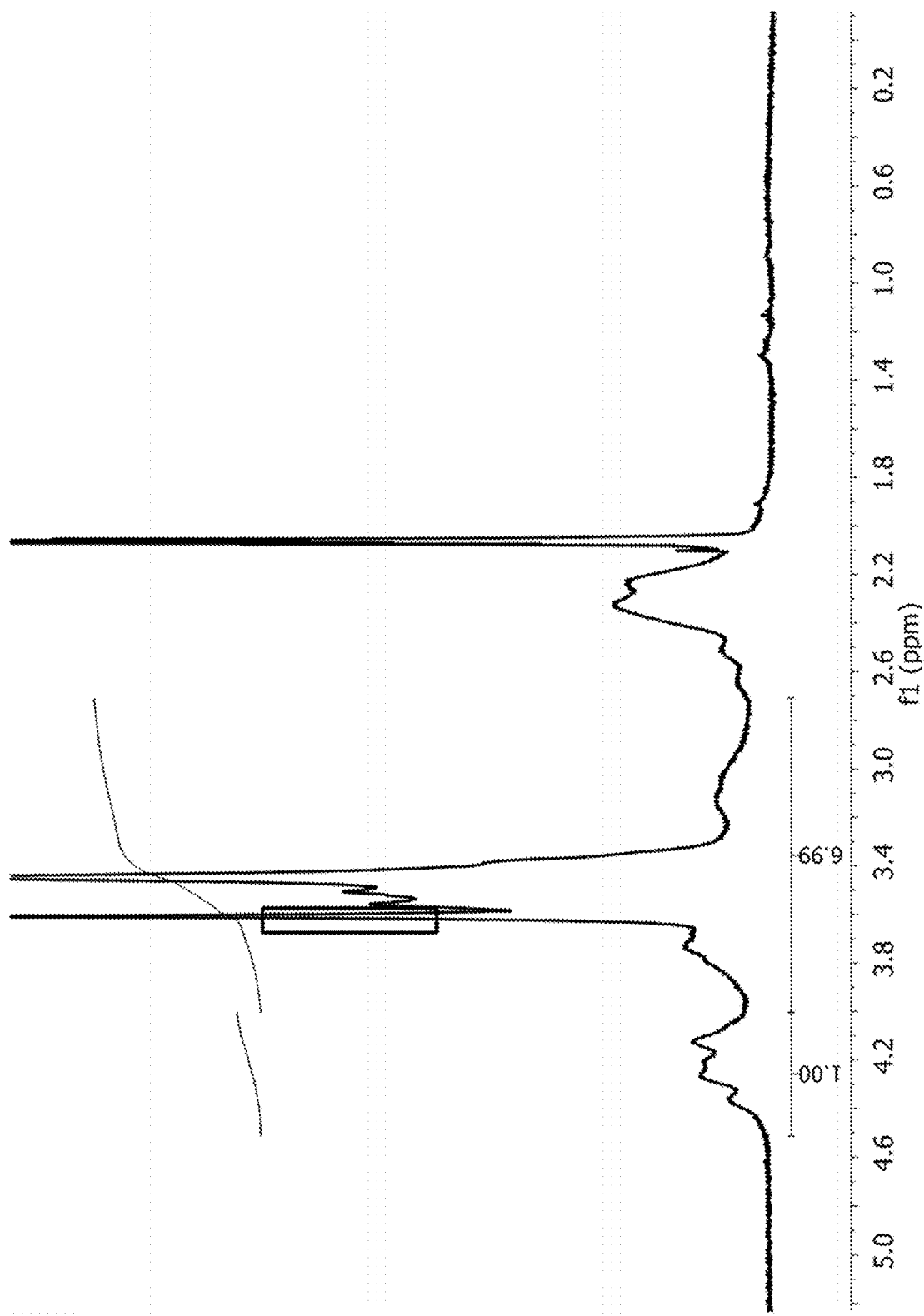
Figure 2D:
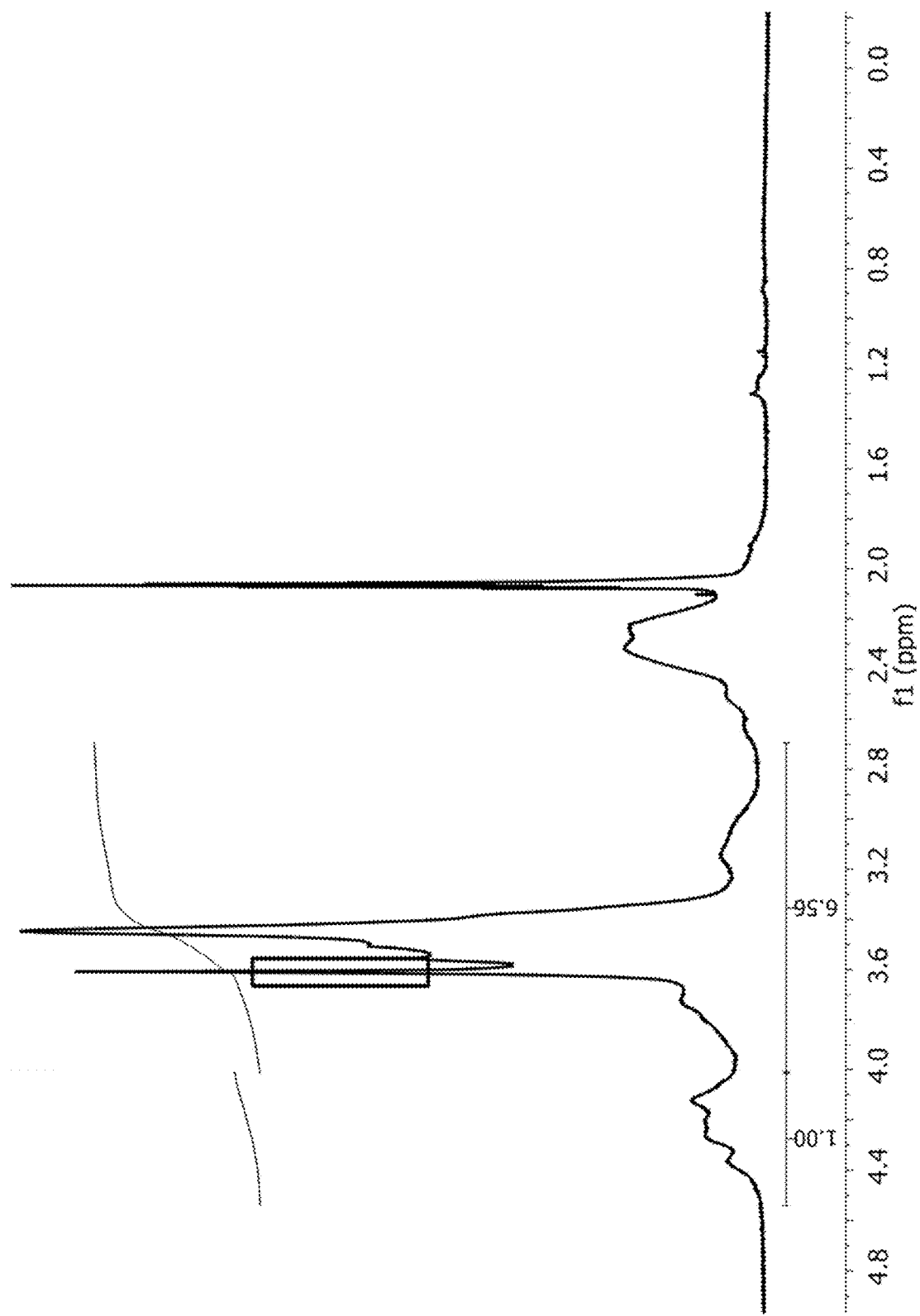
Figure 2E:
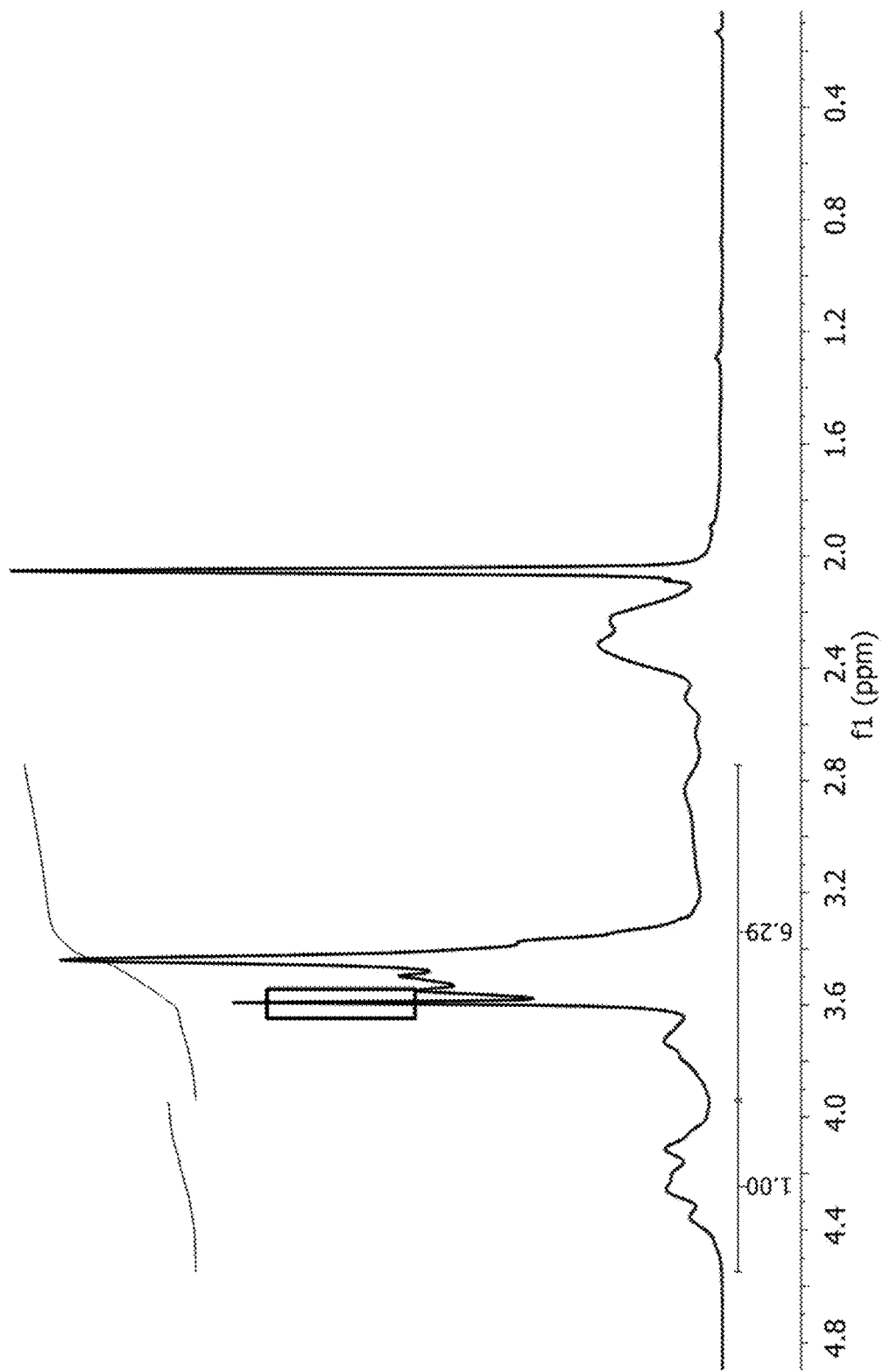

The present invention provides new drug administration systems (new polymer conjugates and nanoparticles made thereof) which, can encapsulate considerable amounts of biologically active compounds, are stable within the GI tract and increase the bioavailability of orally administered drugs.

It has surprisingly been found that new ester polymer conjugates of PVM/MA with a polyethylene glycol (or derivative thereof containing a hydroxyl-terminal reactive group) may be synthesized by a simple reaction, and results suitable to easily produce nanoparticles with improved characteristics for the administration of biologically active compounds. It has especially been found that nanoparticles formed by these new ester polymer conjugates of PVM/MA with a polyethylene glycol (or derivative thereof containing a hydroxyl-terminal reactive group) are capable of encapsulating considerable amounts of biologically active compounds and increase their oral bioavailability.

Definitions

For the purpose of facilitating the comprehension of the present invention, the meaning of some terms and expressions as used in the context of the invention are set forth below.

As it is used herein, "poly (methyl vinyl ether-co-maleic anhydride)" (PVM/MA) refers to the copolymer of methyl vinyl ether and maleic anhydride (commercialized by International Specialty Products, ISP, under trademark Gantrez® AN). Therefore expressions, "PVM/MA", poly(anhydride), or Gantrez® AN are synonyms, and are indistinctly used in this description. Gantrez® AN copolymer contains alternating units of methylvinylether and maleic anhydride, having the formula:

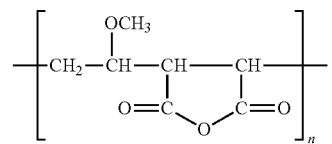

The fundamental character of this polymerization requires that a maleic anhydride unit must be adjacent to a methylvinylether unit and vice versa, resulting in a true alternating copolymer. The anhydride groups in Gantrez® AN structure allows the chemical interaction of this polymer with hydroxyl containing molecules through a nucleophilic substitution reaction mechanism.

Gantrez® AN copolymer is supplied as a water-insoluble white powder, and is widely employed for pharmaceutical and medical purposes, as denture adhesives, thickening and suspending agents and as adjuvants for the preparation of transdermal patches. The oral toxicity of this copolymer is quite low ($LD_{50}$ in guinea pigs is about 8-9 g/kg) so it has also been used as material for the preparation of nanoparticulate carriers. In a particular embodiment of the invention, the PVM/MA copolymer has a molecular weight comprised in the range from 80 to 2,500 kDa, preferably from 85 to 2,000 kDa, more preferably from 90 to 220 kDa.

As it is used herein, "ester" refers to an ester (as of a PVM/MA) that contains at least one ester group (i.e. at least one anhydride unit of PVM/MA is esterified with a hydroxyl-terminated molecule). According to the present invention at least one anhydride unit of PVM/MA is esterified with a hydroxyl-terminated molecule selected from between a polyethylene glycol and a polyethylene glycol derivative containing a hydroxyl-terminal reactive group. Illustrative, non-limitative examples of esters of PVM/MA are those wherein the degree of substitution is at least 5%, 10%, 15%, 20%, 25%, 30%, 35%, 40%, 45%, 50%, 55%, 60%, 65%, 70%, 75%, 80%, 85%, 90% or 95%.

As it is used herein "degree of esterification" (DE) or "degree of substitution" (DS) of the ester polymer conjugate of the invention is defined as the percentage of anhydride units that are esterified with a hydroxyl-terminated molecule according to the present invention, i.e. the percentage of ester bounds that are formed. In a particular embodiment, the degree of esterification can be measured by standard processes known by the person skilled in the art, and which are described, by way of illustration, in the experimental part attached to the examples described below.

As it is used herein a "hydroxyl-terminated molecule" is a molecule with at least one primary hydroxy (—OH) group. According to the present invention, said hydroxyl-terminated molecule is selected from between a polyethylene glycol and a polyethylene glycol derivative containing a hydroxyl-terminal reactive group, as following defined.

In the present description, the term "polyethylene glycol" (PEG), is understood to be any hydrophilic polymer soluble in water containing ether groups linked by 2 carbon atoms, optionally branched ethylene groups. Therefore this definition includes branched or non-branched polyethylene glycols.

PEG is also known as polyethylene oxide (PEO) or polyoxyethylene (POE) (the three names are chemically synonymous and refers to an oligomer or polymer of ethylene oxide). The term also includes derivatives of one of the terminal hydroxyl groups, which can be modified (one of two ends). Thus, according to the present invention polyethylene glycol derivatives maintaining one primary hydroxy (—OH) group can be used.

Polyethylene glycols are water-soluble polymers that have been approved (FDA) for the oral, parenteral and topical administration of drugs. Polyethylene glycols are produced by means of polymerization of ethylene oxide (EO) in the presence of water, monoethylene glycol or diethylene glycol as reaction initiators in an alkaline medium (1,2-Epoxide Polymers: Ethylene Oxide Polymers and Copolymers" in Encyclopedia of Polymer Science and Engineering; Mark, H. F. (Ed.), John Wiley and Sons Inc., 1986, pp. 225-273). When the desired molecular weight (generally controlled by means of in-process measurements of viscosity) is reached, the polymerization reaction ends by neutralizing the catalyst with an acid (lactic acid, acetic acid or the like). The result is a linear polymer having a very simple structure:

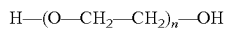

where (n) is the number of EO monomers or units. This term polyethylene glycol is normally used to indicate the significant influence of hydroxyl terminal groups on the physicochemical properties of these molecules. The term PEG is normally used in combination with a numerical value. In the pharmaceutical industry the number indicates the mean molecular weight, whereas in the cosmetic industry the number accompanying the letters PEG refers to the polymerized EO units forming the molecule (Handbook of Pharmaceutical Excipients, Rowev R. C., Sheskey P. J., Weller P. J. (Eds.), 4th Edition, Pharmaceutical Press and American Pharmaceutical Association, London, UK, 2003). PEGs are included in various pharmacopeias, although the nomenclature differs (International Harmonisation: Polyethylene glycol (PEG): Pharmeuropa 1999, 11, 612-614). According to the Handbook of Pharmaceutical Excipients (Fourth Edition), 2003 Edited by R. C. Rowe, P. J. Sheskey and P. J. Weller Published by the Pharmaceutical Press (London, UK) and the American Pharmaceutical Association (Washington, USA), polyoxyethylene glycols are also referred to as polyethylene glycols, macrogols, or PEG. The British and European Pharmacopoeias use polyethylene glycols and macrogols, while the US pharmacopoeia (USP) uses polyethylene glycols.

In one variant of the invention the polyethylene glycols used preferably have a molecular weight comprised in the range from 400 to 35,000 Da. In one preferred variant of the invention the polyethylene glycol used has a molecular weight equal to or greater than 400, more preferably equal to or greater than 1,000; values comprised from 1,000 to 20,000 are especially preferred, more preferably from 2,000 to 10,000 Da. Illustrative non-limiting examples of PEG which can be used in the present invention include polyethylene glycol 1,000, polyethylene glycol 2,000, polyethylene glycol 6,000 or polyethylene glycol 10,000 (PEG1, PEG2, PEG6 or PEG10 respectively).

PEGS with molecular weight less than 400 are non-volatile liquids at room temperature. PEG600 shows a melting point comprised between 17 and 22° C., whereas PEGs with mean molecular weights comprised between 800 and 2,000 are pasty materials with low melting points. Above a molecular weight of 3,000 Da PEGs are solid, and up to PEG 35,000 are commercially available. On the other hand, although the melting point of PEGs increases when the molecular weight increases, the boiling point increases up to a maximum value of 60° C. Likewise, when the molecular weight increases, its aqueous solubility decreases. In any case, for PEG 35,000 an amount close to 50% w/v can be dissolved in water.

From a toxicological point of view, PEGs are considered rather non-toxic and non-immunogenic (Hermansky S. J et al., *Food Chem Toxic.*, 1995, 33, 139-140; Final Report on the Safety Assessment of PEGs: J. A. C. T., 1993, 12, 429-457; Polyethylene glycol, 21 CFR 172.820, FDA). The maximum daily intake defined by the WHO is 10 mg/kg (Polyethylene glycols; Twenty-third report of the Joint FAO/WHO Expert Committee on Food Additives; World Health Organisation, Geneva; Technical Report Series 1980, 648, 17-18).

Polyethylene glycol derivatives have advantageous features that are similar to traditional PEGs such as their aqueous solubility, physiological inactivity, low toxicity and stability under very different conditions. These derivatives include very different products and are characterized by the functional group substituting the primary hydroxyl. According to the present invention, polyethylene glycol derivatives containing a hydroxyl-terminal reactive group can be used.

In a particular embodiment, said polyethylene glycol derivative containing a hydroxyl-terminal reactive group is a polyoxyethylene alkyl ether. Polyoxyethylene alkyl ethers compounds have the general formula $H_{(2m+1)}C_m(O-CH_2-CH_2)nOH$. They will be referred as CmEn with m indicating the number of carbons in the alkyl chain and n being the number of ethylene oxide units in the hydrophilic moiety. Illustrative, non-limiting examples are: polyethylene glycol methyl ethers, also known as methoxy polyethylene glycols (mPEG); polyethylene glycol ethyl ethers; polyethylene glycol propyl ethers; and, polyethylene glycol buthyl ethers.

The chemical structures of some polyoxyethylene alkyl ethers corresponding to the aforementioned groups are indicated below in an illustrative manner:

a) $H_3C(O-CH_2-CH_2)_nOH$
b) $H_5C_2(O-CH_2-CH_2)_nOH$
   $H_7C_3(O-CH_2-CH_2)_nOH$
d) $H_9C_4(O-CH_2-CH_2)_nOH$

Non-limiting examples of polyoxyethylene alkyl ethers which can be used in the present invention include the methyl ether of polyethylene glycol 1,000 or metoxi-polyethylene glycol 1,000 (mPEG1); the methyl ether of polyethylene glycol 2,000 or metoxi-polyethylene glycol 2,000 (mPEG2); the methyl ether of polyethylene glycol 6,000 or metoxi-polyethylene glycol 6,000 (mPEG6); the methyl ether of polyethylene glycol 10,000 or metoxi-polyethylene glycol 10,000 (mPEG10).

The following can also be pointed out among polyethylene glycols derivatives containing a hydroxyl-terminal reactive group that can be used in the present invention:

Poly(ethylene glycol) methacrylate
Poly(ethylene glycol) acrylate
Poly(ethylene glycol) monolaurate
Poly(ethylene glycol) monooleate
Poly(ethylene glycol) (12) tridecyl ether
Poly(ethylene glycol) tetrahydrofurfuryl ether The election of the polyethylene glycols and derivatives allows modulating the characteristics of the generated system and the use of mixtures of them adds one more variability factor. From the practical point of view, it is important to adapt and select the most suitable system for each active molecule and for each route of administration.

As it is used herein "molecular weight" is defined as the average molar mass of a molecule. Unlike small molecules, the molecular weight of a polymer is not one unique value. Rather, a given polymer will have a distribution of molecular weights depending for example on the way the polymer is produced. Therefore, as it is used herein, the term molecular weight for polymers refers to the distribution of molecular weight, or of the average molecular weight. There are many ways, however, to calculate the average molecular weight. According to the present invention, the average molecular weight of pre-formed ester polymers of the invention is determined by $^1$H-NMR, and the average molecular weight of commercial PVM/MA is determined by SEC-MALLS, as described, by way of illustration, in the experimental part attached to the examples described below.

As it is used herein, "nanoparticle" refers to spherical type or similar shaped colloidal systems (nanocapsule or nanosphere) with a size less than 1 micrometer (µm), preferably in the range from 10 to 900 nanometers (nm).

As used herein, the term "biologically active compound" (BAC) relates to any small molecule (e.g., a drug or active ingredient of a medicament) or derivative thereof which is administered to a subject, preferably a human being, with prophylactic or therapeutic purposes; i.e., any substance or chemical compound with a molecular weight below 900 Daltons which can be used in the treatment, cure, prevention or diagnosis of a disease or to improve the physical and mental wellbeing of humans and animals. As used herein, the term "derivative", applied to a biologically active compound, includes prodrugs and analogs of said biologically active compound.

As used herein, terms "antitumor agent", "anticancer agent" or "antineoplastic agent" (indistinctly used in this description), generally refers to substances which inhibit or suppress the growth and proliferation of cancer cells. Antitumor agents may also include compounds that destroy cancer cells or interfere with cell division, compounds that block certain hormones involved in cancer, compounds that inhibit or prevent the growth of new blood vessels (e.g. angiogenesis inhibitors), agents that damage DNA (e.g. alkylating agents, such as cisplatin, carboplatin, and oxaloplatin; anti-metabolites; and topoisomerase inhibitors), and compounds with anticancer properties (e.g., taxanes, vinca alkaloids, and plant alkaloids). The term "antitumor agent" also includes radiation therapy. An antitumor agent may also include an agent specific for deregulated proteins of cancer cells, such as an inhibitor of receptor tyrosine kinases.

As it is used herein, a "divalent metal" includes any metal element the valence of which is 2, for example, an alkaline-earth metal, e.g., calcium, magnesium, zinc, etc., or, if it has several valences, one of them is 2, for example, iron, etc., on the proviso that it is pharmaceutically acceptable.

As it is used herein, "mean size" refers to the average diameter of the nanoparticle population that moves together in an aqueous medium. The mean size of these systems can be measured by standard processes known by the person skilled in the art, and which are described, by way of illustration, in the experimental part attached to the examples described below. The mean size of the particles can be mainly affected by the amount and molecular weight of the PVM/MA, by the nature and amount of the hydroxyl-terminated molecule of the invention, by the nature and amount of the biologically active molecule present in the nanoparticles of the invention (generally, the larger the amount or molecular weight of said components, the larger the average size of the nanoparticle), and by some parameters of the process for the production of said nanoparticles. The nanoparticles of the invention are characterized by having a mean particle size less than 1 µm, typically comprised in the range from 1 to 999 nm, preferably from 10 to 900 nm, more preferably from 100 to 500 nm, still more preferably from 150 to 400 nm. In a particular embodiment, the nanoparticles of the invention have a mean particle size about 250 nm approximately.

As it is used herein, the term "pharmaceutically acceptable" means that a compound or combination of compounds is sufficiently compatible with the other ingredients of a formulation, and not deleterious to the subject up to those levels acceptable by the industry standards.

As it is used herein, the term "carrier" refers to a diluent with which the active ingredient or drug is administered. Examples of pharmaceutically acceptable carriers are known in the state of the art and include phosphate buffered saline solutions, water, emulsions, such as oil/water emulsions, different types of wetting agents, sterile solutions, etc. Suitable pharmaceutical carriers are described in "Remington's Pharmaceutical Sciences" by E. W. Martin, 1995. Preferably, the carriers of the invention are approved by a regulatory agency of the Federal or a state government or listed in the United States Pharmacopoeia or another generally recognized pharmacopeia for use in animals, and more particularly in humans.

As it is used herein, the term "preventing" refers to keep from happening, existing, or alternatively delaying the onset or recurrence of a disease, disorder, or condition to which such term applies, or of one or more symptoms associated with a disease, disorder, or condition. The term "prevention" refers to the act of preventing, as "preventing" is defined immediately above.

As it is used herein, the term "treating", refers to reversing, alleviating, or inhibiting the progress of the disorder or condition to which such term applies, or one or more symptoms of such disorders or condition. The term "treatment" refers to the act of treating, as "treating" is defined immediately above.

As it is used herein, the term "subject" means animals, in particular mammals such as dogs, cats, cows, horses, sheep, geese, and humans. Particularly preferred subjects are humans of both sexes.

Ester Polymer Conjugates of Poly (Methyl Vinyl Ether-Co-Maleic Anhydride)

The present invention provides new ester polymer conjugates of poly (methyl vinyl ether-co-maleic anhydride) (PVM/MA) with hydroxyl-terminated molecules. Terms "ester", "poly (methyl vinyl ether-co-maleic anhydride)" and "hydroxyl-terminated molecule", as used herein, have been previously defined, and are incorporated herein by reference. Thus, according to the present invention, at least one anhydride unit of PVM/MA polymer is esterified with a hydroxyl-terminated molecule selected from between: a polyethylene glycol and a polyethylene glycol derivative containing a hydroxyl-terminal reactive group, hereinafter "hydroxyl-terminated molecule of the invention".

Therefore, in a first aspect, the invention relates to an ester polymer conjugate of PVM/MA with a hydroxyl-terminated molecule, wherein said hydroxyl-terminated molecule is selected from between a polyethylene glycol and a derivative thereof containing a hydroxyl-terminal reactive group, hereinafter "ester polymer conjugate of the invention".

In a particular embodiment, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of anhydride units of PVM/MA polymer are esterified with the hydroxyl-terminated molecule of the invention. For example, a degree of esterification of at least 5% provides good results.

In one variant of the invention, the hydroxyl-terminated molecule is a polyethylene glycol that is not branched and does not have substituted hydroxyl groups. In this variant of the invention, the polyethylene glycols used preferably have a molecular weight comprised in the range from 400 to 35,000 Da. In one preferred variant of the invention, the polyethylene glycol used has a molecular weight equal to or greater than 400, more preferably equal to or greater than 1,000; values comprised in the range from 1,000 to 20,000 are especially preferred, more preferably from 2,000 to 10,000 Da. In a more preferred variant of the invention, the hydroxyl-terminated molecule is a polyethylene glycol selected from the group consisting of polyethylene glycol 1,000 (PEG1), polyethylene glycol 2,000 (PEG2), polyethylene glycol 6,000 (PEG6) and polyethylene glycol 10,000 (PEG10).

In another variant, the hydroxyl-terminated molecule of the invention is a polyethylene glycol with one substituted hydroxyl group. In this variant of the invention, the hydroxyl-terminated molecule is therefore a polyethylene glycol derivative containing a hydroxyl-terminal reactive group, preferably is a polyoxyethylene alkyl ether. In a more particular embodiment, the polyoxyethylene alkyl ether is a polyethylene glycol methyl ether (mPEG). In a still more preferred embodiment, the polyethylene glycol methyl ether is selected from the group consisting of metoxi-polyethylene glycol 1,000 (mPEG1), metoxi-polyethylene glycol 2,000 (mPEG2), metoxi-polyethylene glycol 6,000 (mPEG6) and metoxi-polyethylene glycol 10,000 (mPEG10).

The average molecular weight of the ester polymer conjugate of the invention may vary within a broad range; however, in a particular embodiment, the ester polymer conjugate of the invention has an average molecular weight comprised in the range from 85 to 3,000 kDa, preferably from 90 to 2,500 kDa, more preferably from 95 to 250 kDa.

Process for Obtaining an Ester Polymer Conjugate of the Invention

In a second aspect, the invention relates to a process for producing an ester polymer conjugate of PVM/MA with a hydroxyl-terminated molecule, wherein said hydroxyl-terminated molecule is selected from between a polyethylene glycol and a derivative thereof containing a hydroxyl-terminal reactive group (i.e. the ester polymer conjugate of the invention), hereinafter referred to as "process [1] of the invention", which comprises the steps of:

a) reacting the PVM/MA with the hydroxyl-terminated molecule of the invention in an organic solvent, and
b) removing the organic solvent.

This step a) of the "process [1] of the invention" includes dissolving and incubating the PVM/MA, and the hydroxyl-terminated molecule of the invention in an organic solvent such as, for example, acetone, for the reaction to take place. The incubation of the mixture is preferably carried out under stirring at a temperature comprised in the range from 15° C. to 80° C., more preferably in the range from 45° C. to 65° C., most preferably at 55° C. The incubation time may vary from 1 to 24 h. In a particular preferred embodiment, the incubation is carried out for 2-4 h. For example, an incubation of the mixture at 55° C. for 3 h provides good results. Alternatively, it is also possible to react the PVM/MA and the hydroxyl-terminated molecule under stirring at room temperature (R/T) for longer periods of time (24-48 h).

The organic solvent is removed in step b) by any suitable process, such as evaporation under reduced pressure, evaporation at room temperature, or centrifugation under vacuum. In a particular embodiment, step b) comprises removing the organic solvent by evaporation under reduced pressure.

In one preferred embodiment, process [1] of the invention comprises an additional step c) of purifying the ester polymer conjugate of the invention. In one particular variant, additional step c) comprises several washes with a liquid in which polymer is insoluble (but not the unreacted hydroxyl-terminated molecule); and filtering under vacuum until no traces of unreacted hydroxyl-terminated molecule are detected in the liquid (for example measuring by thin layer chromatography, TLC). In a preferred variant, the washing liquid is a mixture of dichloromethane/methanol. For example, a mixture $CH_2Cl_2/CH_3OH$ (9:1) used as mobile phase, and iodine for revealing in TLC, provide good results.

The particulars of the hydroxyl-terminated molecule of the invention have been previously mentioned in the "Definitions" section, and also in connection with the ester polymer conjugate of the invention, and are incorporated herein by reference. According to these, in a particular embodiment of the process [1] of the invention, the hydroxyl-terminated molecule reacting with the PVM/MA in step a) is a polyethylene glycol; preferably a polyethylene glycol selected from the group consisting of polyethylene glycol 1,000 (PEG1), polyethylene glycol 2,000 (PEG2), polyethylene glycol 6,000 (PEG6), and polyethylene glycol 10,000 (PEG10). In another particular embodiment of the process [1] of the invention, the hydroxyl-terminated molecule reacting with the PVM/MA in step a) is a polyethylene glycol derivative containing a hydroxyl-terminal reactive group, preferably a polyoxyethylene alkyl ether; more preferably a polyethylene glycol methyl ether (mPEG); most preferably a polyethylene glycol methyl ether selected from the group consisting of metoxi-polyethylene glycol 1,000 (mPEG1), metoxi-polyethylene glycol 2,000 (mPEG2), metoxi-polyethylene glycol 6,000 (mPEG6) and metoxi-polyethylene glycol 10,000 (mPEG10).

The weight ratio between the PVM/MA and the hydroxyl-terminated molecule of the invention in the solution of step a) of the process [1] of the invention, may vary within a broad range; however, in a particular embodiment, the PVM/MA:hydroxyl-terminated molecule ratio by weight is comprised in the range from 1:0.01 to 1:0.25; preferably from 1:0.015 to 1:0.2; more preferably from 1:0.05 to 1:0.125. In a non-limiting illustrative manner, when the hydroxyl-terminated molecule is a polyethylene glycol, a weight ratio PVM/MA:PEG of 1:0.05, 1:0.1, 1:0.125, or 1:0.25 provides good results. In a similar way, when the hydroxyl-terminated molecule is a metoxi-polyethylene glycol, a weight ratio PVM/MA:mPEG of 1:0.01, 1:0.015, 1:0.025, 1:0.05, 1:0.01, or 1:0.2 provides good results.

In other words, the weight ratio between the hydroxyl-terminated molecule of the invention and the PVM/MA in the solution of step a) of the process [1] of the invention, is comprised in the range from 1:4 to 1:100; preferably from 1:5 to 1:66; more preferably from 1:8 to 1:20. In a non-limiting illustrative manner, when the hydroxyl-terminated molecule is a polyethylene glycol, a weight ratio PEG:PVM/MA of 1:4, 1:8, 1:10, or 1:20 provides good results. Similarly, when the hydroxyl-terminated molecule is a metoxi-polyethylene glycol, a weight ratio mPEG:PVM/MA of 1:5, 1:10, 1:20, 1:40, 1:66, or 1:100 provides good results.

The ester polymer conjugate obtained by process [1] of the invention, i.e., the ester polymer conjugate of PVM/MA with a hydroxyl-terminated molecule, wherein said hydroxyl-terminated molecule is selected from between a polyethylene glycol and a derivative thereof containing a hydroxyl-terminal reactive group, produced by means of a process which comprises: a) reacting the PVM/MA with the hydroxyl-terminated molecule of the invention in an organic solvent, and b) removing the organic solvent, forms an additional aspect of the present invention.

Applications of the Ester Polymer Conjugate of the Invention

Pre-formed ester polymer conjugates of the invention have shown good physicochemical and pharmacological properties, and may be used as starting materials in the formation of nanoparticles for the administration of biologically active compounds. Thus, in another aspect, the invention relates to the use of an ester polymer conjugate of the invention, or an ester polymer conjugate obtained by the process [1] of the invention, in the preparation of polymeric nanoparticles for drug delivery; preferably oral drug delivery.

In another aspect, the invention relates to a composition comprising i) an ester polymer conjugate of the invention or an ester polymer conjugate obtained by the process [1] of the invention, and ii) a carrier, hereinafter "composition [1] of the invention". In a particular embodiment the composition [1] of the invention comprises at least 2% concentration (w/v) of an ester polymer conjugate of the invention or of an ester polymer conjugate obtained by the process [1] of the invention.

As illustrative example, said composition [1] of the invention can be used as a basis for the manufacturing of nanoparticles for the administration of biologically active compounds. Thus, in yet another aspect, the invention relates to said composition [1] of the invention for use in drug delivery; preferably oral drug delivery.

Nanoparticle

In another aspect, the invention relates to a nanoparticle comprising a matrix of an ester polymer conjugate of the invention. The nanoparticles of the invention have the capacity to encapsulate a biologically active compound (BAC), and may be used as drug delivery system.

Thus, in a particular embodiment, optionally in combination with one or more features of the various embodiments described above or below, the nanoparticle further comprises a biologically active compound, hereinafter identified in this description as "nanoparticle of the invention".

The term "biologically active compound" (BAC) has been previously defined and refers to any small molecule (e.g., a drug or active ingredient of a medicament) or derivative thereof which is administered to a subject, preferably a human being, with prophylactic or therapeutic purposes; i.e., any substance or chemical compound with a molecular weight below 900 Daltons which can be used in the treatment, cure, prevention, or diagnosis of a disease, or to improve the physical and mental wellbeing of humans and animals. As used herein, the term "derivative", applied to a small molecule, includes prodrugs and analogs of said molecule.

The BAC can be selected from a variety of known classes of drugs, including, for example: antitumor or antineoplastic agents, analgesics agents, anesthetics agents, antiinflammatory agents, antiarrhythmic agents, antihypertensive agents, antianginal agents, antiasthma agents, antibiotics (including penicillins), anticoagulants agents, antidepressants agents, antipsycothic agents, antidiabetic agents, antiepileptics, antihistamines, antitussives, antimuscarinic agents, antimycobacterial agents, antioxidant agents, antipyretics, immunosuppressants, immunostimulants, antithyroid agents, anthelmintics, antiviral agents, antibacterial agents, antifungal agents, anxiolytic sedatives (hypnotics and neuroleptics) agents, astringents, bacteriostatic agents, beta-adrenoceptor blocking agents, blood products and substitutes, bronchodilators, buffering agents, cardiac inotropic agents, chemotherapeutics, contrast media, corticosteroids, cough suppressants (expectorants and mucolytics), diagnostic agents, diagnostic imaging agents, diuretics, dopaminergics (antiparkinsonian agents), etc. The nanoparticles of the invention can incorporate one or more of said BAC.

Examples of BAC according to the present invention are docetaxel, paclitaxel, camptothecin, actinomycin D, albendazole, aldosterone, alprazolam, amiodarone, amitriptyline, amprenavir, asimadoline, atorvastatin, bunitrolol, buspirone, carbamazepine, carvedilol, celiprolol, cyclosporine A, cimetidine, clotrimazole, colchicine, cortisone, daunorubicin, debrisoquine, dexamethasone, diazepam, digitoxin, digoxin, diltiazem, domperidone, doxorubicin, efavirenz, epirubicin, erythromycin, ergotamine, estradiol, estradiol glucuronide, erlotinib, etoposide, phenytoin, fentanyl, felodipine, phenothiazines, fexofenadine, fluoroquinolones, fluorouracil, FK-506, gentamicin, griseofulvin, hydrocortisone, imatinib, indinavir, itraconazole, ivermectin, ketoconazole, kaempferol, levofloxacin, lidocaine, loperamide, losartan, lovastatin, mebendazole, methylprednisolone, methotrexate, mibefradil, midazolam, nisoldipine, morphine, nelfinavir, nicardipine, nitrendipine, nifedipine, ondansetron, pentazocine, praziquantel, prednisolone, prednisone, quercetin, quinidine, ranitidine, rapamycin, rifabutin, rifampicin, ritonavir, saquinavir, sirolimus, sulfamethizole, tacrolimus, tamoxifen, talinolol, teniposide, terfenadine, tetracycline, topotecan, triamcinolone, valspodar, verapamil, vinblastine, vincristine, vindesine, zopiclone, derivatives thereof, and mixtures thereof.

The nanoparticles of the invention are particularly useful for the administration by the oral route of hydrophobic BAC (Class II and Class IV of the Biopharmaceutics Classification System).

In one particular embodiment of the invention, the BAC present in the nanoparticles of the invention is an antitumor agent (e.g. docetaxel, paclitaxel, campthotecin, doxorubicin, epirubicin, fluorouracil, cyclophosphamide, methotrexate, etc). In a more particular embodiment, the BAC is selected from the group consisting of docetaxel, campthotecin and paclitaxel. In a still more particular embodiment, the BAC is docetaxel.

The nanoparticles of the invention allow modifying the distribution of the BAC that they contain when they are administered by a route providing access to any mucosa of the organism (e.g., oral route, etc.).

Said nanoparticles of the invention have a particle size less than 1 μm, typically comprised between 1 and 999 nm, preferably between 10 and 900 nm, more preferably between 50 and 550 nm, even more preferably between 100 and 500 nm, still more preferably between 150 and 400 nm.

Process for Obtaining Nanoparticles

In another aspect, the invention relates to a process for producing nanoparticles comprising a matrix of an ester polymer conjugate of the invention and a biologically active compound (i.e. the nanoparticles of the invention), hereinafter "process [2] of the invention", which comprises the steps of:
- a) mixing an ester polymer conjugate of the invention with a biologically active compound in an organic medium, and
- b) desolvating the ester polymer conjugate by means of adding alcohol and water in the presence of a divalent metal.

In a particular embodiment, optionally in combination with one or more features of the various embodiments described above or below, the organic medium in step a) is acetone; and the alcohol used in step b) is ethanol.

The divalent metal that can be used for putting process [2] of the invention into practice is selected from the group consisting of calcium, magnesium, zinc, iron in divalent form, and combinations thereof. In a preferred embodiment, optionally in combination with one or more features of the various embodiments described above or below, the divalent metal is calcium; and may be obtained for example from a calcium salt. Illustrative non-limiting examples of calcium salts are calcium chloride, calcium acetate, calcium gluconate, calcium lactate, calcium sorbate, and mixtures thereof; preferably the calcium salt is calcium chloride.

Step a) of the process [2] of the invention is made by conventional methods known by persons skilled in the art, for example by means of:
- dissolving the ester polymer conjugate of the invention in an organic medium, and adding the biologically active compound; or alternatively,
- mixing (i) an organic solution containing the ester polymer conjugate of the invention with (ii) an organic solution or dispersion of the biologically active compound.

Step b) of the process [2] of the invention is also made by conventional methods known by persons skilled in the art, for example, by means of:
- adding (iii) an alcohol to the mixture obtained in step a), and immediately adding an (iv) aqueous solution of a divalent metal, or alternatively,
- adding a (v) hydroalcoholic mixture comprising a divalent metal to the mixture obtained in step a).

The process [2] of the invention covers all possible combinations of above methods of steps a) or b) described herein. However, in a preferred embodiment, optionally in combination with one or more features of the various embodiments described above or below, the process [2] of the invention comprises the steps of:
- a) mixing (i) an organic solution containing the ester polymer conjugate of the invention with (ii) an organic solution or dispersion of the biologically active compound, and
- b) desolvating the ester polymer conjugate by means of adding a hydroalcoholic mixture comprising a divalent metal to the mixture obtained in step a).

In a particular embodiment of the invention, optionally in combination with one or more features of the various embodiments described above or below, the hydroalcoholic mixture is 1:1 (v/v) (water/alcohol). In another particular embodiment, optionally in combination with one or more features of the various embodiments described above or below, said hydroalcoholic mixture comprises 0.5-5% (v/v) of a source of a divalent metal; preferably 1-3%. In a further particular embodiment said source of a divalent metal is an aqueous solution comprising 0.5-1% (w/v) of the corresponding salt.

In further particular embodiment, optionally in combination with one or more features of the various embodiments described above or below, the weight ratio between the ester polymer conjugate of the invention and the biologically active compound in the mixture of step a) is comprised in the range from 1:0.01 to 1:0.20, preferably from 1:0.02 to 1:0.15, more preferably from 1:0.03 1:0.10.

In a non-limiting illustrative manner, when the BAC is docetaxel or paclitaxel, a weight ratio ester polymer conjugate:BAC of 1:0.05 or 1:0.10 provides good results. In a similar way, when the BAC is camptothecin, a weight ratio ester polymer conjugate:BAC of 1:0.03 or 1:0.06 provides good results.

In a particular embodiment, optionally in combination with one or more features of the various embodiments described above or below, the organic/hydroalcoholic ratio (v/v) in the mixture obtained at the end of process [2] of the invention is 1:1-1:4, preferably is 1:2.

In one variant of the invention, said process for producing a nanoparticle according to the invention comprises an additional step c) of removing organic medium (for example, by means of evaporation under reduce pressure), and/or optionally purifying (for example, by means of filtration techniques, centrifugation or ultracentrifugation). Likewise, if desired, said process [2] of the invention may include an additional step d) of drying the formed nanoparticles in order to obtain the nanoparticles of the invention in the form of a powder. This form of presentation of said nanoparticles contributes to their stability and is further particularly useful for their eventual application in pharmaceutical products.

Virtually any conventional technique or method suitable for drying the nanoparticles can be used to perform this drying step; however, in a particular embodiment, the drying of the suspension containing nanoparticles is carried out by means of spray drying or by means of freeze-drying (lyophilization); preferably by means of freeze-drying. This treatment is generally carried out by adding a suitable protective agent of said nanoparticles, such as a saccharide, for example sucrose, lactose, trehalose, mannitol, maltodextrine, glucose, sorbitol, maltose, etc., and mixtures thereof to the suspension of the nanoparticles. Said protective agent protects the nanoparticles of the invention against degradation as well as oxidation during the drying process.

The nanoparticles obtainable by means of process [2] of the invention have the characteristics of the nanoparticles of the invention. Therefore, the nanoparticles obtained by process [2] of the invention, i.e., the nanoparticles comprising a matrix of an ester polymer conjugate of the invention and a biologically active compound produced by means of a process which comprises: a) mixing an ester polymer conjugate of the invention with a biologically active compound in an organic medium, and b) desolvating the ester polymer conjugate by means of adding alcohol and water in the presence of a divalent metal form an additional aspect of the present invention.

Particularly, the nanoparticles comprising a matrix of an ester polymer conjugate of the invention and a BAC obtained by means of a process which comprises: a) mixing (i) an organic solution containing the ester polymer conjugate of the invention with (ii) an organic solution or dispersion of the biologically active compound, and b) desolvating the ester polymer conjugate by means of adding a hydroalcoholic mixture comprising a divalent metal to the mixture obtained in step a), form an additional aspect of the present invention, optionally in combination with one or more features of the various embodiments described above or below.

Applications of Nanoparticles

The nanoparticles provided by the present invention (i.e. nanoparticle comprising a matrix of an ester polymer conjugate of the invention, as well as the nanoparticles directly obtained by process [2] of the invention) enable the encapsulation of considerable amounts of biologically active compounds, and its incorporation in pharmaceutical compositions. Said nanoparticles can be presented in the form of a suspension, preferably in an aqueous medium, or, alternatively, they can be presented in the form of a dry powder, for example as a lyophilizate together with a cryoprotective agent, maintaining the BAC in a stable condition and enabling its storage for long periods of time.

The nanoparticles of the invention appear to be able to cross the mucus layer and interact in an intimate way with the surface of the enterocytes, improving the absorption of the drug through the oral mucosa. Importantly, the nanoparticles provided by the present invention increase the oral bioavailability of BAC, providing sustained and constant plasma levels. Therefore, in another aspect, the invention relates to a nanoparticle according to the invention or a nanoparticle obtained by process [2] of the invention for use in medicine. Alternatively, the invention relates to a method for the prevention or treatment of a disease which comprises administering to a subject in need thereof a nanoparticle of the invention, or a nanoparticle obtained by a process [2] of the invention.

The dose of loaded nanoparticles of the invention to be administered to a subject in need of treatment with the BAC should be sufficient to trigger a beneficial therapeutic response in the patient over time. Thus, nanoparticles are administered to a patient in an amount sufficient to prevent, alleviate, reduce, cure or at least partially arrest symptoms and/or complications from the disease. An amount adequate to accomplish this is defined as a "therapeutically effective dose". The dose can vary within a broad range, and will depend, among other features, on the nature of the BAC, its activity or potency, the amount of BAC per nanoparticles, etc. Only by illustrative purposes, the dose of the loaded nanoparticles to be administered to a subject may be comprised, for example, between approximately 0.01 and approximately 10 mg per kg of body weight, preferably, between 0.1 and 2 mg per kg of body weight.

The particulars of the BAC have been mentioned in the "Definitions" section, and also in connection with the nanoparticles of the invention, and are incorporated herein by reference. The BAC that is comprised in the nanoparticles is elected depending on the disease to be treated. In a particular embodiment, optionally in combination with one or more features of the various embodiments described above or below, the BAC is an antitumor agent; in a more particular embodiment the BAC is selected from the group consisting of docetaxel, campthotecin and paclitaxel. Therefore, in another aspect, the invention relates to a nanoparticle comprising a matrix of an ester polymer conjugate of the invention, and a BAC (i.e. a nanoparticle of the invention or a nanoparticle obtained by process [2] of the invention), wherein the BAC is an antitumor agent, for use in a method of prevention or treatment of cancer; in other words, the invention also relates to a method for the prevention or treatment of cancer which comprises administering to a subject in need thereof a nanoparticle comprising a matrix of an ester polymer conjugate of the invention, and a BAC, wherein the BAC is an antitumor agent.

In another aspect, the invention relates to the use of a nanoparticle of the invention, or the use of a nanoparticle obtained by process [2] of the invention in the manufacture of a pharmaceutical composition.

In another aspect, the invention relates to a pharmaceutical composition, hereinafter "pharmaceutical composition of the invention", comprising i) at least one nanoparticle of the invention or at least one nanoparticle obtained by process [2] of the invention, and ii) a pharmaceutically acceptable carrier or vehicle. In a particular embodiment, said pharmaceutical composition of the invention comprises a plurality of nanoparticles of the invention and/or a plurality of nanoparticles obtained by a process [2] of the invention. The particulars of the nanoparticles have already been defined above and are incorporated herein by reference.

Advantageously, the nanoparticles in the pharmaceutical composition of the invention have a mean size comprised in the range from 10 to 900 nm, preferably from 50 to 550, more preferably from 100 to 500 nm, even more preferably from 150 to 400 nm, still more preferably about 250 nm.

The pharmaceutical composition of the invention may be formulated in a solid (for example, tablets, capsules, coated tablets, granulates, suppositories, sterile crystalline or amorphous solids which can be reconstituted to provide liquid forms, etc.), liquid (for example suspension or dispersion of the nanoparticles, etc.) or semisolid (gels, pomades, creams and the like) pharmaceutical dosage form. The described pharmaceutical compositions will comprise suitable carriers or vehicles for each formulation. Furthermore, the pharmaceutical composition can contain, as appropriate, stabilizers, suspensions, preservatives, surfactants and the like. These excipients will be chosen according to the selected pharmaceutical dosage form.

In a specific embodiment, said pharmaceutical composition is formulated as a pharmaceutical dosage form suitable for its administration by a route of access to mucosae. In a preferred embodiment, the pharmaceutical composition provided by this invention is orally administered; therefore the carrier or vehicle comprises one or more pharmaceutical excipients acceptable for the administration by oral route. Oral formulations are conventionally prepared by methods known by persons skilled in the art. A review of the different forms of administration of active ingredients, of the excipients to be used, and of the processes for manufacturing them can be found in the book "Tratado de Farmacia Galénica", by C. Fauli i Trillo, 10 Edition, 1993, Luzán 5, S. A. de Ediciones.

In another specific embodiment, the pharmaceutical composition of the invention is prepared in the form of a dry powder, for example as a lyophilizate.

The pharmaceutical compositions in accordance with this invention may contain the BAC or active ingredient in an amount that is in the range from 0.05% to 50%, preferably from 0.1% to 30%, more preferably 0.5% to 25%, even more preferably 1% to 20%, wherein the foregoing percentages are w/w versus the total weight of the composition or dosage form. Nevertheless, the suitable proportion will depend on each case of the BAC incorporated.

In another aspect, the invention relates to a pharmaceutical composition of the invention for use in medicine. In another aspect, the invention relates to the use of a pharmaceutical composition of the invention in the preparation of a medicament for the prevention or treatment of a disease. Alternatively, the invention relates to a method for the prevention or treatment of a disease which comprises administering to a subject in need thereof a pharmaceutical composition of the invention.

The therapeutically effective dose of the pharmaceutical composition to be administered depends on the individual case and, as customary, is to be adapted to the conditions of the individual case for an optimum effect. Thus it depends, of course, on the frequency of administration and on the potency and duration of action of the BAC employed in each case for therapy or prophylaxis, but also on the nature and severity of the disease and symptoms, and on the sex, age, weight, co-medication and individual responsiveness of the subject to be treated and on whether the therapy is acute or prophylactic. Doses may be adapted depending on subject weight, and for paediatric administration.

In a particular embodiment, optionally in combination with one or more features of the various embodiments described above or below, the pharmaceutical composition of the invention comprises i) at least one nanoparticle comprising a matrix of an ester polymer conjugate of the invention, and a BAC (i.e. a nanoparticle of the invention or a nanoparticle obtained by process [2] of the invention), wherein the BAC is an antitumor agent, and ii) a pharmaceutically acceptable carrier or vehicle. Preferably, the antitumor agent is selected from the group consisting of docetaxel, campthotecin and paclitaxel; preferably is docetaxel.

In this particular embodiment in which the BAC is an antitumor agent, the pharmaceutical composition of the invention may be used in a method of prevention or treatment of cancer.

Thus in a further aspect, the invention relates to a method for the prevention and/or the treatment of cancer which comprises administering to a subject in need thereof a therapeutically effective amount of a pharmaceutical composition of the invention comprising an antitumor agent; alternatively, the invention also relates to the use of a pharmaceutical composition of the invention comprising an antitumor agent in the preparation of a medicament for prevention or treatment of cancer.

In a more particular embodiment the pharmaceutical composition of the invention is selected from the group consisting of:
a pharmaceutical composition comprising:
  a) an ester polymer conjugate of PVM/MA with polyethylene glycol 2,000 from 38% to 47%,
  b) docetaxel from 3% to 5%,
  c) calcium from 0.1% to 0.2%, and
  d) a saccharide from 15% to 40%,
  wherein all the proportions are by weight with respect to the total weight of the composition;
a pharmaceutical composition comprising:
  a) an ester polymer conjugate of PVM/MA with metoxi-polyethylene glycol 2,000 from 38% to 47%,
  b) docetaxel from 3% to 5%,
  c) calcium from 0.1% to 0.2%, and
  d) a saccharide from 15% to 40%,
wherein all the proportions are by weight with respect to the total weight of the composition; and,
a pharmaceutical composition comprising:
  a) an ester polymer conjugate of PVM/MA with metoxi-polyethylene glycol 2,000 from 30% to 40%,
  b) camptothecin from 0.08% to 1.5%,
  c) calcium from 0.10% to 0.20%, and
  d) a saccharide from 15% to 40%,
wherein all the proportions are by weight with respect to the total weight of the composition.

The present invention covers all possible combinations of particular and preferred embodiments described herein.

EXAMPLES

The following examples describe the production and characterization of ester polymer conjugates of poly (vinyl methyl ether and maleic anhydride) copolymer (PVM/MA or Gantrez® AN) with a polyethylene glycol or derivative thereof containing a hydroxyl-terminal reactive group. Additionally, the following examples describe the production and characterization of nanoparticles based on said ester polymer conjugates of PVM/MA with different types of polyethylene glycols or derivative thereof containing a hydroxyl-terminal reactive group, and biologically active molecules. It has especially been found that these nanoparticles are capable of i) encapsulating considerable amounts of biologically active compounds (e.g. paclitaxel, docetaxel and campthotecin), and ii) crossing the mucus layer and interact in an intimate way with the surface of the enterocytes (improving the absorption of the drug).

As can be seen in said examples, when docetaxel is used as biologically active compound, its incorporation in said nanoparticles allows maintaining constant and sustained plasma levels of said drug for at least 72 h. Likewise, with campthotecin included in the nanoparticles of the invention as biologically active compound, plasma levels maintain for at least 48 h.

The general materials are described firstly.
Materials
Poly (methyl vinyl ether-co-maleic anhydride) or poly (anhydride) (PVM/MA) [Gantrez® AN 119] was purchased from ISP (Barcelona, Spain). Camptothecin (99.0%), paclitaxel (USP 26, grade>99.5%) and docetaxel (99.0%) were supplied by 21CECpharm (London, UK). Taxotere® was obtained from Aventis-Pharma (Cedex, France). Phosphate buffered saline (PBS), pancreatin, methoxy polyethylene glycol 2,000 (mPEG2) and polyethyleneglycols 2,000, 6,000 and 10,000 (PEG2, PEG6 and PEG10) were provided by Sigma-Aldrich (Spain). Pepsin, acetone, ethanol and acetonitrile were obtained from Merck (Darmstadt, Germany). Deionised reagent water (18.2 MΩ resistivity) was prepared by a water purification system (Wasserlab, Spain). All reagents and chemicals used were of analytical grade.

These examples are provided by way of illustration, and they are not intended to be limiting of the present invention.

Example 1

Preparation of Conventional PVM/MA Nanoparticles

Preparation of Empty Conventional PVM/MA Nanoparticles (NP)

100 mg PVM/MA were dissolved in 5 mL of acetone and nanoparticles were formed by the addition of a mixture of ethanol and water (1:1, v/v). Then, organic solvents were eliminated by evaporation under reduced pressure and the resulting suspension was filtered through a 0.45 μm membrane and purified twice by centrifugation 27,000×g for 20 min. The supernatant was removed and the pellet resuspended in water. Finally, the formulation was frozen and freeze-dried (Genesis 12EL, Virtis, USA) using sucrose (5% w/w) as cryoprotector. These are empty nanoparticles of PVM/MA, hereinafter NP formulations (NP).

Preparation of Conventional PVM/MA Nanoparticles Encapsulating Paclitaxel (PTX)

Paclitaxel-loaded PVM/MA nanoparticles were prepared by a solvent displacement method with some modifications. Briefly, 10 mg of paclitaxel were dispersed in 5 mL of acetone containing 100 mg of PVM/MA. The resulting mixture was maintained under magnetic agitation for 1 h at room temperature. After this time, nanoparticles were formed by the addition of 10 mL of ethanol followed by the addition of 10 mL of an aqueous solution containing 20 mg of disodium edetate. After homogenisation by magnetic agitation for 10 min, the organic solvents were removed by evaporation under reduced pressure (Büchi R-144, Switzerland) and the resulting suspensions purified by tangential filtration in Vivaspin tubes at 3000×g for 20 min. The supernatants were removed and the pellets resuspended in water. The purification process was repeated twice and finally, the formulations were frozen and freeze-dried (Genesis 12EL, Virtis, USA) using sucrose (5%) as cryoprotector. These formulations are PTX-loaded nanoparticles of PVM/MA, hereinafter PTX formulations.

Preparation of Conventional PVM/MA Nanoparticles Encapsulating Docetaxel (DTX)

Docetaxel-loaded PVM/MA nanoparticles were prepared by a solvent displacement method with some modifications. Briefly, 10 mg of docetaxel were dispersed in 5 mL of acetone containing 100 mg of PVM/MA. The resulting mixture was maintained under magnetic agitation for 1 h at room temperature. After this time, nanoparticles were formed by the addition of 10 mL of ethanol followed by the addition of 10 mL of an aqueous solution containing 20 mg of disodium edetate. After homogenisation by magnetic agitation for 10 min, the organic solvents were removed by evaporation under reduced pressure (Büchi R-144, Switzerland) and the resulting suspensions purified by tangential filtration in Vivaspin tubes at 3000×g for 20 min. The supernatants were removed and the pellets resuspended in water. The purification process was repeated twice and finally, the formulations were frozen and freeze-dried (Genesis 12EL, Virtis, USA) using sucrose (5%) as cryoprotector. These formulations are DTX-loaded nanoparticles of PVM/MA, hereinafter DTX formulations.

Preparation of Conventional PVM/MA Nanoparticles Encapsulating Camptothecin (CPT)

100 mg of PVM/MA and 10 mg of camptothecin were dissolved and dispersed in 2 and 3 mL of acetone, respectively. Camptothecin was sonicated for 1 min and mixed with the PVM/MA solution. Immediately, nanoparticles were formed by the addition of a mixture of ethanol and water (1:1, v/v). Then, organic solvents were removed by evaporation under reduced pressure and the resulting suspension was filtered through a 0.45 μm membrane and purified twice by centrifugation 27,000×g for 20 min. Finally, the formulation was frozen and freeze-dried (Genesis 12EL, Virtis, USA) using sucrose (5%, w/w) as cryoprotector. These formulations are CPT-loaded nanoparticles of PVM/MA, hereinafter CPT formulations.

Example 2

Preparation of Traditional Pegylated PVM/MA Nanoparticles

Preparation of Empty Traditional Pegylated PVM/MA Nanoparticles (PEG Trad)

Pegylated PVM/MA nanoparticles were prepared by a solvent displacement method. Briefly, 12.5 mg of polyethyleneglycol (PEG2, PEG6 or PEG10) were dissolved in 3 mL of acetone and, then, added to a solution of 100 mg of PVM/MA in 2 mL of the same organic solvent. The resulting mixture was maintained under magnetic agitation for 1 h at room temperature. Then, nanoparticles were formed by the addition of 10 mL of ethanol followed by the addition of 10 mL of water. The organic solvents were removed by evaporation under reduced pressure (Büchi R-144, Switzerland) and the resulting suspensions purified by tangential filtration in Vivaspin tubes at 3000×g for 20 min. The supernatants were removed and the pellets resuspended in water. The purification process was repeated twice and finally, the formulations were frozen and freeze-dried (Genesis 12EL, Virtis, USA) using sucrose (5%) as cryoprotector. The resulting pegylated nanoparticles of PVM/MA are: PEG2 trad, PEG6 trad and PEG10 trad formulations.

Preparation of Traditional Pegylated PVM/MA Nanoparticles Encapsulating Paclitaxel (PEG-PTX Trad)

Pegylated PVM/MA nanoparticles containing paclitaxel were prepared by a solvent displacement method with some modifications. Briefly, on one hand, 12.5 mg of polyethyleneglycol (PEG2, PEG6 or PEG10) were dissolved in 3 mL of acetone and, then, added to a solution of 100 mg of PVM/MA in 2 mL of the same organic solvent. The resulting mixture was maintained under magnetic agitation. In parallel, 10 mg of paclitaxel was dissolved in 0.5 mL of acetone and added to the mixture of polymers. Then, the organic phase (containing paclitaxel, PVM/MA and PEG) was magnetically stirred for 1 h at room temperature. After this time, nanoparticles were formed by the addition of 10 mL of ethanol followed by the addition of 10 mL of an aqueous solution containing 20 mg of disodium edetate. After homogenisation by magnetic agitation for 10 min, the organic solvents were removed by evaporation under reduced pressure (Büchi R-144, Switzerland) and the resulting suspensions purified by tangential filtration in Vivaspin tubes at 3000×g for 20 min. The supernatants were removed and the pellets resuspended in water. The purification process was repeated twice and finally, the formulations were frozen and freeze-dried (Genesis 12EL, Virtis, USA) using sucrose (5%) as cryoprotector. Hence, PTX-loaded traditional pegylated nanoparticles of PVM/MA are available, hereinafter PEG2-PTX trad, PEG6-PTX trad and PEG10-PTX trad formulations.

Preparation of Traditional Pegylated PVM/MA Nanoparticles Encapsulating Docetaxel (PEG-DTX Trad)

Polyethyleneglycol 2,000 (12.5 mg) was firstly dissolved in 3 mL of acetone and added to a solution of 100 mg of PVM/MA also in 2 mL of acetone. The resulting mixture was maintained under magnetic agitation. On the other hand, docetaxel was dissolved in 0.5 mL of acetone and added to the solution. Then, the organic phase containing docetaxel, PVM/MA and PEG2 was incubated for a period of about 1 h under magnetic stirring at room temperature. Afterwards, nanoparticles were formed by the addition of 10 mL of ethanol followed by the addition of 10 mL of an aqueous solution containing glycine (50 mg) and disodium edetate (18 mg) and allowed to homogenize for 10 min. The organic solvents were eliminated by evaporation under reduced pressure and the final volume was adjusted with glycine solution to 10 mL. The suspension was purified by tangential filtration in Vivaspin tubes (300,000 MWCO, Sartorius Group, Germany) at 4,000×g for 15 min. The pellets were resuspended in water and the purification step was repeated twice. Finally, the formulations were frozen and then freeze-dried using sucrose (5%) as cryoprotector. Hence, DTX-loaded traditional pegylated nanoparticles of PVM/MA are available, hereinafter, PEG2-DTX trad formulations.

Preparation of Traditional Pegylated PVM/MA Nanoparticles Encapsulating Camptothecin (PEG-CPT Trad)

Pegylated nanoparticles were prepared at a polymer/CPT/PEG ratio of 1/0.03/0.125. PEG2 or PEG6, and camptothecin, were dissolved in acetone and mixed in different conditions. Immediately, nanoparticles were formed by the addition of a mixture of ethanol, water, glycine and disodium edetate. After homogenisation for 10 min, organic solvents were removed by evaporation under reduced pressure. Then, the resulting suspensions were filtered through a 0.45 μm membrane and purified twice through Vivaspin tubes (300,000 MWCO, Sartorius group, Germany) at 3000×g for 20 min. Finally, the formulations were frozen and then freeze-dried (Genesis 12EL, Virtis, USA) using sucrose (5%, w/w) as cryoprotector. Hence CPT-loaded traditional pegylated nanoparticles of PVM/MA are available, hereinafter PEG2-CPT trad and PEG6-CPT trad formulations.

Example 3

Preparation and Characterization of Ester Polymer Conjugates of PVM/MA 3.1 Preparation of Ester Polymer Conjugates of PVM/MA In this case, polyethyleneglycols of different molecular weights 2,000, 6,000 or 10,000 and methoxy-polyethyleneglycol 2000 were tested.

To prepare the ester polymer conjugates, 5 g of PVM/MA were dissolved in 250 ml of an organic solvent (i.e. acetone) and incubated with different amounts of polyethyleneglycol or derivative thereof for 3 h under magnetic stirring at 50° C. The hydroxyl-terminated molecule:(PVM/MA) ratios tested were:

mPEG:(PVM/MA) 1:5; for mPEG2
PEG: (PVM/MA) 1:20; 1:8; for PEG2, PEG6 and PEG10

After incubation, the solvent was removed and the resulting ester polymer conjugate was dried by reduced pressure evaporation (Büchi R210, Switzerland). Finally, the dried ester polymer conjugates obtained were purified by washing with dichloromethane ($CH_2Cl_2$) and filtering under vacuum (all-glass filter, Merck Millipore, Germany) until no traces of unreacted hydroxyl-terminated molecule were detected in the liquid by thin layer chromatography (TLC). For this purpose, a mixture of dichloromethane/methanol $CH_2Cl_2$/$CH_3OH$ (9:1) was used as mobile phase and iodine for revealing. This step will improve the solubility of the new polymer conjugate in an organic solvent.

3.2 Characterization of Ester Polymer Conjugates of PVM/MA

After the synthesis, the resulting ester polymer conjugates of PVM/MA with PEG2, PEG6 and PEG10 (at a ratio PEG:PVM/MA of 1:8) and ester polymer conjugate of PVM/MA with mPEG2 (at a ratio mPEG:PVM/MA of 1:5) were physico-chemically characterized in order to obtain evidences of the PVM/MA backbone modification as well as to estimate the degree of substitution (DS) and the molecular weight ($M_w$).

The following techniques were employed:

Infrared spectroscopy (IR): IR spectroscopy was performed in a Nicolet Avatar 360FT-IR equipment (Thermo, USA) based on reflectance technology. This technique allowed identifying the binding of the —OH functional group of the hydroxyl-terminated molecule (PEG or mPEG) with the anhydride groups of PVM/MA.

Elemental analysis (CHN): All the pre-formed ester polymer conjugates were analysed in a CHN-900 Leco apparatus (Leco Corporations, USA). This technique helps to determine the composition of the polymers and detect the differences in the C/H content relationship when the hydroxyl-terminated molecule (PEG or mPEG) is incorporated into the PVM/MA structure.

Titration: PVM/MA or its ester polymer conjugates were first hydrated and dispersed in water till their total solubilization. At this moment the aqueous solutions of the polymers were titrated with NaOH 0.2 N solution in the presence of phenolphthalein, used as indicator. Titration was used to measure the percentage of free carboxylic (—COOH) groups. The decrease of free carboxylic groups in the ester polymer conjugates in comparison to unmodified PVM/MA polymer evidenced the molecule binding.

Size Exclusion Chromatography-Multi-Angle Laser Light Scattering (SEC-MALLS): SEC-MALLS technique is the key to determine the molecular mass of a polymer in solution. This technique uses a calibration curve of elution times against molar mass on size exclusion columns and a single measurement of one polymer allows knowing its molecular weight.

Dynamic Light Scattering (DLS): This technique provides the hydrodynamic radius ($R_h$) of the polymers, giving an estimation of the most likely conformation of the polymer in solution. DLS measurements were performed at a scattering angle of 90° using a DynaPro-MS/X photon correlation spectrometer equipped with a 248-channel multi-tau correlator and a Peltier effect temperature unit (Protein Solutions Inc, USA). The wavelength of the laser was 852.2 nm at 100% intensity. The polymers conjugates were measured at 25° C. using tetrahydrofurane as solvent.

Nuclear magnetic resonance spectroscopy ($^1$H-NMR): $^1$H-NMR spectra were recorded in a Bruker Avance 400 apparatus of 400 MHz (Bruker, USA) using a pulse program zg30 and a waiting time between pulses ($D_0$) of 1 s. Pre-formed ester polymer conjugates were dissolved in deuterated acetone (acetone-$d_6$), as solvent.

3.3 Results

The infrared spectroscopy study of pre-formed ester polymer conjugates showed the formation of a new binding at ~1705 $cm^{-1}$ associated with the stretching of the new ester carbonyl group ν (C=O) originated as a result of the reaction of the hydroxyl of PEGs or mPEG with anhydride groups of PVM/MA, see FIG. 1.

Once it was evidenced by IR that a bond had been developed between the polymer and the hydroxyl-terminated molecule further studies to evidence the modification of the polymer were carried out.

Table 1 summarises the composition in carbon (C), hydrogen (H) and oxygen (O) determined for the original PVM/MA polymer and its ester polymer conjugates. Elemental analysis showed a decrease in % C and an increase in % O, confirming a marked change in the composition of ester polymer conjugates of PVM/MA compared to unmodified PVM/MA, being the C-to-O ratio (C/O ratio) lower for ester polymer conjugates than for the original copolymer.

TABLE 1

Elemental analysis of the PVM/MA and its ester polymer conjugates.

| Polymer | % C | % H | % O | C/O |
|---|---|---|---|---|
| PVM/MA | 53.49 | 5.18 | 41.33 | 1.29 |
| PVM/MA-PEG2 | 49.78 | 5.19 | 45.03 | 1.11 |

TABLE 1-continued

Elemental analysis of the PVM/MA and its ester polymer conjugates.

| Polymer | % C | % H | % O | C/O |
|---|---|---|---|---|
| PVM/MA-PEG6 | 49.96 | 5.18 | 44.89 | 1.11 |
| PVM/MA-PEG10 | 49.85 | 5.68 | 44.47 | 1.12 |
| PVM/MA-mPEG2 | 48.33 | 6.01 | 45.66 | 1.06 |

On the other hand, titration confirmed a reduction in the amount of free —COOH groups, due to the occupation of the anhydride ring by the hydroxyl-terminated molecule (PEG or mPEG) binding (table 2).

TABLE 2

Titration of PVM/MA and its ester polymer conjugates.

| Polymer | % Free COOH |
|---|---|
| PVM/MA | 100 |
| PVM/MA-PEG2 | 57.67 |
| PVM/MA-PEG6 | 40.68 |
| PVM/MA-PEG10 | 54.79 |
| PVM/MA-mPEG2 | 50.27 |

DLS showed the values of hydrodynamic radius of PVM/MA and of ester polymer conjugates of PVM/MA with PEGs or mPEG. In all cases, the hydrodynamic radius increases with respect to starting PVM/MA, except for PVM/MA-methoxy polyethylene glycol 2,000 conjugate, that shows a slightly lower but very similar value compared to unmodified PVM/MA polymer (table 3). This would indicate a change in the molecular conformation when the polymer conjugates are solved in an organic solvent. The absence of hydrogen atoms in the methoxy group in mPEG molecules would promote the folding of the molecule in lower grade than the hydroxyl groups present in PEG molecules.

TABLE 3

Determination of hydrodynamic radius ($R_h$) of PVM/MA and its ester conjugates using DLS.

| Polymer | $R_h$ |
|---|---|
| PVM/MA | 18.96 |
| PVM/MA-PEG2 | 1158.68 |
| PVM/MA-PEG6 | 518.85 |
| PVM/MA-PEG10 | 114.52 |
| PVM/MA-mPEG2 | 12.89 |

Finally, $^1$H-NMR spectra of the ester polymer conjugates showed in all cases the presence of a chemical shift corresponding to —O—$CH_2$—$CH_2$— poly(ethylene) units in the molecules (PEG or mPEG) (FIG. 2).

In order to estimate the percentage of the hydroxyl-terminated molecules in the resulting ester polymer conjugates (D.S.), the ratio between the area of the peak associated to "a" protons in PVM/MA molecule (see FIG. 2A) and the area of one characteristic hydroxyl-terminated molecule peak (new chemical shift in the ester polymer conjugate highlighted in FIGS. 2B-2E) was calculated.

With these results, the average molecular weight ($M_w$) of the resulting conjugates was also estimated, considering 95.5 kDa the molecular weight of Gantrez® AN 119, as calculated by SEC-MALLS (table 4).

TABLE 4

Estimated molecular weight ($M_w$) and degree of substitution (DS) for the different conjugates tested calculated by a $^1$H-NMR.

| Polymer | $M_w$ (KDa) | D.S. (%) |
|---|---|---|
| PVM/MA | 95.5* | — |
| PVM/MA-PEG2 | 103.11 | 7.4 |
| PVM/MA-PEG6 | 107.69 | 11.3 |
| PVM/MA-PEG10 | 104.79 | 8.9 |
| PVM/MA-mPEG2 | 102.98 | 7.3 |

*Molecular weight obtained by SEC/MALLS

Once the ester polymer conjugates were purified and characterized, the preparation of the nanoparticles was carried out and the study of their properties was also performed.

Example 4

Preparation of Nanoparticles Comprising a Matrix of an Ester Polymer Conjugate of PVM/MA Preparation of Empty Nanoparticles Comprising a Matrix of an Ester Polymer Conjugate of PVM/MA (PEG Conj or mPEG Conj)

The preparation of the nanoparticles was carried out as follows. 100 mg of pre-formed ester polymers of PVM/MA conjugated with polyethyleneglycol 2,000, polyethyleneglycol 6,000, polyethyleneglycol 10,000 [ratios PEG2:(PVM/MA), PEG6:(PVM/MA) and PEG10:(PVM/MA) used were 1:20] or methoxy polyethyleneglycol 2,000 [ratio mPEG2:(PVM/MA) was 1:5] were dissolved in 5 mL acetone, and desolvated by the addition of 10 mL of a hydroalcoholic mixture 1:1 (v/v) (water/ethanol) containing 1% (v/v) of an aqueous solution of $CaCl_2$ 0.8% (w/v) under magnetic stirring at room temperature. The organic solvents were removed by evaporation under reduced pressure (Büchi 8210, Switzerland). The resulting suspensions were filtered through a 0.45 μm membrane and purified by centrifugation (Sigma 3 K30, Germany) at 17,000 rpm for 20 min at 4° C. The supernatants were removed, and the pellets were resuspended in water. The purification step was repeated twice. Finally, the formulations were frozen and freeze-dried (Genesis 12EL, Virtis, USA) using sucrose (5% w/v) as cryoprotector. In this way, unload nanoparticles from pre-formed ester polymer conjugates of PVM/MA with PEG2, PEG6, PEG10 or mPEG2 were obtained: PEG2 conj, PEG6 conj, PEG10 conj and mPEG2 conj formulations, respectively.

Preparation of Nanoparticles Comprising a Matrix of an Ester Polymer Conjugate of PVM/MA with Methoxy Polyethyleneglycol 2,000 Encapsulating Paclitaxel (mPEG2-PTX Conj)

100 mg of pre-formed ester polymer conjugate of PVM/MA with methoxy polyethyleneglycol 2,000 [mPEG2:(PVM/MA) ratio of 1:5] were dissolved in 4 mL of acetone. In parallel, 10 mg of paclitaxel were dispersed in 1 mL of acetone. The solution of the conjugate and the dispersion of paclitaxel were mixed under magnetic stirring at room temperature, and then the nanoparticles were formed by the addition of 10 mL of a hydroalcoholic mixture 1:1 (v/v) (water/ethanol) containing 1% (v/v) of an aqueous solution of $CaCl_2$ 0.8% (w/v). The organic solvents were removed by evaporation under reduced pressure (Büchi 8210, Switzerland). The resulting suspensions were filtered through a 0.45 μm membrane and purified by centrifugation (Sigma 3 K30, Germany) at 17,000 rpm for 20 min at 4° C. The supernatants were removed, and the pellets were resuspended in water. The purification step was repeated twice. Finally, the formulations were frozen and freeze-dried (Genesis 12EL, Virtis, USA) using sucrose (5% w/v) as cryoprotector. These are mPEG2-PTX conj nanoparticles formulations.

Preparation of Nanoparticles Comprising a Matrix of an Ester Polymer Conjugate of PVM/MA with Polyethyleneglycol 2,000 Encapsulating Paclitaxel (PEG2-PTX Conj)

100 mg of pre-formed ester polymer conjugate of PVM/MA with polyethyleneglycol 2,000 [PEG2:(PVM/MA) ratio of 1:20] were dissolved in 4 mL of acetone. In parallel, 10 mg of paclitaxel were dispersed in 1 mL of acetone. The solution of the conjugate and the dispersion of paclitaxel were mixed under magnetic stirring at room temperature, and then the nanoparticles were formed by the addition of 10 mL of a hydroalcoholic mixture 1:1 (v/v) (water/ethanol) containing 1% (v/v) of an aqueous solution of $CaCl_2$ 0.8% (w/v). The organic solvents were removed by evaporation under reduced pressure (Büchi 8210, Switzerland). The resulting suspensions were filtered through a 0.45 µm membrane and purified by centrifugation (Sigma 3 K30, Germany) at 17,000 rpm for 20 min at 4° C. The supernatants were removed, and the pellets were resuspended in water. The purification step was repeated twice. Finally, the formulations were frozen and freeze-dried (Genesis 12EL, Virtis, USA) using sucrose (5% w/v) as cryoprotector. These are PEG2-PTX conj nanoparticles formulations.

Preparation of Nanoparticles Comprising a Matrix of an Ester Polymer Conjugate of PVM/MA with Methoxy Polyethyleneglycol 2,000 Encapsulating Docetaxel (mPEG2-DTX Conj)

100 mg of pre-formed ester polymer conjugate of PVM/MA with methoxy polyethyleneglycol 2,000 [mPEG2:(PVM/MA) ratio of 1:5] were dissolved in 4 mL of acetone. In parallel, 10 mg of docetaxel were dispersed in 1 mL of acetone. The solution of the conjugate and the dispersion of docetaxel were mixed under magnetic stirring at room temperature, and then the nanoparticles were formed by the addition of 10 mL of a hydroalcoholic mixture 1:1 (v/v) (water/ethanol) containing 1% (v/v) of an aqueous solution of $CaCl_2$ 0.8% (w/v). The organic solvents were removed by evaporation under reduced pressure (Büchi 8210, Switzerland). The resulting suspensions were filtered through a 0.45 µm membrane and purified by centrifugation (Sigma 3 K30, Germany) at 17,000 rpm for 20 min at 4° C. The supernatants were removed, and the pellets were resuspended in water. The purification step was repeated twice. Finally, the formulations were frozen and freeze-dried (Genesis 12EL, Virtis, USA) using sucrose (5% w/v) as cryoprotector. These are mPEG2-DTX conj nanoparticles formulations.

Preparation of Nanoparticles Comprising a Matrix of an Ester Polymer Conjugate of PVM/MA with Polyethyleneglycol 2,000 Encapsulating Docetaxel (PEG2-DTX Conj)

100 mg of pre-formed ester polymer conjugate of PVM/MA with polyethyleneglycol 2,000 [PEG2:(PVM/MA) ratio of 1:20] were dissolved in 4 mL of acetone. In parallel, 10 mg of docetaxel were dispersed in 1 mL of acetone. The solution of the conjugate and the dispersion of docetaxel were then mixed under magnetic stirring at room temperature, and then, the nanoparticles were formed by the addition of 10 mL of a hydroalcoholic mixture 1:1 (v/v) (water/ethanol) containing 1% (v/v) of an aqueous solution of $CaCl_2$ 0.8% (w/v). The organic solvents were removed by evaporation under reduced pressure (Büchi 8210, Switzerland). The resulting suspensions were filtered through a 0.45 µm membrane and purified by centrifugation (Sigma 3 K30, Germany) at 17,000 rpm for 20 min at 4° C. The supernatants were removed, and the pellets were resuspended in water. The purification step was repeated twice. Finally, the formulations were frozen and freeze-dried (Genesis 12EL, Virtis, USA) using sucrose (5% w/v) as cryoprotector. These are PEG2-DTX conj nanoparticles formulations.

Preparation of Nanoparticles Comprising a Matrix of an Ester Polymer Conjugate of PVM/MA with Methoxy Polyethyleneglycol 2,000 Encapsulating Camptothecin (mPEG2-CPT Conj)

100 mg of pre-formed ester polymer conjugate of PVM/MA with methoxy polyethyleneglycol 2,000 [mPEG2:(PVM/MA) ratio of 1:5] were dissolved in 4 mL of acetone. In parallel, 3 mg of camptothecin were dispersed in 1 mL of acetone and sonicated for 30 s. The solution of the conjugate and the dispersion of camptothecin were mixed under magnetic stirring at room temperature, and then the nanoparticles were formed by the addition of 10 ml of a hydroalcoholic mixture 1:1 (v/v) (water/ethanol) containing 3% (v/v) of an aqueous solution of $CaCl_2$ 0.8% (w/v). After elimination of the organic solvents under reduced pressure (Büchi 8210, Switzerland), the resulting suspensions were filtered through a 0.45 µm membrane and purified by centrifugation (Sigma 3 K30, Germany) at 17,000 rpm for 20 min. The supernatants were removed and the pellets resuspended in water. Finally, the formulations were frozen and freeze-dried (Genesis 12EL, Virtis, USA) using sucrose (5% w/v) as cryoprotector. These are mPEG2-CPT conj nanoparticles formulations.

Example 5

Physico-Chemical Characterization of Nanoparticles

In order to perform these studies, the formulations of nanoparticles described in Examples 1, 2 and 4 were used.

5.1 Material and Methods

The mean hydrodynamic diameter of the nanoparticles and the zeta potential were determined by photon correlation spectroscopy (PCS) and electrophoretic laser Doppler anemometry, respectively, using a Zetasizer analyzer system (Brookhaven Instruments Corporation, New York, USA). The diameter of the nanoparticles was determined after dispersion in ultrapure water (1:10) and measured at 25° C. by dynamic light scattering angle of 90° C. The zeta potential was determined in the same equipment as follows: 200 µL of the same samples were diluted in 2 mL of a 0.1 mM KCl solution.

The study of the surface morphology of the formulations was also carried out by scanning electron microscopy (SEM) in a Zeiss DSM940 digital scanning electron microscope (Oberkochen, Germany) coupled with a digital image system (Point Electronic GmBh, Germany). Previously, nanoparticles were diluted with deionized water and centrifuged at 17,000 rpm (Sigma 3 K30, Germany) for 20 min at 4° C. The pellet was dried and shaded with a 9 nm gold layer in a Emitech K 550 Sputter-Coater (Ahsford, UK). Finally, the yield of nanoparticles formation was calculated by gravimetry from the difference between the initial amount of the polymer used to prepare nanoparticles and the weight of the freeze-dried samples.

$$\mathrm{Yield}(\%) = \left(\frac{NPfinal}{Polymer initial}\right) \times 100$$

Paclitaxel Content of the Nanoparticles

The amount of paclitaxel loaded into nanoparticles was quantified by HPLC-UV in an Agilent model 1200 series LC and a diode-array detector set at 228 nm. The chromatographic system was equipped with a reversed-phase 150 mm×3 mm C18 Phenomenex Gemini column (particle size 5 μm) and a precolumn (Phenomenex SecurityGuard C18). The mobile phase, pumped at 0.5 mL/min, was a mixture of phosphate buffer (0.01 M, pH 2) and acetonitrile (50:50, v/v). The column was set at 30° C. and the injection volume was 100 μL. Docetaxel was used as internal standard. Calibration curves were designed over the range 80 and 7000 ng/mL ($r^2$>0.999). The limit of quantification was calculated to be 40 ng/mL. For analysis, nanoparticles were solubilized with acetonitrile (1:5 v/v). Samples were transferred into auto-sampler vials, capped and placed in the HPLC auto-sampler. Each sample was assayed in triplicate and results were expressed as the amount of paclitaxel (in μg) per mg of nanoparticles.

Docetaxel Content of the Nanoparticles

The amount of docetaxel loaded into nanoparticles was quantified by HPLC-UV in an Agilent model 1200 series LC and a diode-array detector set at 228 nm. The chromatographic system was equipped with a reversed-phase 150 mm×3 mm C18 Phenomenex Gemini column (particle size 5 μm) and a precolumn (Phenomenex SecurityGuard C18). The mobile phase, pumped at 0.5 mL/min, was a mixture of phosphate buffer (0.01 M, pH 2) and acetonitrile (50:50, v/v). The column was placed at 30° C. and the injection volume was 100 pt. Paclitaxel was used as internal standard. Calibration curves were designed over the range 1.25 and 320 μg/mL ($r^2$>0.999). The limit of quantification was calculated to be 60 ng/mL. For analysis, nanoparticles were solubilized with acetonitrile (1:8 v/v). Samples were transferred into auto-sampler vials, capped and placed in the HPLC auto-sampler. Each sample was assayed in triplicate and results were expressed as the amount of docetaxel (in μg) per mg of nanoparticles.

Camptothecin Content of the Nanoparticles

The amount of camptothecin loaded into nanoparticles was quantified by HPLC-FLD in an Agilent model 1100 series LC and fluorescence detector set at excitation and emission of 380 and 418 nm respectively. The chromatographic system was equipped with a reversed-phase 150 mm×3 mm C18 Phenomenex Gemini column (particle size 5 μm) and a precolumn (Phenomenex SecurityGuard C18). The mobile phase, pumped at 1 mL/min consisted on a mixture 50:50 (v/v) of acetonitrile and trifluoroacetic acid 0.01% (v/v). The column was placed at 30° C. and the injection volume was 20 pt. Calibration curves were designed over the range of 0.48 and 8000 ng/mL ($r^2$>0.999). The limit of quantification was calculated to be 1.3 ng/mL. For analysis, nanoparticles were solubilized with acetonitrile (1:10, v/v). Samples were transferred into auto-sampler vials, capped and placed in the HPLC auto-sampler. Each sample was assayed in triplicate and results were expressed as the amount of camptothecin (in μg) per mg of nanoparticles.

5.2 Results

The main physicochemical characteristics of the different unload nanoparticle formulations are summarized in table 5.

TABLE 5

Physico-chemical properties of the different unloaded PVM/MA nanoparticles synthesized. Data expressed as mean ± S.D. (n = 3).

| | Size (nm) | PDI | Zeta potential (mV) | Ligand content (μg/ mg NP)* | Yield (%) |
|---|---|---|---|---|---|
| NP | 297 ± 1 | 0.025 ± 0.015 | −40 ± 2 | — | 74 |
| PEG2 trad | 148 ± 2 | 0.095 ± 0.009 | −41 ± 3 | 59 | 71 |
| PEG6 trad | 131 ± 1 | 0.104 ± 0.011 | −40 ± 0.2 | 89 | 66 |
| PEG10 trad | 208 ± 1.4 | 0.081 ± 0.023 | −43 ± 0.5 | 60 | 82 |
| PEG2 conj | 134 ± 1 | 0.163 ± 0.015 | −44 ± 1 | 27 ± 1 | 58 |
| PEG6 conj | 230 ± 1 | 0.082 ± 0.008 | −35 ± 1 | 39 ± 1 | 77 |
| PEG10 conj | 322 ± 8 | 0.231 ± 0.018 | −32 ± 1 | 35 ± 1 | 64 |
| mPEG2 conj | 259 ± 6 | 0.200 ± 0.040 | −33 ± 4 | 95 ± 1 | 81 |

*Ligand (hydroxyl-terminated molecule) content in polymer conjugates calculated by $^1$H-NMR.

It can be noticed that the hydroxyl-terminated molecule (ligand) content in mPEG2-conj nanoparticles is significantly higher compared to the rest of the polymer conjugates nanoparticles. This is logical because the starting amount of mPEG2 used to form the ester polymer conjugate of PVM/MA is much higher respect PEG2, PEG6 or PEG10.

Characterization of the Paclitaxel-Loaded Nanoparticles

The main physicochemical characteristics of the different nanoparticle formulations loaded with paclitaxel (PEG-PTX) are summarized in table 6. In the first place, nanoparticles containing the PEG2 conjugate (ester polymer conjugate of PVM/MA with PEG2) displayed bigger sizes than the nanoparticles with mPEG2 conjugate (ester polymer conjugate of PVM/MA with mPEG2). For the PEG2 conjugate, the sizes were close to 400 nm while for the other formulation containing mPEG2 conjugate sizes were smaller, around 300 nm.

Regarding the zeta potential, the loaded nanoparticles containing mPEG2 conjugate presented a slightly more negative surface charge, around −38 mV. The nanoparticles formulated with PEG2 conjugate displayed a surface charge around −33 mV. Furthermore, the yield of the process was calculated to be around 70% for both formulations. Focusing on the amount of PTX loaded in the nanoparticles, for mPEG2 and PEG2 conjugates was calculated to be around 160 μg/mg NP.

TABLE 6

Physicochemical characterization of the different PVM/MA nanoparticles. Data expressed as mean ± S.D. (n = 3).

| Formulations | Size (nm) | PDI | Zeta potential (mV) | PTX loading (µg PTX/mg NP) | Yield (%) |
|---|---|---|---|---|---|
| NP | 297 ± 1 | 0.025 | −40 ± 2 | — | 74 |
| PTX | 177 ± 3 | 0.038 | −44.2 ± 7.1 | 78.1 ± 3.2 | 62 |
| PEG2 trad | 148 ± 2 | 0.095 ± 0.009 | −41 ± 3 | — | 71 |
| PEG6 trad | 131 ± 1 | 0.104 ± 0.011 | −40 ± 0.2 | — | 66 |
| PEG10 trad | 208 ± 1.4 | 0.081 ± 0.023 | −43 ± 0.5 | — | 82 |
| PEG2-PTX trad | 178 ± 4 | 0.154 | −40.3 ± 1.1 | 150.1 ± 5.2 | 60 ± 4 |
| PEG6-PTX trad | 180 ± 5 | 0.173 | −39.5 ± 4.2 | 144.1 ± 3.1 | 64 |
| PEG10-PTX trad | 188 ± 2 | 0.136 | −41.1 ± 1.3 | 144.5 ± 6.4 | 63 |
| PEG2 conj | 134 ± 1 | 0.163 ± 0.015 | −44 ± 1 | — | 58 |
| mPEG2 conj | 259 ± 6 | 0.200 ± 0.040 | −33 ± 4 | — | 81 |
| PEG2-PTX conj | 430 ± 8 | 0.280 | −33 ± 6 | 152 ± 8 | 69 ± 8 |
| mPEG2-PTX conj | 318 ± 9 | 0.230 | −38 ± 4 | 160 ± 9 | 70 ± 4 |

If we compare the nanoparticle yield between PEG2-PTX trad and PEG2-PTX conj formulations, the percentage of formed nanoparticles is higher in the case of using ester polymer conjugate of PVM/MA with PEG2.

Characterization of the Docetaxel-Loaded Nanoparticles

Conjugate nanoparticles were successfully prepared by the solvent displacement method. The main physicochemical characteristics of the different nanoparticle formulations loaded with docetaxel (PEG-DTX) are summarized in table 7. In first place, loaded nanoparticles containing the PEG2 conjugate (ester polymer conjugate of PVM/MA with PEG2) displayed bigger sizes than the loaded nanoparticles with mPEG2 conjugate (ester polymer conjugate of PVM/MA with mPEG2). For the PEG2, the sizes were close to 400 nm while for the other formulation containing mPEG2 sizes were smaller, around 300 nm.

Regarding the zeta potential, the nanoparticles containing mPEG2 presented a slightly more negative surface charge, around −39 mV. The nanoparticles formulated with PEG2 conjugate displayed a surface charge around −33 mV.

Furthermore, the yield of the process was calculated to be around 60% for both formulations. Focusing on the amount of docetaxel loaded in the nanoparticles, for mPEG2 and PEG2 conjugate was calculated to be around 100 µg/mg NP.

Characterization of the Camptothecin-Loaded Nanoparticles

The physicochemical characteristics of the resulting nanoparticles containing camptothecin are summarized in table 8. When nanoparticles were loaded with camptothecin in mPEG2 conj (ester polymer conjugate of PVM/MA with mPEG2) nanoparticles, the mean size was approximately 195 nm. The polydispersity index (PDI) was lower than 0.3, which implies homogeneous formulations. Concerning the zeta potential of nanoparticles, formulations were formed by particles with negative surface charges, of around −36 mV. Furthermore, the yield of the process was approximately 70%. Regarding the drug loading, the amount of camptothecin encapsulated in nanoparticles from conjugates reached 11 µg/mg. The amount of camptothecin loaded in traditional pegylated nanoparticles was slightly higher for PEG2-CPT traditional than for PEG6-CPT traditional, reaching 9 µg/mg of nanoparticles.

TABLE 7

Physicochemical characterization of the different PVM/MA nanoparticles. Data expressed as mean ± S.D. (n = 3).

| Formulations | Size (nm) | PDI | Zeta potential (mV) | DTX loading (µg DTX/mg NP) | Yield (%) |
|---|---|---|---|---|---|
| NP | 297 ± 1 | 0.025 ± 0.015 | −40 ± 2 | — | 74 |
| DTX | 219 ± 2 | 0.128 ± 0.029 | −43 ± 1 | 60 ± 2 | 65 |
| PEG2 trad | 148 ± 2 | 0.095 ± 0.009 | −41 ± 3 | — | 71 |
| PEG2-DTX trad | 203 ± 4 | 0.060 ± 0.010 | −36 ± 4 | 110 ± 3 | 62 ± 3 |
| PEG2 conj | 134 ± 1 | 0.163 ± 0.015 | −44 ± 1 | — | 58 |
| mPEG2 conj | 259 ± 6 | 0.200 ± 0.040 | −33 ± 4 | — | 81 |
| PEG2-DTX conj | 415 ± 4 | 0.246 ± 0.024 | −33 ± 1 | 94 ± 5 | 64 ± 9 |
| mPEG2-DTX conj | 339 ± 7 | 0.083 ± 0.038 | −39 ± 5 | 100 ± 6 | 60 ± 9 |

TABLE 8

Physicochemical characterization of the different nanoparticles.
Data expressed as mean ± S.D. (n = 3).

| Formulations | Size (nm) | PDI | Zeta potential (mV) | CPT loading (µg CPT/mg NP) | Yield (%) |
|---|---|---|---|---|---|
| NP | 297 ± 1 | 0.025 ± 0.015 | −40 ± 2 | — | 74 |
| CPT | 150 | 0.190 | −33 | 2.9 | 36.5 |
| PEG2 trad | 148 ± 2 | 0.095 ± 0.009 | −41 ± 3 | — | 71 |
| PEG6 trad | 131 ± 1 | 0.104 ± 0.011 | −40 ± 0.2 | — | 66 |
| PEG2-CPT trad | 120 ± 2 | 0.130 ± 0.020 | −42 ± 4 | 8.9 ± 1.1 | 61 ± 7 |
| PEG6-CPT trad | 118 ± 5 | 0.120 ± 0.030 | −35 ± 6 | 8.2 ± 0.9 | 54 ± 9 |
| mPEG2 conj | 259 ± 6 | 0.200 ± 0.040 | −33 ± 4 | — | 81 |
| mPEG2-CPT conj | 195 ± 2 | 0.230 ± 0.030 | −36 ± 3 | 10.9 ± 0.2 | 69 ± 4 |

Figure 3:
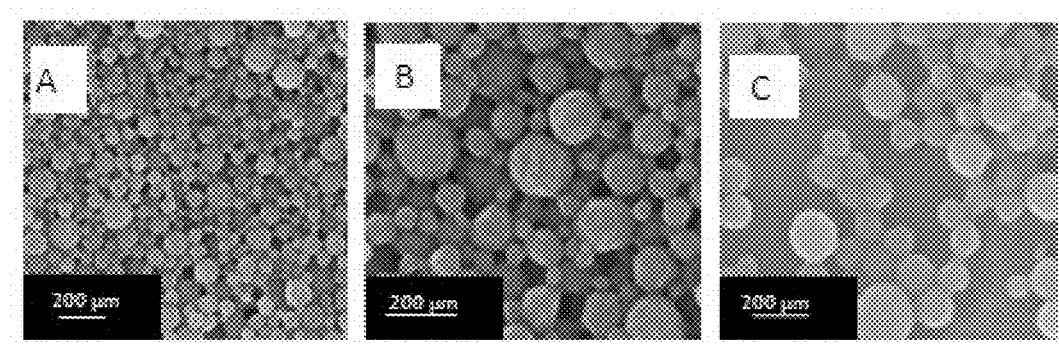
FIG. 3. Scanning Electron Microscopy (SEM) of poly (anhydride) nanoparticles formulations. A) PEG2-CPT trad (traditional PVM/MA nanoparticles pegylated with PEG2 encapsulating campthotecin); B) PEG6-CPT trad (traditional PVM/MA nanoparticles pegylated with PEG6 encapsulating campthotecin); C) mPEG2-CPT conj (nanoparticles from ester polymer conjugate of PVM/MA with mPEG2 encapsulating campthotecin).

The morphological analysis by scanning electron microscopy (FIG. 3) showed that all the poly(anhydride) nanoparticles types consisted of a homogeneous population of spherical particles of a size similar to that measured by photon correlation spectroscopy. The surface of nanoparticles appeared to be smooth with no visible rough areas on their surface.

Example 6

In Vitro and In Vivo Studies of Docetaxel 6.1 Docetaxel In Vitro Release Study

Release experiments were conducted, under sink conditions, at 37° C. using simulated gastric (SGF; pH 1.2; pepsin 0.32% w/v) and intestinal (SIF; pH 6.8; pancreatin 1% w/v) fluids containing 0.5% of polysorbate 80 (Tween® 80) as solubilising agent for docetaxel. The studies were performed under agitation in a Vortemp 56™ Shaking incubator (Labnet International Inc., NJ, USA) after the dispersion of the nanoparticles in the appropriate medium.

For each time point, 50 µg of docetaxel formulated in nanoparticles were resuspended in 2 mL of the corresponding simulated fluid. The assayed formulations were DTX nanoparticles (conventional PVM/MA nanoparticles encapsulating docetaxel), PEG2-DTX trad (traditional PVM/MA nanoparticles pegylated with PEG2 encapsulating docetaxel), mPEG2-DTX conj (nanoparticles from ester polymer conjugate of PVM/MA with mPEG2 encapsulating docetaxel) and PEG2-DTX conj (nanoparticles from ester polymer conjugate of PVM/MA with PEG2 encapsulating docetaxel).

The concentration of the nanoparticles in the release medium was adjusted in order to assess sink conditions for docetaxel. The different formulations were kept in the SGF for 2 hours and for 12 hours in SIF. At different time points, sample tubes were collected and centrifuged at 27,000×g for 20 minutes. Finally, supernatants were filtered, and the amount of docetaxel released from the formulations was quantified by HPLC (calibration curves of free docetaxel in supernatants obtained from SGF and SIF, $r^2 > 0.999$). Release profiles were expressed in terms of cumulative release percentage, and plotted versus time.

6.2 In Vivo Pharmacokinetic Studies of Nanoparticles Encapsulating Docetaxel in Balb/c Mice Administration of DTX Loaded Nanoparticles to Mice Pharmacokinetic studies were performed on Balb/c female mice (20-22 g) obtained from Harlan (Barcelona, Spain). Studies were conducted in accordance with the ethical guidelines and policies for investigations in laboratory animals approved by the Ethical Committee for Animal Experimentation of the Institution (protocol number E21-12) in accordance with the European legislation on animal experiments (86/609/EU). Before the experiment animals were adaptively fed for 1 week with free access to food and drinking water (22±2° C.; 12-h light and 12 h dark cycles; 50-60% relative humidity). Previous to the oral administration of the formulations, animals were fasted overnight to avoid interference with the absorption, allowing free access to water.

For the pharmacokinetic study, mice were randomly divided into groups based on the times of blood sampling. Each time point corresponded to 3 animals. The experimental groups were DTX, PEG2-DTX trad, mPEG2-DTX conj, and PEG2-DTX conj nanoparticles. As controls, one group of animals received Taxotere® intravenously (i.v.) and another group was treated with the commercial formulation orally. Each animal received the equivalent amount of docetaxel to a dose of 30 mg/kg body weight either orally with a blunt needle via the esophagus into the stomach or intravenously via tail vein.

Blood samples were collected at set times after administration (0, 10 min, 30 min, 1 h, 1.5 h, 3 h, 6 h, 8 h, 24 h, 48 h and 72 h). EDTA was used as anticoagulant agent. Blood volume was recovered intraperitoneally with an equal volume of normal saline solution pre-heated at body temperature. Samples were immediately placed on ice and centrifuged at 2,500×g for 10 minutes. Plasma was separated into clean tubes and kept frozen at −20° C. until HPLC analysis.

HPLC Quantification of DTX in Plasma Samples

The amount of docetaxel was determined in plasma by HPLC-UV. Calibration curves were used for the conversion of the DTX/PTX chromatographic area to concentration. Calibrator and quality control samples were prepared by adding appropriate volumes of standard docetaxel in ethanol solution to drug free plasma. Calibration curves were designed over the range 100 to 6250 ng/mL ($r^2 > 0.999$). An aliquot (200 µL) of plasma was mixed with 25 µL of internal standard solution (paclitaxel, 10 µg/mL in ethanol, previously evaporated). After vortex mixing, liquid-liquid extraction was accomplished by adding 4 mL of tert-butyl methyl ether following vortex gentle agitation (1 min). The mixture was centrifuged for 10 min at 3000×g, and then, the organic layer was transferred to a clean tube and evaporated until dry (Savant, Barcelona, Spain). Finally, the residue was dissolved in 125 µL of reconstitution solution (acetonitrile-phosphate buffer 0.01 M pH=2; 50:50, v/v) and transferred to auto-sampler vials, capped and placed in the HPLC auto-sampler. A 100 µL aliquot of each sample was injected onto the HPLC column.

Pharmacokinetic Data Analysis

The pharmacokinetic analysis of plasma concentration plotted against time data, obtained after administration of the different DTX formulations, was analyzed using a non-compartmental model with the WinNonlin 5.2 software (Pharsight Corporation, USA). The following parameters were estimated: maximal plasmatic concentration ($C_{max}$), time in which the maximum concentration is reached ($T_{max}$), area under the concentration-time curve from time 0 to ∞ (AUC), mean residence time (MRT), clearance (Cl), volume of distribution (V) and halflife in the terminal phase ($t_{1/2}z$).

Furthermore, the relative oral bioavailability, F (%), of docetaxel was estimated by the following equation:

$$F(\%) = \frac{AUC_{oral}}{AUC_{i.v.}} \times 100$$

where AUC i.v. and AUC oral corresponded to the areas under the curve for the intravenous and oral administrations, respectively.

Statistical Analysis

Data are expressed as the mean±S.D. of at least three experiments. The non-parametric Kruskall-Wallis followed by U Mann-Whitney test was used to investigate statistical differences. In all cases, p<0.05 was considered to be statistically significant. All data processing was performed using GraphPad Prism 6.0 statistical software program (GraphPad Software, CA, USA).

6.3 Results

Docetaxel In Vitro Release Study

Figure 4:
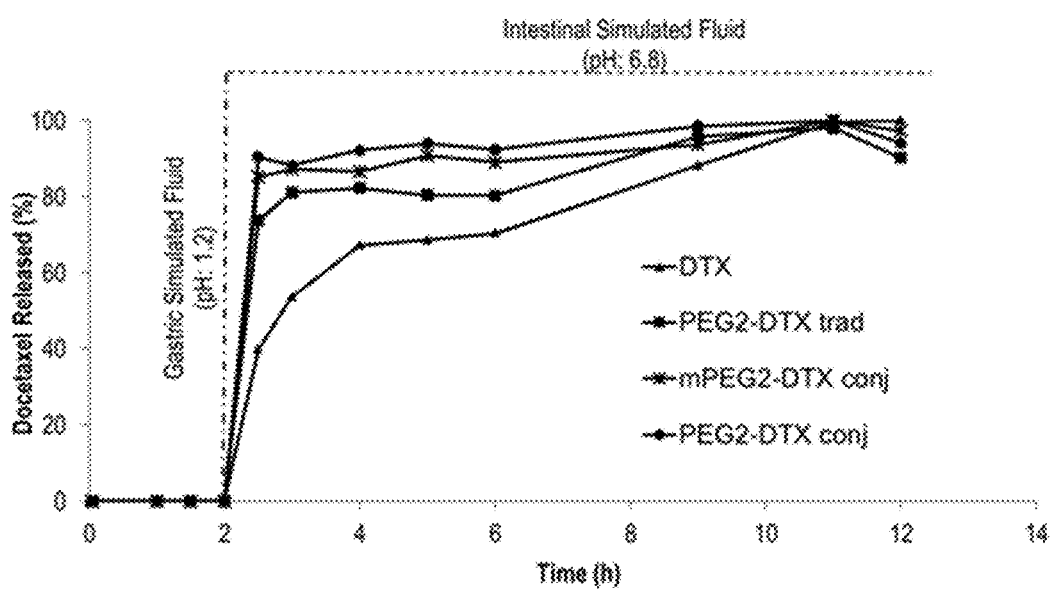
FIG. 4. Docetaxel release profile from the DTX nanoparticles (conventional PVM/MA nanoparticles encapsulating docetaxel), PEG2-DTX trad (traditional PVM/MA nanoparticles pegylated with PEG2 encapsulating docetaxel), mPEG2-DTX conj (nanoparticles from ester polymer conjugate of PVM/MA with mPEG2 encapsulating docetaxel) and PEG2-DTX conj (nanoparticles from ester polymer conjugate of PVM/MA with PEG2 encapsulating docetaxel) formulations after incubation in simulated gastric fluid (0-2 h) and simulated intestinal fluid (2-12 h) at 37° C. Data represented as mean±S.D. (n=3).

Docetaxel release profiles from nanoparticle formulations were evaluated after their incubation in two different media: simulated gastric and intestinal fluids containing 0.5% Tween 80 (w/v) as solubilising agent. FIG. 4 illustrates the release profiles of docetaxel from DTX nanoparticles, PEG2-DTX trad, PEG2-DTX conj and mPEG2-DTX conj nanoparticles formulations as cumulative percentage of drug released as a function of time. In all cases, when nanoparticles were dispersed in SGF, no drug release was observed. In contrast, when nanoparticles were dispersed in the SIF, docetaxel was released.

For PEG2-DTX trad the release pattern in SIF was characterized by an important burst effect of about 75% of the loaded drug in the first 30 min followed by a more sustained deliverance phase up to 10 hours. On the other hand, for DTX nanoparticles the release curves of docetaxel in SIF exhibited a slower discharge of docetaxel than PEG2-DTX trad followed by a more steady release up to the end of the study in which almost all of their cargo was released.

Both PEG2-DTX conj and mPEG2-DTX conj nanoparticle formulations displayed a similar release profile. In the presence of SIF, docetaxel release exhibited a biphasic release pattern characterised by a fast initial burst release up to 90% of the loaded drug followed by a more sustained deliverance phase. A complete release of DTX was obtained for all samples at 10-11 hours after the beginning of the study.

Pharmacokinetic Studies of Docetaxel-Containing Nanoparticles in Balb/c Mice

Figure 5:
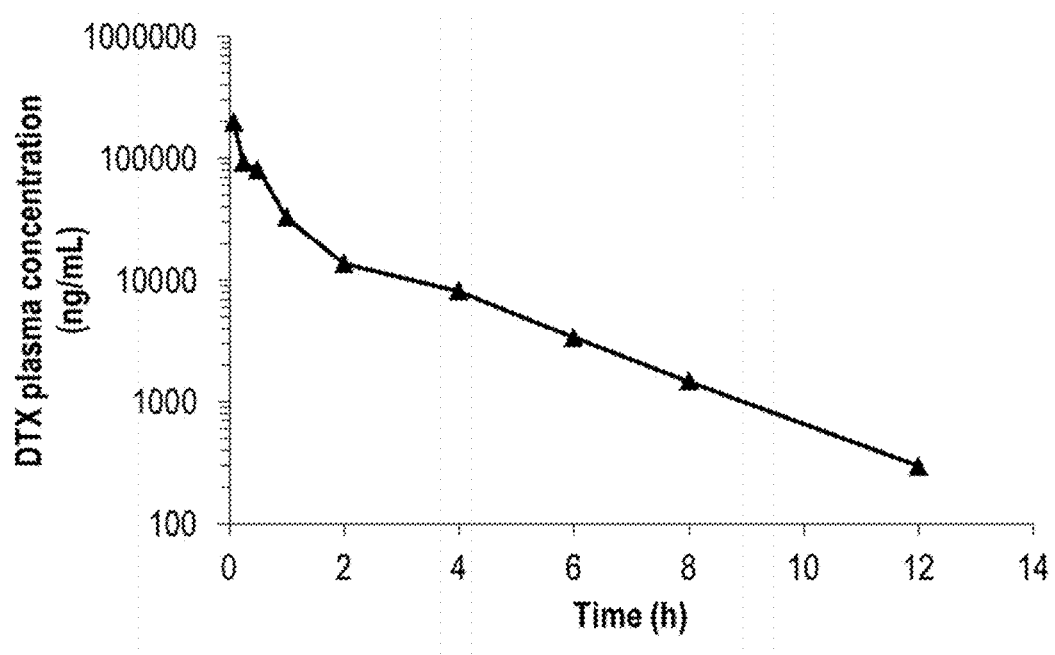
FIG. 5. Plasma docetaxel concentration-time profile after the intravenous (i.v.) administration of a 30 mg/kg dose of Taxotere®. Data are expressed as mean±S.D., (n=3 per time point).

The plasma concentration-time profile of docetaxel after i.v. administration of Taxotere® (single dose of 30 mg/Kg) to female Balb/c mice is shown in FIG. 5. The drug plasma concentration rapidly decreased with time in a biphasic way and data were adjusted to a non-compartmental model. Levels of docetaxel in plasma were quantifiable till 12 hours post-administration.

Figure 6:
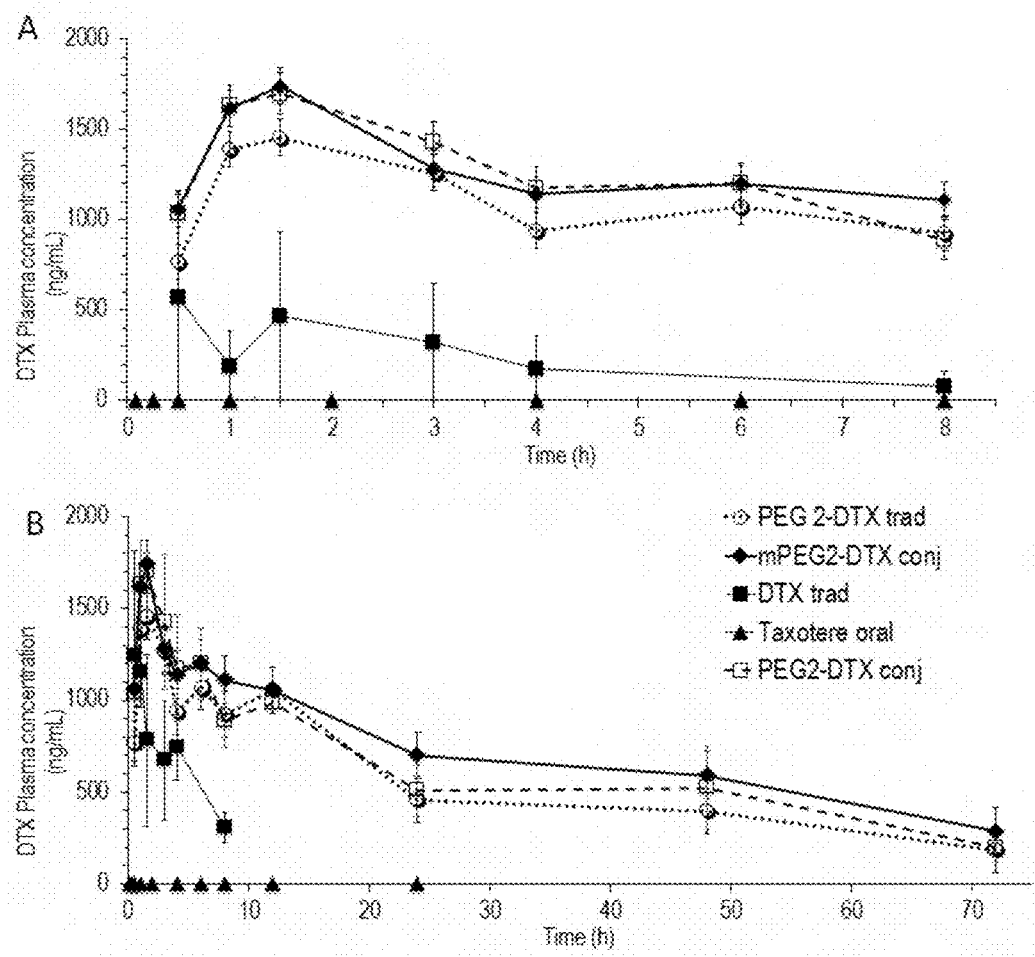
FIG. 6. Plasma docetaxel concentration-time profile after the administration of a single oral dose of 30 mg/kg. Animals received oral Taxotere®, DTX nanoparticles (conventional PVM/MA nanoparticles encapsulating docetaxel), PEG2-DTX trad (traditional PVM/MA nanoparticles pegylated with PEG2 encapsulating docetaxel), mPEG2-DTX conj (nanoparticles from ester polymer conjugate of PVM/MA with mPEG2 encapsulating docetaxel) and PEG2-DTX conj (nanoparticles from ester polymer conjugate of PVM/MA with PEG2 encapsulating docetaxel) formulations. A) within the first 8 h and B) during 72 h. Data are expressed as mean±S.D. (n=5).

FIG. 6 show the plasma concentration versus time profiles after oral administration of docetaxel (single dose of 30 mg/kg) to Balb/c mice when administered as commercial Taxotere®, or encapsulated in the different poly(anhydride) nanoparticle formulations: in conventional PVM/MA nanoparticles (DTX formulation), traditional PVM/MA nanoparticles pegylated with PEG2 (PEG2-DTX trad) or nanoparticles from ester polymer conjugates of PVM/MA with PEG2 (PEG2-DTX conj) or with mPEG2 (mPEG2-DTX conj). When commercial Taxotere® was administered to mice by the oral route docetaxel plasma levels were found to be always below the quantification limit of the chromatographic analytical technique. On the contrary, when docetaxel was loaded in nanoparticles, these formulations displayed sustained plasma levels. In all cases, there was an initial rapid rise in the anticancer plasma levels for the first 1.5-2 hours, reaching the $C_{max}$, followed by a slow decline which was prolonged for at least 8 hours for DTX formulation (see FIG. 6A), and about 70 hours for PEG2-DTX trad, PEG2-DTX conj and mPEG2-DTX conj formulations (see FIG. 6B). Comparing PEG2-DTX trad with PEG2-DTX conj and mPEG2-DTX conj, the docetaxel plasma levels reached with nanoparticles from ester polymer conjugates of PVM/MA with PEG2000 and mPEG2000 were higher than those with traditional PVM/MA nanoparticles pegylated with PEG2000.

Table 9 summarizes the pharmacokinetic parameters calculated with a non-compartmental analysis of the experimental data obtained after the administration of the different docetaxel formulations to mice. Firstly, for the commercial formulation administered by means of the i.v. route, the mean value of AUC was 143 µg h/mL. The maximum concentration (Cmax) was 198 µg/mL and Tmax 0 h. The MRT was 1.4 h and the half-life of the terminal phase ($t_{1/2}z$) of the curve was estimated to be 1.5 h.

On the other hand, $C_{max}$ values of docetaxel in the poly(anhydride) nanoparticles were between 1.3 and 2 µg/ml, being the rank order of this parameter: mPEG2-DTX conj=PEG2-DTX conj>PEG2-DTX trad>DTX. Moreover, the $C_{max}$ was reached at 0 h after the i.v. administration of Taxotere® and it was delayed to 0.8 h for DTX formulation, and 1.5-2 h for mPEG2-DTX conj, and PEG2-DTX conj formulations.

Comparing the PEG traditional and conjugate formulations, for PEG2-DTX conj and mPEG2-DTX conj, AUC values were 1.3 and 1.8 fold, respectively, higher than the AUC obtained for PEG2-DTX trad, demonstrating a higher capability to promote the oral absorption of the taxane. Furthermore, the mean residence time (MRT) of the drug in plasma and its half-life of the terminal phase ($t_{1/2}z$) were greatly extended when administered in the ester polymer conjugate formulations (mPEG2-DTX conj, PEG2-DTX conj) by the oral route.

TABLE 9

Pharmacokinetic parameters of docetaxel obtained after the intravenous and oral administration of the commercial Taxotere ® and formulated in different nanoparticles at a single dose of 30 mg/kg to Balb/c female mice. Data expressed as mean ± S.D. (n = 3)

| Formulation | Route | AUC (µg h/mL) | Cmax (µg/mL) | Tmax (h) | $t_{1/2z}$ (h) | Cl (mL/h) | V (mL) | MRT (h) | Fr |
|---|---|---|---|---|---|---|---|---|---|
| Taxotere ® | i.v. | 142.6 ± 0.8 | 197.9 ± 38 | 0 | 1.5 ± 0.1 | 3.9 ± 0.3 | 8.2 ± 0.9 | 1.4 ± 0.1 | 100 |
| Taxotere ® | oral | N.D. | N.D | N.D | N.D | N.D | N.D | N.D | N.D |
| DTX | oral | 6.9 ± 1.8 | 1.3 ± 0.5 | 0.8 | 2.2 ± 0.4 | 4.9 ± 1.2 | 15.4 ± 2.3 | 4.2 ± 0.3 | 4.9 |
| PEG2-DTX trad | oral | 45.9 ± 3.7 | 1.5 ± 0.4 | 2 | 34.7 ± 9.8 | 4.2 ± 0.3 | 192.4 ± 19.4 | 43.5 ± 9.9 | 32.2 |
| PEG2-DTX conj | oral | 58.1 ± 7.2 | 1.7 ± 0.2 | 2 | 35.8 ± 9.1 | 6.0 ± 2.4 | 225.1 ± 86.1 | 58.7 ± 79 | 40.7 |
| mPEG2-DTX conj | oral | 80.6 ± 9.1 | 1.7 ± 0.1 | 1.5 | 43.1 ± 4.4 | 4.2 ± 0.5 | 240.1 ± 87.9 | 61.1 ± 7.7 | 56.5 |

AUC: area under the concentration-time curve from time 0 to ∞; Cmax: peak plasma concentration; Tmax: time to peak plasma concentration; $t_{1/2z}$: half-life of the terminal phase; Cl: clearance; V: volumen of distribution; MRT: mean residence time; Fr: relative oral bioavailability.
N.D.: not detected.

In the same way, the volume of distribution (V) of the anticancer drug when loaded in conjugate nanoparticles (225 mL for PEG2-DTX conj and 240 mL for mPEG2-DTX conj) was higher than when the drug was intravenously administered in the form of Taxotere® (8 mL), and higher than when the drug was orally administered encapsulated in conventional PVM/MA nanoparticles (15 mL) or traditional pegylated PVM/MA nanoparticles (192 mL). On the contrary, the clearance of docetaxel was always similar and independent on both the formulation and the route of administration used.

Finally, the relative oral bioavailability of docetaxel delivered in traditional pegylated nanoparticles (PEG2-DTX trad) was calculated to be around 32%. For non-pegylated nanoparticles, the oral bioavailability was found to be only 5%. For conjugate formulations, the data obtained were high, varying from 40 to 57% for PEG2-DTX conj and mPEG2-DTX conj. Surprisingly, formulations prepared from the ester polymer conjugates enhanced the relative oral bioavailability of docetaxel.

In summary, PEG traditional and conjugate nanoparticle formulations were able to load docetaxel, presenting suitable characteristics for their oral administration. When orally administered, these nanoparticles offered prolonged and sustained plasma levels of docetaxel for 3 days. However, for "naked" nanoparticles, the docetaxel plasma concentration was initially high but decreased rapidly and no quantifiable levels were found 12 h after administration. In addition, the pharmacokinetic studies revealed a higher capability of conjugate nanocarriers to enhance the oral bioavailability of docetaxel, especially for mPEG2-DTX conj which reached an oral bioavailability close to 57%, 1.8-times higher than for traditional pegylated nanoparticles.

Example 7

In Vitro and In Vivo Studies of Camptothecin 7.1 Camptothecin In Vitro Release Study Release experiments were conducted under sink conditions at 37° C. using simulated gastric (SGF; pH 1.2; pepsin 0.32% w/v) and intestinal (SIF; pH 6.8; pancreatin 1% w/v) fluids. The studies were performed under agitation in a Vortemp 56™ Shaking Incubator (Labnet International Inc., NJ, USA) after the dispersion of the nanoparticles in the appropriate medium.

For each time point, 0.8 µg of camptothecin formulated in traditional PVM/MA nanoparticles pegylated with PEG2 (PEG2-CPT trad) or PEG6 (PEG6-CPT trad) and in nanoparticles from ester polymer conjugates of PVM/MA with mPEG2 (mPEG2-CPT conj) were resuspended in 1 mL of the corresponding simulated fluid. The different formulations were kept in the SGF for 2 h, and for 14 h in SIF. At different points simple tubes were collected and centrifuged in Vivaspin tubes (300,000 MWCO, Sartorius group, Germany) at 3,000×g for 5 min. The amount of camptothecin released from the formulations was quantified by HPLC (calibration curves of free camptothecin in supernatants obtained from SGF and SIF, $r^2 > 0.999$).

7.2 In Vivo Pharmacokinetic Studies of Nanoparticles Encapsulating Camptothecin in Wistar Rats Administration of Camptothecin-Loaded Nanoparticles to Rats Pharmacokinetic studies were performed in male Wistar rats obtained from Harlan (Barcelona, Spain). Studies were conducted in accordance with the ethical guidelines and policies for investigations in laboratory animals approved by the Ethical Committee for Animal Experimentation of the Institution (protocol number 058-12) in accordance with the European legislation on animal experiments (86/609/EU).

Before the experiment, animals were adaptively fed for 1 week with free access to food and drinking water (22±2° C.; 12 h light and 12 h dark cycles; 50-60% relative humidity). Previous to the oral administration of the formulations, animals were fasted overnight to avoid interference with the absorption, allowing free access to water.

For the pharmacokinetic study, rats were randomly divided into 2 groups (n=6). As controls, one group of animals received a dose of 1 mg/kg of a camptothecin suspension orally (with a blunt needle via the esophagus into the stomach) and other group received the camptothecin suspension intravenously (via tail vein). The experimental groups orally received the equivalent camptothecin dose formulated in mPEG2-CPT conj and PEG2-CPT trad nanoparticles.

Blood samples were collected at set times after administration (0, 0.5, 1, 2, 4, 6, 8, 24, 30 and 48 h). EDTA was used as anticoagulant agent. Blood volume was recovered intraperitoneally with an equal volume of normal saline solution pre-heated at body temperature. Samples were immediately placed on ice and centrifuged at 2,500×g for 10 min. Plasma was separated into clean tubes and kept frozen at −20° C. until HPLC analysis.

HPLC Quantification of Camptothecin in Plasma Samples

The amount of camptothecin was determined in plasma by HPLC-FLD in an Agilent model 1100 series LC and fluorescence detector set at excitation and emission of 380 and 418 nm, respectively. The chromatographic system was equipped with a reversed-phase 150 mm×3 mm C18 Phenomenex Gemini column (particle size 5 µm) and precolumn (Phenomenex Security Guard C18). The mobile phase, pumped at 1 mL/min consisted on a mixture 50:50 (v/v) of acetonitrile and a solution of trifluoroacetic acid 0.01% (v/v). The column was placed at 30° C. and the injection volume was 100 μL. Calibration curves and quality controls were designed over the range of 0.48 and 8000 ng/mL ($r^2>0.999$) by adding appropriate volumes of standard camptothecin in dimethylsulfoxide/acetonitrile/trifluoroacetic acid 1:8.9:0.1 (v/v/v) to drug free plasma.

An aliquot (100 μL) of plasma was mixed with 4 volumes of acetonitrile and vortexed for 2 minutes in order to achieve the precipitation of the plasma proteins. After centrifugation (5000×g, 5 minutes), the supernatant was collected and evaporated until dry (Savant, Barcelona, Spain). Finally, the residue was dissolved in 120 μL of reconstitution solution dimethylsulfoxide/acetonitrile/trifluoroacetic acid 1:8.9:0.1 (v/v/v) and transferred to autosampler vials, capped and placed in the HPLC autosampler. The limit of quantification was calculated to be 2.6 ng/mL with a relative standard deviation of 4.6%.

Pharmacokinetic Data Analysis

The pharmacokinetic analysis of plasma concentration plotted against time data, obtained after administration of the different camptothecin formulations, was analyzed using a non-compartmental model with the WinNonlin 5.2 software (Pharsight Corporation, USA). The following parameters were estimated: maximal plasmatic concentration ($C_{max}$), time in which the maximum concentration is reached ($T_{max}$), area under the concentration-time curve from time 0 to ∞ (AUC), mean residence time (MRT), clearance (Cl), volume of distribution (V) and half-life in the terminal phase ($t_{1/2}z$).

Furthermore, the relative oral bioavailability, Fr, of camptothecin was expressed as the ratio between the area under the concentration-time curve from time 0 to ∞ (AUC) of the formulations assayed and the one of the oral suspension of CPT administered.

Statistical Analysis

For the physico-chemical and pharmaceutical characterizations of formulations, data are expressed as the mean±standard deviation (S.D.) of at least three experiments.

Pharmacokinetic in vivo parameters were analysed statistically. The non-parametric Kruskall-Wallis followed by Mann-Whitney U-test was used to investigate statistical differences. In all cases, P values lower than 0.05 were considered as statistically significant difference. All data processing was performed using GraphPad Prism 5.0 statistical software (GraphPad Software, USA).

7.3 Results

Camptothecin In Vitro Release Study

Figure 7:
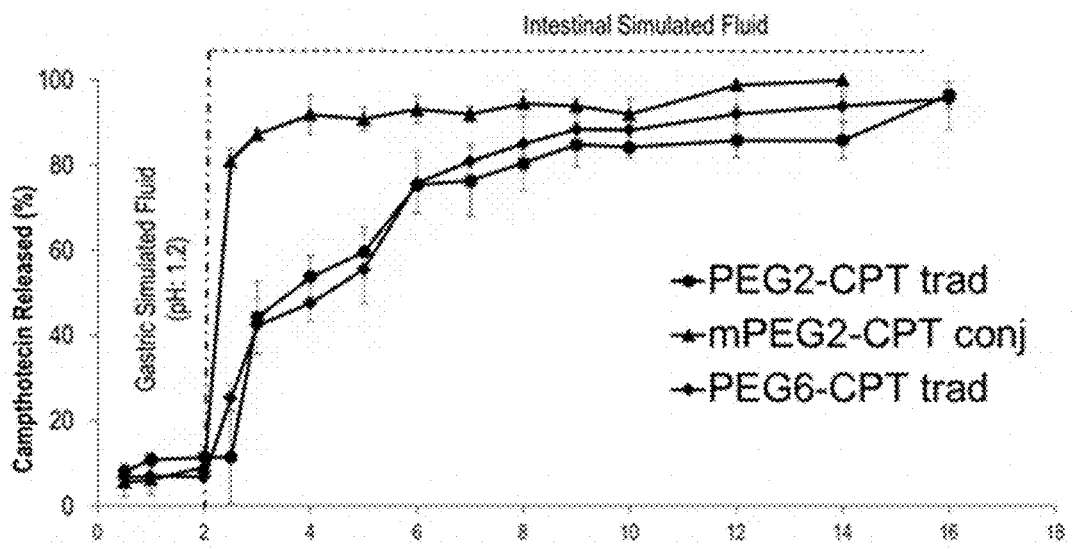
FIG. 7. Campthotecin release profile from PEG2-CPT trad (traditional PVM/MA nanoparticles pegylated with PEG2 encapsulating camptothecin), PEG6-CPT trad (traditional PVM/MA nanoparticles pegylated with PEG6 encapsulating camptothecin) and mPEG2-CPT conj (nanoparticles from ester polymer conjugate of PVM/MA with mPEG2 encapsulating camptothecin) formulations, after incubation in simulated gastric fluid (0-2 h) and simulated intestinal fluid (2-14 h) under sink conditions, 37° C., 60 rpm. Data expressed as mean±S.D., (n=3).

Camptothecin release kinetics from nanoparticles was evaluated in simulated gastric and intestinal fluids (containing polysorbate 80 as solubilizing agent for camptothecin) (FIG. 7). This pattern was characterised by a first non-release step when nanoparticles were dispersed in SGF, and a release step (when nanoparticles dispersed in SIF) in which the drug was initially rapidly released followed by a more sustained deliverance phase. For traditional pegylated nanoparticles (PEG2-CPT trad and PEG6-CPT trad), this quicker release took effect in the first 5 hours (after incubation in SIF) and the last step of sustained release took 11 hours until the nanoparticles completed the release of 100% of their cargo. Camptothecin release kinetics from mPEG2-CPT conj showed a release profile that can be divided in three different phases. In the first one, when nanoparticles were dispersed in SGF during the first 2 h, the amount of camptothecin released was very low (about 10%). Then, when nanoparticles were moved to a SIF, a burst release effect was observed. Thus, around 90% of the initial drug loaded was brusquely released from the nanoparticle formulation. Finally, the third step was characterised by a slow and sustained release of the remaining drug that was completely released within the next 12 hours of experiment (14 hours after the beginning of the study).

Pharmacokinetic Studies of Camptothecin-Containing Nanoparticles in Wister Rats

Figure 8:
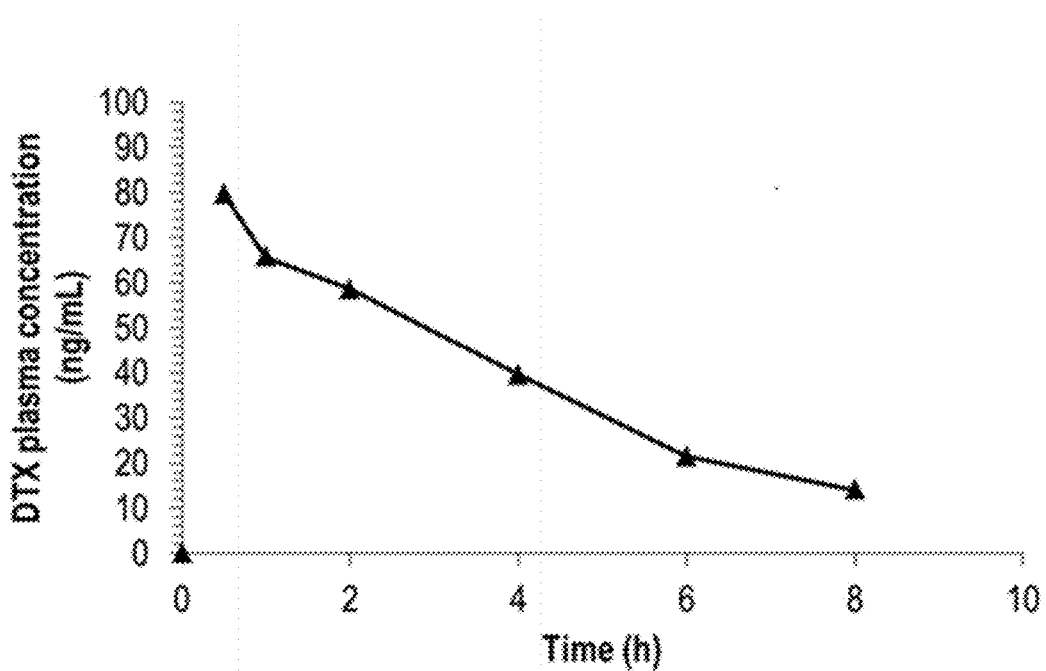
FIG. 8. Plasma campthotecin concentration-time profile after the intravenous (i.v.) administration of a 1 mg/kg dose of suspension. Data are expressed as mean±S.D., (n=3 per time point).

The plasma concentration-time profile of camptothecin after a single intravenous administration at a dose of 1 mg/kg is shown in FIG. 8. Camptothecin was administered as a suspension with a particle size of 1,500±144 nm and a PDI of 0.44±0.05. Data were analysed by a non-compartmental model. Camptothecin plasma concentration decreased rapidly after the administration, not being detectable 6 hours after the administration. After administration, the drug plasma concentration reached 430 ng/mL ($C_{max}$) and the values for AUC and $t_{1/2}z$, were 0.39 μg h/mL and 0.69 hours, respectively. Clearance and distribution volume of the drug were calculated to be 755 mL/h and 683 mL, respectively (Table 10).

Figure 9:
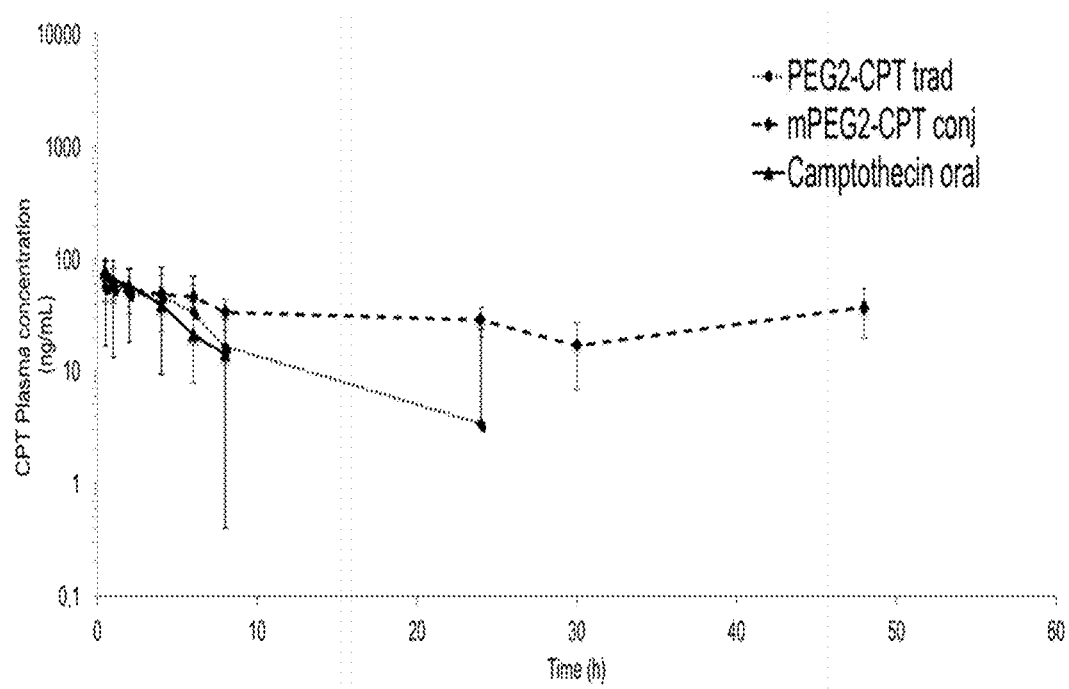
FIG. 9. Plasma concentration-time profile of campthotecin in male Wistar rats after a single dose (1 mg/kg) of an oral suspension, PEG2-CTP trad (traditional PVM/MA nanoparticles pegylated with PEG2 encapsulating campthotecin) and mPEG2-CPT conj (nanoparticles from ester polymer conjugate of PVM/MA with mPEG2 encapsulating campthotecin) formulations. Data expressed as mean±S.D. (n=6).

FIG. 9 shows the plasma concentration profiles of camptothecin after the administration of a single oral dose (1 mg/kg) to male Wistar rats either in suspension or loaded in nanoparticles. When the drug suspension was administered orally, the plasma levels increased rapidly reaching the $C_{max}$ 30 min after administration. Then sustained plasma levels of the drug were maintained for at least 4 hours and, finally, the camptothecin levels decreased rapidly. Thus, 10 hours after administration not detectable levels of camptothecin in plasma were observed.

For camptothecin loaded in nanoparticles and administered at the same dose (1 mg/kg), the main difference with the aqueous suspension formulation was that the drug levels were quantifiable in plasma for a more extended period of time. Thus, animals that received camptothecin included in traditional pegylated nanoparticles (PEG2-CPT trad) showed a first phase characterized by increasing levels of drug in plasma for the first 1.5 hours, followed by a slow and prolonged decrease phase with quantifiable levels of camptothecin until 24 hours. AUC was found to be about 2-times higher than when the drug was orally administered as a suspension. Besides, although no statistical differences were found, the volume of distribution of the drug when administered in these pegylated nanoparticles was 1.5 times the one of the bare drug orally administered as a suspension.

For nanoparticles from ester polymer conjugates of PVM/MA (mPEG2-CPT conj) administered at the same dose (1 mg/kg), the initial profile of the plasma curve was quite similar; however, the quantified amount of drug was higher than for the conventional formulation and, more important, the plasma levels were sustained in time till 48 h post-administration. Overall, the levels of camptothecin obtained in plasma after the oral administration of mPEG2-CPT conj were higher than for the aqueous suspension and for traditional pegylated nanoparticles (PEG2-CPT trad), being AUC 7.6 times and 4.2 times higher, respectively.

Table 10 summarises the main pharmacokinetic parameters estimated with a non-compartmental analysis of the experimental data obtained after the administration of the different formulations to rats. For mPEG2-CPT conj, the camptothecin AUC was found to be significantly higher ($p<0.05$) than for the aqueous suspension of the drug. Another difference between nanoparticles and the suspension was the mean residence time of the drug (MRT). In this case, MRT was significantly different ($p<0.01$) between the bare drug and mPEG2-CPT conj (10-times higher) but no significant difference was found between the control and PEG2-CPT trad. Similarly, the half-life of the terminal phase of the curve ($t_{1/2}z$) was also significantly higher when camptothecin was encapsulated in mPEG2-CPT conj than when formulated as a traditional suspension, but not when formulated in PEG2-CPT trad. In accordance with this result, the clearance of the drug when administered in mPEG2-CPT conj was about 11-times lower than the value obtained when administered as a suspension (p<0.01). Likewise, when the mPEG2-CPT conj formulation was compared to PEG2-CPT trad, AUC was found to be significantly higher (p<0.05), and statistical significances were also found regarding MRT and $t_{1/2z}$ (p<0.01).

Institution in agreement with the European legislation on animal experiments (protocol number 059-13). A single dose of 1 mL of an aqueous suspension containing 10 mg of fluorescently labelled nanoparticles was orally administered to male Wistar rats. Two hours later, the animals were sacrificed and the guts were removed. Ileum portions of 1 cm were collected, stored in the tissue proceeding medium Tissue-Tek® OCT and frozen at −80° C. Each portion was then cut into 5 μm sections on a cryostat and attached to glass slides. Finally, these samples were fixed with formaldehyde and incubated with DAPI (4′,6-diamidino-2-phenylindole) for 15 minutes before the cover assembly.

The presence of fluorescently loaded nanoparticles in the intestinal mucosa was visualized in a fluorescence micro-

TABLE 10

Pharmacokinetic parameters estimated after a single oral dose of 1 mg/kg of CPT suspension, PEG2-CPT trad and mPEG2-CPT conj. Data expressed as mean (±S.D.) (n = 6)

| Formulation | Route | AUC (μg h/mL) | Cmax (μg/mL) | Tmax (h) | $t^{1/2}z$ (h) | Cl (mL/h) | V (mL) | MRT (h) | Fr |
|---|---|---|---|---|---|---|---|---|---|
| CPT suspension | i.v. | 0.39 ± 0.12 | 0.43 ± 0.25 | 0.01 | 0.69 ± 0.13 | 755 ± 289 | 683 ± 147 | 1 ± 0.4 | — |
| CPT suspension | oral | 0.38 ± 0.21 | 0.08 ± 0.02 | 0.5 | 1.6 ± 0.8 | 619 ± 357 | 1545 ± 414 | 5.9 ± 1.4 | 1 |
| PEG2-CPT trad | oral | 0.7 ± 0.31 | 0.07 ± 0.03 | 3 | 3.2 ± 1.1 | 534 ± 221 | 2383 ± 1003 | 11.4 ± 5.5 | 1.8 |
| mPEG2-CPT conj | oral | 2.9 ± 1.2*† | 0.08 ± 0.03 | 1.5 | 25.4 ± 10.7**†† | 84 ± 63**†† | 2510 ± 1110 | 51 ± 20**†† | 7.6 |

†Man-Whitney U-test mPEG2-CPT conj vs PEG2-CPT trad (p-value < 0.05).
††Man-Whitney U-test mPEG2-CPT conj vs PEG2-CPT trad (p-value < 0.01).
*Man-Whitney U-test mPEG2-CPT conj vs Camphtotecin oral suspension (p-value < 0.05).
**Man-Whitney U-test mPEG2-CPT conj vs Camphtotecin oral suspension (p-value < 0.01).
AUC: area under the concentration-time curve from time 0 to ∞; Cmax: peak plasma concentration; Tmax: time to peak plasma concentration; $t^{1/2}z$: half-life of the terminal phase; Cl: clearance; V: volumen of distribution; MRT: mean residence time; Fr: relative oral bioavailability.

In summary, both types of nanoparticles (PEG2-CPT trad and mPEG2-CPT conj) encapsulating camptothecin appeared to be suitable for the oral administration in the in vitro assay, given that no release of the drug was observed until they were incubated under intestinal conditions. However, in the in vivo assay, mPEG2-CPT conj showed a remarkably higher bioavailability, 4.3 times the one of PEG2-CPT trad.

Example 8

Biodistribution Studies of Nanoparticles

In order to visualize and evaluate the distribution and the capacity of the nanoparticles comprising a matrix of an ester polymer conjugate of PVM/MA to interact with the gut mucosa, fluorescence microscopy studies were carried out.
8.1 Preparation of Lumogen-Loaded Nanoparticles Empty conventional PVM/MA nanoparticles and nanoparticles comprising a matrix of an ester polymer conjugate of PVM/MA with methoxy polyethyleneglycol 2,000 (mPEG2 conj) were fluorescently labelled with lumogen red.

Lumogen-loaded nanoparticles were prepared by adding 0.5 mg of Lumogen® red in the acetone phase (5 mL) containing the PVM/MA (Gantrez® AN) or its ester polymer conjugate with mPEG2 (mPEG2-LUM conj) before de formation of nanoparticles as described in examples 1 and 4. LUM and mPEG2-LUM conj formulations were respectively obtained.
8.2 In Vivo Distribution Studies of Lumogen-Loaded Nanoparticles in the Gut Mucosa in Wistar Rats Biodistribution studies were carried out using fluorescently labelled nanoparticles encapsulating lumogen red.

Animal experiments were performed following a protocol approved by the Ethical and Biosafety Committee of the scope (Axioimager M1, Zeiss) with a coupled camera (Axiocam ICc3, Zeiss) and fluorescent source (HBO 100, Zeiss).
8.3 Results Lumogen-loaded nanoparticles displayed similar physico-chemical properties to those determined for empty nanoparticles: 215 nm, −36 mV for LUM nanoparticles and 205 nm, −35 mV for mPEG2-LUM conj formulations.

Figure 10:
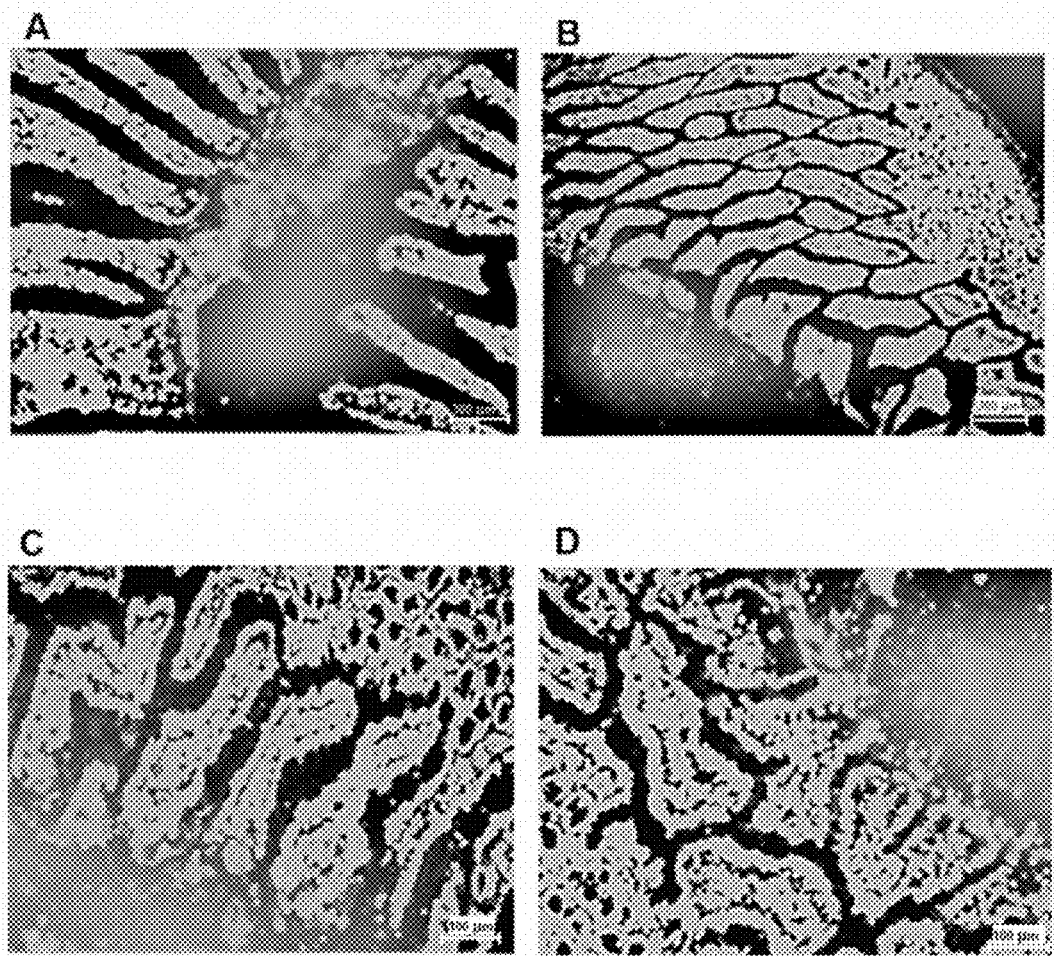
FIG. 10. Fluorescence microscopic visualisation of nanoparticles fluorescently labelled with lumogen red, in longitudinal sections of the proximal ileum of rats, two hours after their oral administration as a single dose. (A, B) conventional PVM/MA nanoparticles encapsulating Lumogen® red; (C, D) nanoparticles comprising a matrix of an ester polymer conjugate of PVM/MA with mPEG2 encapsulating Lumogen® red (mPEG2-LUM conj).

Surprisingly, mPEG2-LUM conj nanoparticles displayed a different distribution within the ileum mucosa than LUM nanoparticles. Conventional PVM/MA nanoparticles appear to be trapped in the mucus layer covering the intestinal epithelium (FIG. 10A, 10B) whereas nanoparticles from ester polymer conjugates of PVM/MA were capable of crossing the mucus layer and interacting in a more intimate way with the surface of the enterocytes (FIG. 10C, 10D). This finding confirms that the surface of nanoparticles from ester polymer conjugates is different to that of the original PVM/MA. It is possible to hypothesize that during the formation of nanoparticles the hydrophilic areas of conjugates would be oriented through the aqueous phase forming a hydrophilic corona in the surface of nanoparticles, which would confer "slippery" properties to the resulting nanoparticles and, therefore, the capability to cross the mucus layer and reach the surface of the enterocytes.

The invention claimed is:
1. A process for producing a nanoparticle, said process comprises the steps of:
   a) mixing an ester polymer conjugate with a biologically active compound in an organic medium, and
   b) desolvating the ester polymer conjugate by means of adding alcohol and water, in the presence of a divalent metal,
   wherein the ester polymer conjugate is a conjugate of poly(methyl vinyl ether-co-maleic anhydride) with a hydroxyl-terminated molecule, wherein said hydroxyl- terminated molecule is selected from a polyethylene glycol and a derivative thereof containing a hydroxyl-terminal reactive group.

2. The process according to claim 1 wherein step b) is performed by means of adding a hydroalcoholic mixture comprising a divalent metal to the mixture obtained in step a).

3. The process according to claim 1, wherein the weight ratio between the ester polymer conjugate and the biologically active compound in the mixture of step a) is 1:0.01-0.20.

4. The process according to claim 1, wherein the ester polymer conjugate is obtainable by a process comprising the steps of:
a) reacting the poly (methyl vinyl ether-co-maleic anhydride) with the hydroxyl-terminated molecule in an organic solvent, and
b) removing the organic solvent.

5. The process according to claim 4 which further comprises purifying the ester polymer conjugate.

6. The process according to claim 4, wherein the weight ratio between the poly (methyl vinyl ether-co-maleic anhydride) and the hydroxyl-terminated molecule in the solution of step a) is 1:0.01-0.25.

7. The process according to claim 1, wherein the hydroxyl-terminated molecule is a polyethylene glycol selected from the group consisting of polyethylene glycol 1,000 (PEG1), polyethylene glycol 2,000 (PEG2), polyethylene glycol 6,000 (PEG6), and polyethylene glycol 10,000 (PEG10).

8. The process according to claim 1, wherein the polyethylene glycol derivative containing a hydroxyl-terminal reactive group is a polyoxyethylene alkyl ether.

9. The process according to claim 8, wherein the polyoxyethylene alkyl ether is a polyethylene glycol methyl ether.

10. The process according to claim 9, wherein the polyethylene glycol methyl ether is selected from the group consisting of metoxi-polyethylene glycol 1,000 (mPEG1), metoxi-polyethylene glycol 2,000 (mPEG2), metoxi-polyethylene glycol 6,000 (mPEG6), and metoxi-polyethylene glycol 10,000 (mPEG10).

11. The process according to claim 1, wherein the biologically active compound is an anti-tumor agent.

12. A nanoparticle obtained by a process according to claim 1.

13. A pharmaceutical composition comprising i) at least one nanoparticle according to claim 12, and ii) a pharmaceutically acceptable carrier or vehicle.

14. The pharmaceutical composition according to claim 13, further comprising an antitumor agent.

15. The pharmaceutical composition according to claim 14 selected from the group consisting of:
a pharmaceutical composition comprising:
a) an ester polymer conjugate of poly (methyl vinyl ether-co-maleic anhydride) with polyethylene glycol 2,000 from 38% to 47%,
b) docetaxel from 3% to 5%,
c) calcium from 0.1% to 0.2%, and
d) a saccharide from 15% to 40%,
wherein all the proportions are by weight with respect to the total weight of the composition;
a pharmaceutical composition comprising:
a) an ester polymer conjugate of poly (methyl vinyl ether-co-maleic anhydride) with metoxi-polyethylene glycol 2,000 from 38% to 47%,
b) docetaxel from 3% to 5%,
c) calcium from 0.1% to 0.2%, and
d) a saccharide from 15% to 40%,
wherein all the proportions are by weight with respect to the total weight of the composition; and
a pharmaceutical composition comprising:
a) an ester polymer conjugate of poly (methyl vinyl ether-co-maleic anhydride) with metoxi-polyethylene glycol 2,000 from 30% to 40%,
b) camptothecin from 0.08% to 1.5%,
c) calcium from 0.1% to 0.2%, and
d) a saccharide from 15% to 40%,
wherein all the proportions are by weight with respect to the total weight of the composition.

16. The process according to claim 1, wherein the organic medium is acetone.

* * * * *